US012630542B2

(12) United States Patent
Steger et al.

(10) Patent No.: US 12,630,542 B2
(45) Date of Patent: *May 19, 2026

(54) COMPOUNDS AND THEIR USE AS THERAPEUTICALLY ACTIVE SUBSTANCES IN THE TREATMENT AND/OR PREVENTION OF DISEASES INVOLVING THE RETINAL PIGMENT EPITHELIUM

(71) Applicant: ENDOGENA THERAPEUTICS, INC., San Francisco, CA (US)

(72) Inventors: Matthias Steger, Zurich (CH); Alex Mueller, Zurich (CH); Mauro Marigo, Zurich (CH)

(73) Assignee: ENDOGENA THERAPEUTICS, INC., San Francisco, CA (US)

( * ) Notice: Subject to any disclaimer, the term of this patent is extended or adjusted under 35 U.S.C. 154(b) by 649 days.

This patent is subject to a terminal disclaimer.

(21) Appl. No.: 18/011,234

(22) PCT Filed: Jun. 19, 2020

(86) PCT No.: PCT/US2020/038715
§ 371 (c)(1),
(2) Date: Dec. 19, 2022

(87) PCT Pub. No.: WO2021/257092
PCT Pub. Date: Dec. 23, 2021

(65) Prior Publication Data

US 2023/0322749 A1 Oct. 12, 2023

(51) Int. Cl.
*C07D 413/12* (2006.01)
*C07D 263/32* (2006.01)

(52) U.S. Cl.
CPC ......... *C07D 413/12* (2013.01); *C07D 263/32* (2013.01)

(58) Field of Classification Search
CPC ............................ C07D 263/32; C07D 413/12
See application file for complete search history.

(56) References Cited

U.S. PATENT DOCUMENTS 6,066,675 A 5/2000 Wen et al.
6,117,675 A 9/2000 van der Kooy et al.
(Continued)

FOREIGN PATENT DOCUMENTS

AU 2019226198 9/2019
CN 103656742 B 4/2015
(Continued)

OTHER PUBLICATIONS

Dec. 12, 2022 International Preliminary Report on Patentability issued in International Patent Application No. PCT/US2020/038715.

(Continued)

*Primary Examiner* — Shawquia Jackson
(74) *Attorney, Agent, or Firm* — Oliff PLC

(57) ABSTRACT

A method of treating and/or preventing disease involving retinal pigment epithelium, including administering compound of formula (I)

(I)

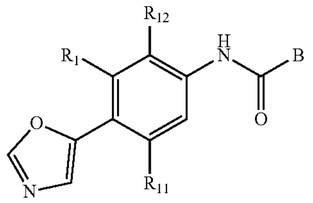

or a pharmaceutically acceptable salt, a racemic mixture, a corresponding enantiomer or a corresponding diastereomer thereof, wherein: $R_1$, $R_{11}$ and $R_{12}$ are independently selected from the group consisting of hydrogen, fluoro, chloro, methoxy, trifluoromethyl, methyl and difluoromethoxy, whereby at least one of $R_1$, $R_{11}$ and $R_{12}$ is not hydrogen, B is selected from the group consisting of a residue of formula (II), (III), (IV), (V), (VI) and (VII)

(II)

(III)

(IV)

(Continued)

-continued (V)

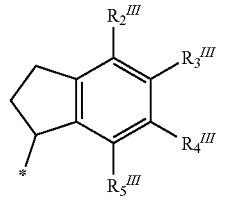

(VI)

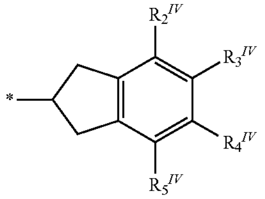

(VII)

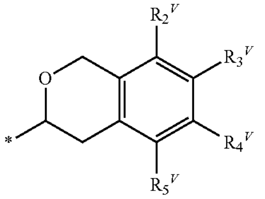

wherein, "*" denotes point of attachment to remainder of the molecule, and $R_2$, $R_3$, $R_4$, $R_5$, $R_2^I$, $R_3^I$, $R_4^I$, $R_5^I$, $R_2^{II}$, $R_3^{II}$, $R_4^{II}$, $R_5^{II}$, $R_2^{III}$, $R_3^{III}$, $R_4^{III}$, $R_5^{III}$, $R_2^{IV}$, $R_3^{IV}$, $R_4^{IV}$, $R_5^{IV}$, $R_2^V$, $R_3^V$, $R_4^V$, $R_5^V$ are independently selected from the group consisting of hydrogen, a linear or branched alkyl having 1 to 3 carbon atoms, fluoro, chloro, bromo, methoxy, ethoxy, propoxy, trifluoromethyl and difluoromethoxy.

19 Claims, 1 Drawing Sheet

(56) References Cited

U.S. PATENT DOCUMENTS

| | | | |
|---|---|---|---|
| 9,815,819 | B2 | 11/2017 | Altmann et al. |
| 10,752,593 | B2 | 8/2020 | Steger et al. |
| 10,807,973 | B2 | 10/2020 | Steger et al. |
| 11,541,039 | B2 | 1/2023 | Steger et al. |
| 11,844,755 | B2 | 12/2023 | Steger et al. |
| 2006/0148852 | A1 | 7/2006 | Takayama et al. |
| 2009/0325959 | A1 | 12/2009 | Vittitow et al. |
| 2015/0290215 | A1 | 10/2015 | Kusari et al. |
| 2016/0213671 | A1 | 7/2016 | Ueffing et al. |
| 2020/0207749 | A1 | 7/2020 | Steger et al. |
| 2022/0089547 | A1 | 3/2022 | Steger et al. |
| 2022/0089583 | A1 | 3/2022 | Steger et al. |
| 2023/0124312 | A1 | 4/2023 | Steger et al. |

FOREIGN PATENT DOCUMENTS

| | | | |
|---|---|---|---|
| EP | 1101759 | A1 | 5/2001 |
| RU | 2 628 697 | C2 | 8/2017 |
| WO | 99/55663 | A1 | 11/1999 |
| WO | 2001/039792 | A2 | 6/2001 |
| WO | 02/064545 | A1 | 8/2002 |
| WO | 2009/027392 | A1 | 3/2009 |
| WO | 2009/075874 | A1 | 6/2009 |
| WO | 2009/079008 | | 6/2009 |
| WO | 2009079011 | A1 | 6/2009 |
| WO | 2013/016252 | A1 | 1/2013 |
| WO | 2013/029338 | A1 | 3/2013 |
| WO | 2014/079850 | A1 | 5/2014 |
| WO | 2015/138628 | | 9/2015 |
| WO | 2016/029191 | | 2/2016 |
| WO | 2016/073931 | A1 | 5/2016 |
| WO | 2016/165808 | A1 | 10/2016 |
| WO | 2020/140050 | | 7/2020 |

OTHER PUBLICATIONS

U.S. Appl. No. 15/946,469, filed Apr. 5, 2018 in the name of Matthias Steger et al.
Loewenstein et al., "Outer Retinal Degeneration, An Electronic Retinal Prosthesis as a Treatment Strategy," Arch Ophthalmol, vol. 122, pp. 587-596, 2004.
Dec. 28, 2018 Office Action issued in U.S. Appl. No. 15/946,469.
May 8, 2019 Office Action issued in U.S. Appl. No. 15/946,469.
Jul. 19, 2019 Office Action issued in U.S. Appl. No. 16/235,543.
Oct. 9, 2019 Office Action Issued in U.S. Appl. No. 16/235,543.
Mar. 23, 2020 Notice of Allowance Issued in U.S. Appl. No. 16/235,543.
Mar. 11, 2020 International Search Report issued in International Patent Application No. PCT/US2019/068759.
Mar. 11, 2020 Written Opinion issued in International Patent Application No. PCT/US2019/068759.
Mar. 9, 2020 International Search Report issued in International Patent Application No. PCT/US2019/068768.
Jul. 22, 2020 Notice of Allowance issued in U.S. Appl. No. 16/235,429.
Mar. 9, 2020 Written Opinion issued in International Patent Application No. PCT/US2019/068768.
Feb. 4, 2020 Office Action issued in U.S. Appl. No. 16/235,429.
U.S. Appl. No. 16/235,429, filed Dec. 28, 2018 in the name of Matthias Steger et al.
U.S. Appl. No. 17/418,019, filed Dec. 27, 2019 in the name of Matthias Steger et al.
U.S. Appl. No. 16/235,543, filed Dec. 28, 2018 in the name of Matthias Steger et al.
U.S. Appl. No. 17/418,057, filed Dec. 27, 2019 in the name of Matthias Steger et al.
Sep. 24, 2020 International Search Report issued in International Patent Application No. PCT/US2020/038715.
Sep. 24, 2020 Written Opinion issued in International Patent Application No. PCT/US2020/038715.
Feng et al., "Discovery of Substituted 4-(Pyrazol-4-yl)-phenylbenzodioxane-2-carboxamides as Potent and Highly Selective Rho Kinase (ROCK-II) Inhibitors", Journal of Medicinal Chemistry, vol. 51, No. 21, pp. 6642-6645, 2018.
Feb. 29, 2024 Office Action issued in Canadian Patent Application No. 3,125,327.
Jan. 2, 2024 Office Action issued in Chinese Patent Application No. 201980085766.5.
RN: 2192535-97-8, Chemical Abstract, Entry date: Mar. 16, 2018.
RN: 2192535-09-2, Chemical Abstract, Entry date: Mar. 16, 2018.
RN: 2191263-76-8, Chemical Abstract, Entry date: Mar. 14, 2018.
RN: 2176692-30-9, Chemical Abstract, Entry date: Feb. 20, 2018.
RN: 2093772-78-0, Chemical Abstract, Entry date: Apr. 30, 2017.
RN: 2093621-47-5, Chemical Abstract, Entry date: Apr. 28, 2017.
RN: 2093584-39-3, Chemical Abstract, Entry date: Apr. 28, 2017.
RN: 1647398-48-8, Chemical Abstract, Entry date: Feb. 15, 2015.
RN: 1444312-86-0, Chemical Abstract, Entry date: Jul. 16, 2013.
RN: 1436130-27-6, Chemical Abstract, Entry date: Jun. 9, 2013.
RN: 1390017-27-2, Chemical Abstract, Entry date: Aug. 12, 2012.
RN: 1299804-72-0, Chemical Abstract, Entry date: May 24, 2011.
RN: 1294163-48-6, Chemical Abstract, Entry date: May 13, 2011.
RN: 1281131-45-0, Chemical Abstract, Entry date: Apr. 17, 2011.
RN: 1088188-77-5, Chemical Abstract, Entry date: Dec. 22, 2008.
Jan. 4, 2022 International Search Report issued in International Patent Application No. PCT/US2021/053577.
Jan. 4, 2022 Written Opinion issued in International Patent Application No. PCT/US2021/053577.
Feb. 18, 2022 Office Action Issued in U.S. Appl. No. 17/065,795.
Jun. 22, 2022 Office Action issued in U.S. Appl. No. 17/065,795.

(56) References Cited

OTHER PUBLICATIONS

Aug. 17, 2022 Notice of Allowance Issued in U.S. Appl. No. 17/065,795.
May 9, 2023 Office Action issued in U.S. Appl. No. 17/988,909.
Aug. 21, 2023 Notice of Allowance Issued In U.S. Appl. No. 17/988,909.
U.S. Appl. No. 17/065,795, filed Oct. 8, 2020 in the name of Matthias Steger et al.
U.S. Appl. No. 17/988,909, filed Nov. 17, 2022 in the name of Matthias Steger et al.
U.S. Appl. No. 18/030,917, filed Apr. 7, 2023 in the name of Matthias Steger et al.
May 3, 2024 Office Action issued in U.S. Appl. No. 17/418,019.
Feb. 7, 2024 Extended Search Report issued in European Patent Application No. 20941410.1.
Bowne et al., "Spectrum and Frequency of Mutations in IMPDH1 Associated with Autosomal Dominant Retinitis Pigmentosa and Leber Congenital Amaurosis", Investigative Opthalmology & Visual Science, Jan. 2006, vol. 47, No. 1, pp. 34-42.
Oct. 11, 2023, Notice of Reasons for Refusal issued in 2021-537222.
Sep. 11, 2024 Notice of Allowance issued in U.S. Appl. No. 17/418,019.
Aug. 8, 2025 Office Action issued in U.S. Appl. No. 18/030,917.
E. Hampton Sessions, "Benzimidazole- and benzoxazole-based inhibitors of Rho Kinase", Bioorganic and Medicinal Chemistry Letters 18,Elsevier, Oct. 25, 2008.
Linus S. Lin et al, Bioisosteric replacement of anilide with benzoxazole: potent and orally bioavailable antagonists of VLA-4, Bioorganic and Medicinal-Chemistry Letters 14, (Jan. 29, 2004).
Shikha Kumari et al, "Amide Bond Bioisosteres: Strategies, Synthesis, and Success", Medicinal Chemistry, Jul. 20, 2020.
Jun. 11, 2025 Office Action issued in Japanese Application No. 2023-521666.
May 29, 2025 Office Action issued in Chinese Application No. 2021800667225.

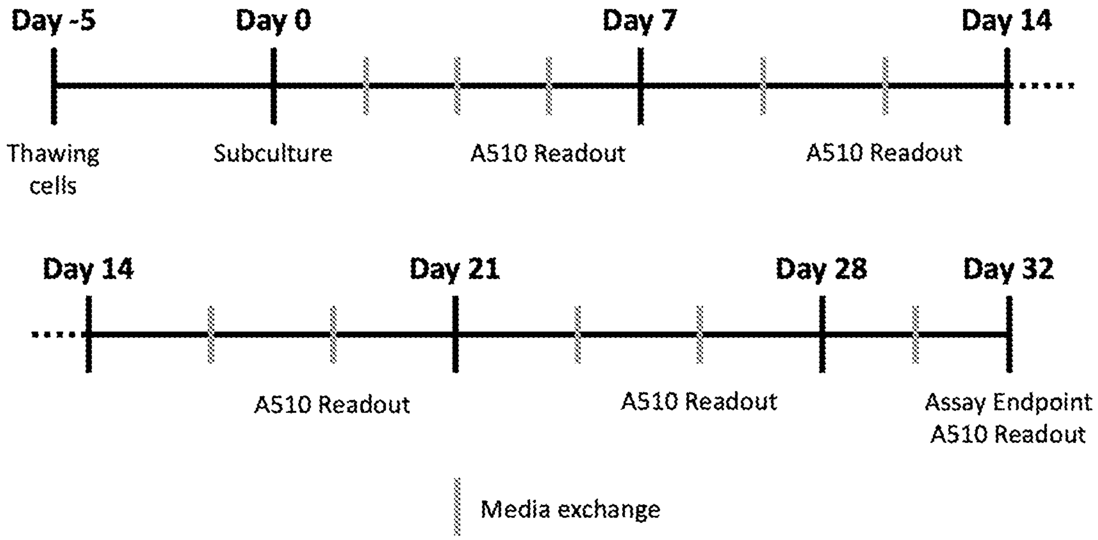
Schematic representation of RPE compound screens regimen.

COMPOUNDS AND THEIR USE AS THERAPEUTICALLY ACTIVE SUBSTANCES IN THE TREATMENT AND/OR PREVENTION OF DISEASES INVOLVING THE RETINAL PIGMENT EPITHELIUM

The present invention relates to new compounds and to their use as therapeutically active substances in the treatment and/or prevention of diseases involving the retinal pigment epithelium, and in particular in the treatment and/or prevention of diseases leading to atrophy, degeneration or death of the retinal pigment epithelium that might also result in atrophy or loss of photoreceptors and/or retinal neovascularization.

An important family of diseases that involves degeneration and death of the retinal pigment epithelium (RPE) is macular degeneration. Macular degeneration is characterized by a progressive loss of central vision associated with abnormalities of Bruch's membrane, the choroid, the neural retina and/or the retinal pigment epithelium. The macula describes the central region of the retina with an approximate diameter of 0.3 to 0.5 cm. Because of its high density of cones, the macula provides detailed vision for activities such as reading, driving or recognizing faces.

So called age-related macular degeneration (AMD), the most prevalent form of macular degeneration, is associated with progressive loss of visual acuity in the central portion of the visual field, changes in color vision, and abnormal dark adaptation and sensitivity. AMD is a leading cause of irreversible vision loss in the developed world affecting approximately 2% of individuals. The prevalence of AMD increases with age and its etiology is multifactorial.

Among the key contributors to the disease and its progression are the loss of functional RPE cells and changes in their basement membrane, the Bruch's membrane. The RPE is a continuous cellular monolayer lying between the light-sensitive photoreceptors and the choroid, the blood supply of the retina. As the RPE cells perform a nourishing role to the highly metabolic photoreceptors by providing energy and growth factors, removing waste, and recycling essential compounds of the visual cycle, loss of the RPE ultimately leads to photoreceptor failure and loss.

Two principal clinical manifestations of AMD have been described as the dry or atrophic form (hereinafter referred to as dry AMD) and the wet or neovascular form (hereinafter referred to as wet AMD). Dry AMD is associated with atrophic cell death of the central retina or macula. About 10-20% of these dry AMD patients further progress to the second form, known as wet or neovascular AMD. In these advanced stages of AMD, atrophy of the RPE (geographic atrophy) and/or development of new blood vessels derived from choroidal vessels (neovascularization) further result in the death of photoreceptors and central vision loss. This loss of central vision, which is crucial for reading, the recognition of faces, and performing many daily tasks, essentially cuts the sufferer off from the world around.

No approved treatments currently exist for dry AMD or its advanced form known as geographic atrophy (GA), and many patients with neovascular AMD become legally blind despite current therapy with anti-VEGF agents such as Lucentis®. The pharmacological approaches for treating loss of vision in dry AMD caused by underlying RPE damage vary, but they are all directed to controlling the mechanisms believed to initially cause the damage (e.g. the complement system) rather than reversing the damage caused by the loss of RPE cells. Alternative approaches under investigation involve transplantation of induced pluripotent stem cells or mature RPE cells.

Drusen are tiny yellow or white accumulations of extracellular material that build up between Bruch's membrane and the retinal pigment epithelium of the eye. The presence of drusen is the hallmark of age-related macular degeneration. Recent studies of drusen, have implicated a role for inflammation and other immune-mediated processes, in particular complement activation, in the aetiology of early and late forms of AMD. EP 2 302 076 discloses that Factor H protein (HF1), the major inhibitor of the alternative complement pathway, accumulates within drusen, and is synthesized locally by the retinal pigment epithelium and thus provides the administration of a medicament that decreases the amount of a variant Factor H or expression of a gene encoding Factor H in an amount effective to reduce a symptom of AMD in the patient.

U.S. Pat. No. 9,815,819 B2 relates to compounds that modulate, and preferably inhibit, activation of the alternative complement pathway as a method of treating or preventing AMD.

WO 2015/138628 relates to AAV vector constructs that are capable of, and optimized for, delivering anti-inflammatory peptides to the retina of AMD patients.

AU 2019/226198 discloses a method of producing a substantially purified culture of RPE cells suitable for transplantation.

CN 103656742 relates to a preparation method of functionalized retinal pigment epithelial cell grafts for transplantation to the retina of AMD patients.

RU 2628697 discloses a procedure to produce a cell layer from retinal pigment epithelial cells in a convenient and stable manner without using an artificial membrane and leading to high rate of engraftment when transplanted intraocularly.

PCT/US19/68768 describes the application of small molecules for triggering endogenous regeneration of photoreceptors derived from retinal stem and progenitor cells in retinal dystrophies i.e. retinitis pigmentosa. In contrast, the present invention relates to the treatment and/or prevention of RPE-related ocular diseases by stimulating pigmentation and/or growth of mammalian RPE cells.

In the case of wet AMD, there has been great progress in the development of drugs that antagonize the effects of vascular endothelial growth factor (anti-VEGF). However, these treatments do not address the damage of the RPE layer but only suppress neovascularization. Also, they are not curative but only effective at keeping the current state of the disease.

The problem of the present invention is therefore to provide therapeutic agents for the treatment and/or prevention of RPE-related diseases and particularly for the treatment of AMD.

The problem is solved by a compound of formula (I). Further preferred embodiments are subject of the dependent claims.

It has been shown that the new compounds of formula (I) stimulate pigmentation and/or growth of mammalian RPE cells. This stimulation of pigmentation and/or growth of the endogenous RPE cells allows a controlled repair and regeneration of the retina. Thus, it is possible to prevent vision loss and/or restore vision by endogenously generating new healthy RPE cells by a compound according to the present invention. Therefore, the compound of formula I is useful as a therapeutically active substance in the treatment and/or prevention of diseases leading to atrophy, death or degeneration of the retinal pigment epithelium, i.e. as a medicament.

The term "RPE cells" encompasses in this context any form of proliferative and non-proliferative retinal pigment epithelial cells that can support or give rise to further differentiated functional tissues of the eye. RPE cells are smooth, pigmented and hexagonal in shape. Healthy and fully differentiated RPE cells build melanosomes, which contain the light-absorbing pigment melanin. Compounds that promote the differentiation of healthy and functional RPE cells hence lead to the presence of pigmentation.

The term "growth of mammalian RPE cells" stands for the controlled promotion of RPE cell proliferation and a corresponding increase in RPE cell numbers.

The term "prevention" refers to the prevention or reduction of signs and symptoms associated with RPE-related diseases, in particular of macular degeneration leading to vision loss in subjects who are at risk for developing the disease. In these subjects a predisposing factor may be retained, but the signs and/or symptoms of the disease do not occur or take significantly longer to develop. Further, it also includes the prevention of a further deterioration of the symptoms once the disease has occurred.

Thus, the present invention relates to a method of treating and/or preventing a disease involving the retinal pigment epithelium, comprising administering the compound of formula (I)

(I)

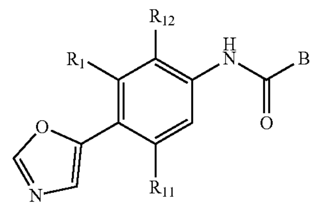

or a pharmaceutically acceptable salt, a racemic mixture, a corresponding enantiomer or, if applicable, a corresponding diastereomer thereof, wherein:

$R_1$, $R_{11}$ and $R_{12}$ are independently selected from the group consisting of hydrogen, fluoro, chloro, methoxy, trifluoromethyl, methyl, dimethylaminoethoxy and difluoromethoxy, whereby at least one of $R_1$, $R_{11}$ and $R_{12}$ is not hydrogen, B is selected from the group consisting of a residue of formula (II), (III), (IV), (V), (VI), (VII)

(II)

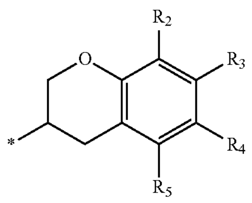

-continued (III)

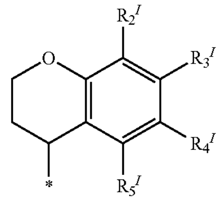

(IV)

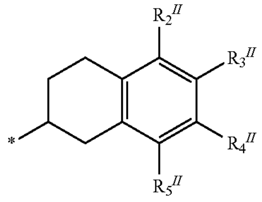

(V)

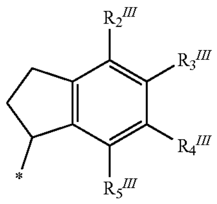

(VI)

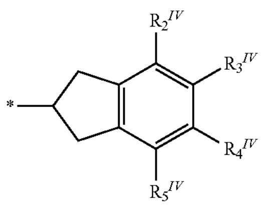

(VII)

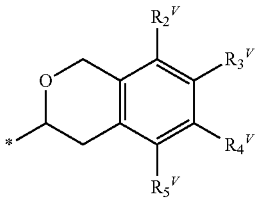

wherein,

"*" denotes the point of attachment to the remainder of the molecule, and $R_2$, $R_3$, $R_4$, $R_5$, $R_2^I$, $R_3^I$, $R_4^I$, $R_5^I$, $R_2^{II}$, $R_3^{II}$, $R_4^{II}$, $R_5^{II}$, $R_2^{III}$, $R_3^{III}$, $R_4^{III}$, $R_5^{III}$, $R_2^{IV}$, $R_3^{IV}$, $R_4^{IV}$, $R_5^{IV}$, $R_2^{V}$, $R_3^{V}$, $R_4^{V}$, $R_5^{V}$ are independently selected from the group consisting of hydrogen, a linear or branched alkyl having 1 to 3 carbon atoms, fluoro, chloro, bromo, methoxy, ethoxy, propoxy, trifluoromethyl and difluoromethoxy.

The term "pharmaceutically acceptable salt" stands for therapeutically active, non-toxic acid salt forms, which the compound according to the present invention is able to form.

In one embodiment of the present invention the asymmetric center at ring position * of the residue of formula (II), (III), (IV), (V), (VI) and (VII) has the configuration as depicted below, that is a compound of formula (Ii)

(I)

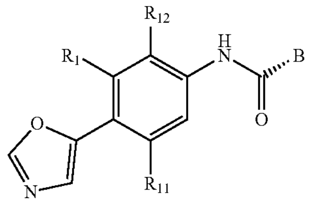

and B is selected from the group consisting of a residue of formula (II), (III), (IV), (V), (VII)

(II)

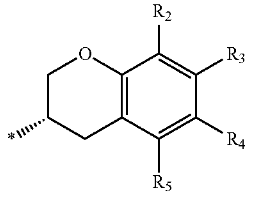

(III)

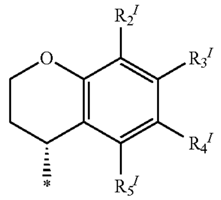

(IV)

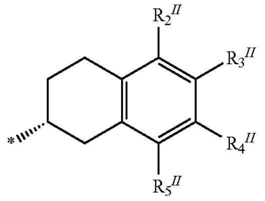

(V)

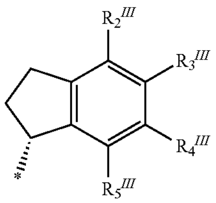

(VI)

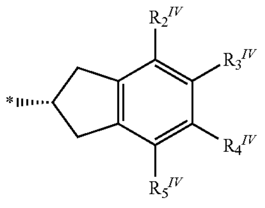

(VII)

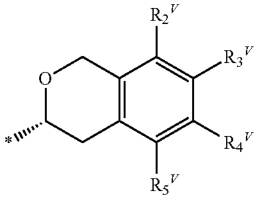

and $R_2$, $R_3$, $R_4$, $R_2$, $R_2^I$, $R_3^I$, $R_4^I$, $R_5^I$, $R_2^{II}$, $R_3^{II}$, $R_4^{III}$, $R_5^{II}$, $R_2^{III}$, $R_3^{III}$, $R_4^{III}$, $R_5^{III}$, $R_2^{IV}$, $R_3^{IV}$, $R_4^{IV}$, $R_5^{IV}$, $R_2^V$, $R_3^V$, $R_4^V$, $R_5^V$ have the same definition as above.

In another embodiment of the present invention the asymmetric center at ring position * of the residue of formula (II), (III), (IV), (V), (VI) and (VII) is in the configuration as depicted below, that is a compound of formula (Iii)

(Iii)

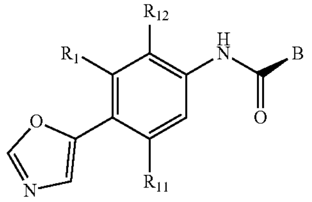

and B is selected from the group consisting of a residue of formula (II), (III), (IV), (V), (VI) and (VII)

(II)

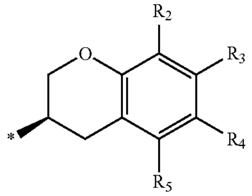

(III)

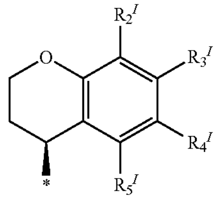

(IV)

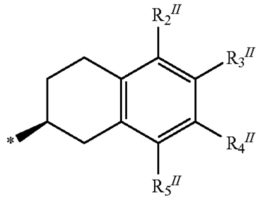

(V)

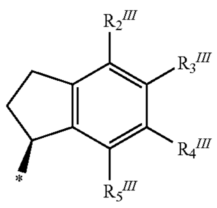

(VI)

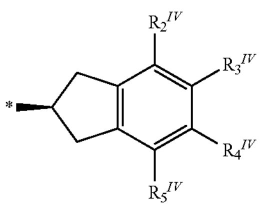

-continued (VII)

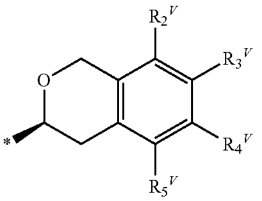

and $R_2$, $R_3$, $R_4$, $R_5$, $R_2^I$, $R_3^I$, $R_4^I$, $R_5^I$, $R_2^{II}$, $R_3^{II}$, $R_4^{II}$, $R_5^{II}$, $R_2^{III}$, $R_3^{III}$, $R_4^{III}$, $R_5^{III}$, $R_2^{IV}$, $R_3^{IV}$, $R_4^{IV}$, $R_2^V$, $R_3^V$, $R_4^V$, $R_5^V$ have the same definition as above.

Thus, the residue B can be unsubstituted, monosubstituted or polysubstituted. The term "unsubstituted" means that all residues of B are hydrogen. The term "monosubstituted" means that one of the residues of B is not hydrogen and the term "polysubstituted" means that at least two of the residues of B are not hydrogen.

Preferably, the residue B is unsubstituted or monosubstituted.

Preferably, in the residue B of the compound of formula (I), the residues $R_3$, $R_4$, $R_3^I$, $R_4^I$, $R_3^{II}$, $R_4^{II}$, $R_3^{III}$, $R_4^{III}$, $R_3^{IV}$, $R_4^{IV}$, $R_3^V$, $R_4^V$ are independently selected from the group consisting of hydrogen, chloro, fluoro, methoxy and ethoxy.

In one embodiment, the residues $R_2$, $R_3$, $R_5$, $R_2^I$, $R_3^I$, $R_5^I$, $R_2^{II}$, $R_3^{II}$, $R_5^{II}$, $R_2^{III}$, $R_3^{III}$, $R_5^{III}$, $R_2^{IV}$, $R_3^{IV}$, $R_5^{IV}$, $R_2^V$, $R_3^V$, $R_5^V$ are hydrogen and $R_4$, $R_4^I$, $R_4^{II}$, $R_4^{III}$, $R_4^{IV}$, $R_4^V$ are selected from the group consisting of fluoro, chloro, methoxy, and ethoxy.

In another embodiment, in the monosubstituted residue B of the compound of formula (I), the residues $R_2$, $R_4$, $R_5$, $R_2^I$, $R_4^I$, $R_5^I$, $R_2^{II}$, $R_4^{II}$, $R_5^{II}$, $R_2^{III}$, $R_4^{III}$, $R_5^{III}$, $R_2^{IV}$, $R_4^{IV}$, $R_5^{IV}$, $R_2^V$, $R_4^V$, $R_5^V$ are hydrogen and $R_3$, $R_3^I$, $R_3^{II}$, $R_3^{III}$, $R_3^{IV}$, $R_3^V$ are selected from the group consisting of fluoro, chloro, methoxy, and ethoxy.

In a further embodiment, in the compound of the present invention, $R_1$ is chloro or methoxy, $R_{11}$ and $R_{12}$ are both hydrogen, and the residue B is unsubstituted or monosubstituted, preferably monosubstituted. Said compounds show an outstanding biological activity.

In a further aspect of the present invention, in the compound of the present invention, $R_{12}$ is methyl, difluoromethoxy or dimethylamino-ethoxy, $R_1$ and $R_{11}$ are both hydrogen, and the residue B is unsubstituted or monosubstituted.

In a further aspect of the present invention, in the compound of the present invention, $R_1$ is methyl or trifluoromethyl, $R_{12}$ and $R_{11}$ are both hydrogen, and the residue B is unsubstituted or monosubstituted.

In a further aspect of the present invention, in the compound of the present invention, $R_1$ and $R_{11}$ are independently from each other chloro, fluoro or methoxy, $R_{12}$ is hydrogen, and the residue B is unsubstituted or monosubstituted.

One embodiment of the present invention relates to the compound of formula (Ia)

(Ia)

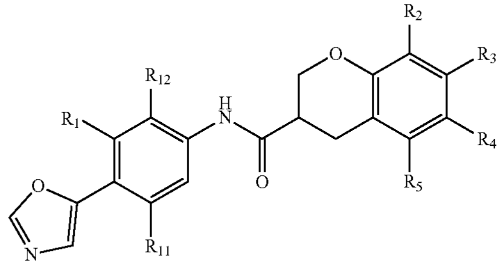

or a pharmaceutically acceptable salt, a racemic mixture, a corresponding enantiomer or, if applicable, a corresponding diastereomer thereof, wherein:

$R_1$, $R_{11}$, $R_{12}$, $R_2$, $R_3$, $R_4$ and $R_5$ have the same definition as above. Preferably, the residue B in formula Ia is unsubstituted or monosubstituted. Most preferably, $R_1$ is chloro, $R_{11}$ and $R_{12}$ are hydrogen, and the residue B is unsubstituted.

Alternatively preferred, $R_1$ is chloro, $R_{11}$ and $R_{12}$ are hydrogen, and the residue B is monosubstituted, where $R_2$ and $R_5$ are hydrogen, and one of $R_3$ or $R_4$ is hydrogen and the other residue is selected from the group consisting of fluoro, chloro, methoxy and ethoxy, i.e., the residue B is monosubstituted and either $R_3$ or $R_4$ is selected from the group consisting of fluoro, chloro, methoxy and ethoxy.

Another embodiment of the present invention relates to the compound of formula (Ib)

(Ib)

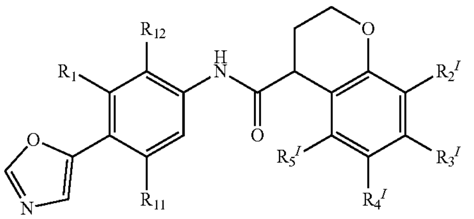

or a pharmaceutically acceptable salt, a racemic mixture, a corresponding enantiomer or, if applicable, a corresponding diastereomer thereof, wherein:

$R_1$, $R_{11}$, $R_{12}$, $R_2^I$, $R_3^I$, $R_4^I$ and $R_5^I$ have the same definition as above. Preferably, the residue B in formula Ib is unsubstituted or monosubstituted. Most preferably, $R_1$ is chloro, $R_{11}$ and $R_{12}$ is hydrogen, and the residue B is unsubstituted.

Alternatively preferred, $R_1$ is chloro, $R_{11}$ and $R_{12}$ is hydrogen, and the residue B is monosubstituted, where $R_2^I$ and $R_5^I$ are hydrogen, and one of $R_3^I$ or $R_4^I$ is hydrogen and the other residue is selected from the group consisting of fluoro, chloro, methoxy and ethoxy, i.e., the residue B is monosubstituted and either $R_3^I$ or $R_4^I$ is selected from the group consisting of fluoro, chloro, methoxy and ethoxy.

Another embodiment of the present invention relates to the compound of formula (Ic)

(Ic)

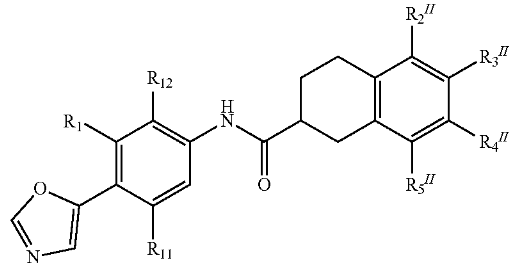

or a pharmaceutically acceptable salt, a racemic mixture, a corresponding enantiomer or, if applicable, a corresponding diastereomer thereof, wherein:

$R_1$, $R_{11}$, $R_{12}$, $R_2^{II}$, $R_3^{II}$, $R_4^{II}$ and $R_5^{II}$ have the same definition as above. Preferably, the residue B in formula Ic is unsubstituted or monosubstituted. Most preferably, $R_1$ is chloro, $R_{11}$ and $R_{12}$ is hydrogen, and the residue B is unsubstituted.

Alternatively preferred, $R_1$ is chloro, $R_{11}$ and $R_{12}$ is hydrogen, and the residue B is monosubstituted, where $R_2^{II}$ and $R_5^{II}$ are hydrogen, and one of $R_3^{II}$ or $R_4^{II}$ is hydrogen and the other residue is selected from the group consisting of fluoro, chloro, methoxy and ethoxy, i.e., the residue B is monosubstituted and either $R_3^{II}$ or $R_4^{II}$ is selected from the group consisting of fluoro, chloro, methoxy and ethoxy.

Another embodiment of the present invention relates to the compound of formula (Id)

(Id)

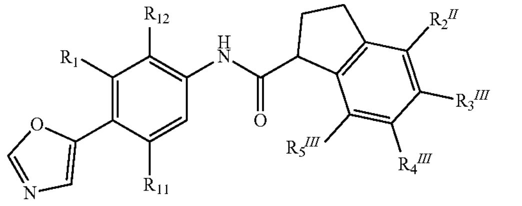

or a pharmaceutically acceptable salt, a racemic mixture, a corresponding enantiomer or, if applicable, a corresponding diastereomer thereof, wherein:

$R_1$, $R_{11}$, $R_{12}$, $R_2^{III}$, $R_3^{III}$, $R_4^{III}$ and $R_5^{III}$ have the same definition as above. Preferably, the residue B in formula Id is unsubstituted or monosubstituted. Most preferably, $R_1$ is chloro, $R_{11}$ and $R_{12}$ is hydrogen, and the residue B is unsubstituted.

Alternatively preferred, $R_1$ is chloro, $R_{11}$ and $R_{12}$ is hydrogen, and the residue B is monosubstituted, where $R_2^{III}$ and $R_5^{III}$ are hydrogen, and one of $R_3^{III}$ or $R_4^{III}$ is hydrogen and the other residue is selected from the group consisting of fluoro, chloro, methoxy and ethoxy, i.e., the residue B is monosubstituted and either $R_3^{III}$ or $R_4^{III}$ is selected from the group consisting of fluoro, chloro, methoxy and ethoxy.

Another embodiment of the present invention relates to the compound of formula (Ie)

(Ie)

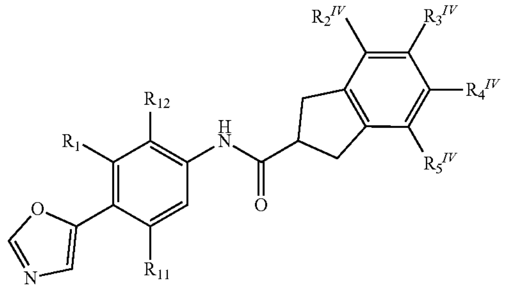

or a pharmaceutically acceptable salt, a racemic mixture, a corresponding enantiomer or, if applicable, a corresponding diastereomer thereof, wherein:

$R_1$, $R_{11}$, $R_{12}$, $R_2^{IV}$, $R_3^{IV}$, $R_4^{IV}$ and $R_5^{IV}$ have the same definition as above. Preferably, the residue B in formula Ie is unsubstituted or monosubstituted. Most preferably, $R_1$ is chloro, $R_{11}$ and $R_{12}$ is hydrogen, and the residue B is unsubstituted.

Alternatively preferred, $R_1$ is chloro, $R_{11}$ and $R_{12}$ is hydrogen, and the residue B is monosubstituted, where $R_2^{IV}$ and $R_5^{IV}$ are hydrogen, and one of $R_3^{IV}$ or $R_4^{IV}$ is hydrogen and the other residue is selected from the group consisting of fluoro, chloro, methoxy and ethoxy, i.e., the residue B is monosubstituted and either $R_3^{IV}$ or $R_4^{IV}$ is selected from the group consisting of fluoro, chloro, methoxy and ethoxy.

Another embodiment of the present invention relates to the compound of formula (If)

(If)

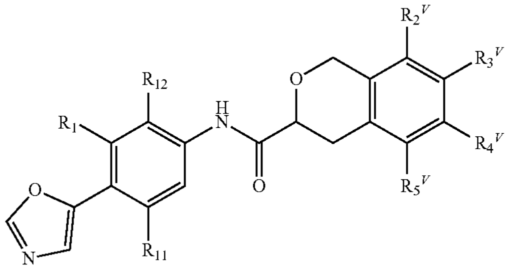

or a pharmaceutically acceptable salt, a racemic mixture, a corresponding enantiomer or, if applicable, a corresponding diastereomer thereof, wherein:

$R_1$, $R_{11}$, $R_{12}$, $R_2^{V}$, $R_3^{V}$, $R_4^{V}$ and $R_5^{V}$ have the same definition as above. Preferably, the residue B in formula If is unsubstituted or monosubstituted. Most preferably, $R_1$ is chloro, $R_{11}$ and $R_{12}$ is hydrogen, and the residue B is unsubstituted.

Alternatively preferred, $R_1$ is chloro, $R_{11}$ and $R_{12}$ is hydrogen, and the residue B is monosubstituted, where $R_2^{V}$ and $R_5^{V}$ are hydrogen, and one of $R_3^{V}$ or $R_4^{V}$ is hydrogen and the other residue is selected from the group consisting of fluoro, chloro, methoxy and ethoxy, i.e., the residue B is monosubstituted and either $R_3^{V}$ or $R_4^{V}$ is selected from the group consisting of fluoro, chloro, methoxy and ethoxy.

Preferably, the compound of formula (Ia)

(Ia)

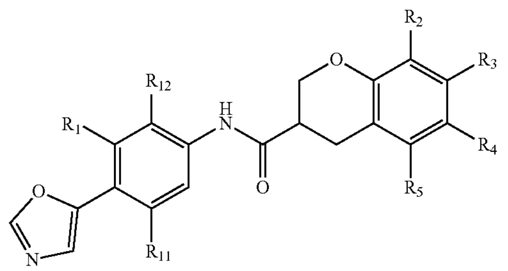

is selected from the group consisting of compounds of the formula (I), wherein $R_1$, $R_{11}$, $R_{12}$, $R_2$, $R_3$, $R_4$ and $R_5$ are as indicated in Table 1:

TABLE 1

| $R_1$ | $R_{11}$ | $R_{12}$ | $R_2$ | $R_3$ | $R_4$ | $R_5$ |
|---|---|---|---|---|---|---|
| $CF_3$ | H | H | F | H | H | H |
| $CF_3$ | H | H | H | $CH_3$ | H | H |
| $CF_3$ | H | H | H | F | H | H |
| $CF_3$ | H | H | H | H | F | H |
| $CF_3$ | H | H | H | H | H | $OCH_3$ |
| $CF_3$ | H | H | H | H | Cl | H |
| $CF_3$ | H | H | H | H | $OCH_3$ | H |
| $CH_3$ | H | H | F | H | H | H |
| $CH_3$ | H | H | H | $CH_3$ | H | H |
| $CH_3$ | H | H | H | F | H | H |
| $CH_3$ | H | H | H | H | F | H |
| $CH_3$ | H | H | H | H | H | $OCH_3$ |
| $CH_3$ | H | H | H | H | Cl | H |
| $CH_3$ | H | H | H | H | $OCH_3$ | H |
| Cl | H | H | F | H | F | H |
| Cl | H | H | F | H | H | H |
| Cl | H | H | H | $CH_3$ | H | H |
| Cl | H | H | H | F | F | H |
| Cl | H | H | H | F | H | H |
| Cl | H | H | H | H | Cl | H |
| Cl | H | H | H | H | F | H |
| Cl | H | H | H | H | H | $OCF_2H$ |
| Cl | H | H | H | H | H | $OCH_3$ |
| Cl | H | H | H | H | $OCF_2H$ | H |
| Cl | H | H | H | H | $OCH_3$ | H |
| F | H | H | F | H | H | H |
| F | H | H | H | $CH_3$ | H | H |
| F | H | H | H | F | H | H |
| F | H | H | H | H | F | H |
| F | H | H | H | H | H | $OCH_3$ |
| F | H | H | H | H | Cl | H |
| F | H | H | H | H | $OCH_3$ | H |
| H | H | $CF_3$ | F | H | H | H |
| H | H | $CF_3$ | H | $CH_3$ | H | H |
| H | H | $CF_3$ | H | F | H | H |
| H | H | $CF_3$ | H | H | F | H |
| H | H | $CF_3$ | H | H | H | $OCH_3$ |
| H | H | $CF_3$ | H | H | Cl | H |
| H | H | $CF_3$ | H | H | $OCH_3$ | H |
| H | H | $CH_3$ | F | H | H | H |
| H | H | $CH_3$ | H | $CH_3$ | H | H |
| H | H | $CH_3$ | H | F | H | H |
| H | H | $CH_3$ | H | H | F | H |
| H | H | $CH_3$ | H | H | H | $OCH_3$ |
| H | H | $CH_3$ | H | H | Cl | H |
| H | H | $CH_3$ | H | H | $OCH_3$ | H |
| H | H | $OCF_2H$ | F | H | H | H |
| H | H | $OCF_2H$ | H | $CH_3$ | H | H |
| H | H | $OCF_2H$ | H | F | H | H |
| H | H | $OCF_2H$ | H | H | F | H |
| H | H | $OCF_2H$ | H | H | H | $OCH_3$ |
| H | H | $OCF_2H$ | H | H | Cl | H |
| H | H | $OCF_2H$ | H | H | $OCH_3$ | H |
| H | H | $OCH_2CH_2N(CH_3)_2$ | F | H | H | H |

TABLE 1-continued

| $R_1$ | $R_{11}$ | $R_{12}$ | $R_2$ | $R_3$ | $R_4$ | $R_5$ |
|---|---|---|---|---|---|---|
| H | H | $OCH_2CH_2N(CH_3)_2$ | H | $CH_3$ | H | H |
| H | H | $OCH_2CH_2N(CH_3)_2$ | H | F | H | H |
| H | H | $OCH_2CH_2N(CH_3)_2$ | H | H | F | H |
| H | H | $OCH_2CH_2N(CH_3)_2$ | H | H | H | $OCH_3$ |
| H | H | $OCH_2CH_2N(CH_3)_2$ | H | H | Cl | H |
| H | H | $OCH_2CH_2N(CH_3)_2$ | H | H | $OCH_3$ | H |
| $OCF_2H$ | H | H | H | H | H | H |
| $OCF_2H$ | H | H | H | $CH_3$ | H | H |
| $OCF_2H$ | H | H | H | F | H | H |
| $OCF_2H$ | H | H | H | H | F | H |
| $OCF_2H$ | H | H | H | H | H | $OCH_3$ |
| $OCF_2H$ | H | H | H | H | Cl | H |
| $OCF_2H$ | H | H | H | H | $OCH_3$ | H |
| $OCH_3$ | H | H | F | H | H | H |
| $OCH_3$ | H | H | H | $CH_3$ | H | H |
| $OCH_3$ | H | H | H | F | H | H |
| $OCH_3$ | H | H | H | H | F | H |
| $OCH_3$ | H | H | H | H | H | $OCH_3$ |
| $OCH_3$ | H | H | H | H | Cl | H |
| $OCH_3$ | H | H | H | H | $OCH_3$ | H |
| $CF_3$ | F | H | F | H | H | H |
| $CF_3$ | F | H | H | $CH_3$ | H | H |
| $CF_3$ | F | H | H | F | H | H |
| $CF_3$ | F | H | H | H | F | H |
| $CF_3$ | F | H | H | H | H | $OCH_3$ |
| $CF_3$ | F | H | H | H | Cl | H |
| $CF_3$ | H | H | H | H | $OCH_3$ | H |
| $CH_3$ | F | H | F | H | H | H |
| $CH_3$ | F | H | H | $CH_3$ | H | H |
| $CH_3$ | F | H | H | F | H | H |
| $CH_3$ | F | H | H | H | F | H |
| $CH_3$ | F | H | H | H | H | $OCH_3$ |
| $CH_3$ | H | H | H | H | Cl | H |
| $CH_3$ | F | H | H | H | $OCH_3$ | H |
| Cl | F | H | F | H | F | H |
| Cl | F | H | F | H | H | H |
| Cl | F | H | H | $CH_3$ | H | H |
| Cl | F | H | H | F | F | H |
| Cl | F | H | H | F | H | H |
| Cl | F | H | H | H | Cl | H |
| Cl | F | H | H | H | F | H |
| Cl | F | H | H | H | H | $OCF_2H$ |
| Cl | F | H | H | H | H | $OCH_3$ |
| Cl | F | H | F | H | H | H |
| F | F | H | F | H | H | H |
| F | F | H | H | $CH_3$ | H | H |
| F | F | H | H | F | H | H |
| F | F | H | H | H | F | H |
| F | F | H | H | H | H | $OCH_3$ |
| F | F | H | H | H | Cl | H |
| F | F | H | H | H | $OCH_3$ | H |
| H | F | $CF_3$ | F | H | H | H |
| H | F | $CF_3$ | H | $CH_3$ | H | H |
| H | F | $CF_3$ | H | F | H | H |
| H | F | $CF_3$ | H | H | F | H |
| H | F | $CF_3$ | H | H | H | $OCH_3$ |
| H | F | $CF_3$ | H | H | Cl | H |
| H | F | $CF_3$ | H | H | $OCH_3$ | H |
| H | F | CH | F | H | H | H |
| H | F | $CH_3$ | H | $CH_3$ | H | H |
| H | F | $CH_3$ | H | F | H | H |
| H | F | $CH_3$ | H | H | F | H |
| H | F | $CH_3$ | H | H | H | $OCH_3$ |
| H | F | $CH_3$ | H | H | Cl | H |
| H | F | $CH_3$ | H | H | $OCH_3$ | H |
| H | F | $OCF_2H$ | F | H | H | H |
| H | F | $OCF_2H$ | H | $CH_3$ | H | H |
| H | F | $OCF_2H$ | H | F | H | H |
| H | F | $OCF_2H$ | H | H | F | H |
| H | F | $OCF_2H$ | H | H | H | $OCH_3$ |
| H | F | $OCF_2H$ | H | H | Cl | H |
| H | F | $OCF_2H$ | H | H | $OCH_3$ | H |
| $OCF_2H$ | F | H | F | H | H | H |
| $OCF_2H$ | F | H | H | $CH_3$ | H | H |
| $OCF_2H$ | F | H | H | F | H | H |
| $OCF_2H$ | F | H | H | H | F | H |
| $OCF_2H$ | F | H | H | H | H | $OCH_3$ |
| $OCF_2H$ | F | H | H | H | Cl | H |

TABLE 1-continued

| $R_1$ | $R_{11}$ | $R_{12}$ | $R_2$ | $R_3$ | $R_4$ | $R_5$ |
|---|---|---|---|---|---|---|
| $OCF_2H$ | F | H | H | H | $OCH_3$ | H |
| $OCH_3$ | F | H | F | H | H | H |
| $OCH_3$ | F | H | H | $CH_3$ | H | H |
| $OCH_3$ | F | H | H | F | H | H |
| $OCH_3$ | F | H | H | H | F | H |
| $OCH_3$ | F | H | H | H | H | $OCH_3$ |
| $OCH_3$ | F | H | H | H | Cl | H |
| $OCH_3$ | F | H | H | H | $OCH_3$ | H |

Preferably, the compound of formula (Ib)

(Ib)

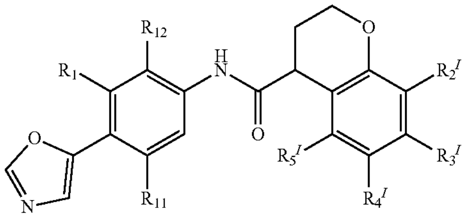

is selected from the group consisting of compounds of the formula (I), wherein $R_1$, $R_{11}$, $R_{12}$, $R_2^I$, $R_3^I$, $R_4^I$ and $R_5^I$ are as indicated in Table 2:

TABLE 2

| $R_1$ | $R_{11}$ | $R_{12}$ | $R_2^I$ | $R_3^I$ | $R_4^I$ | $R_5^I$ |
|---|---|---|---|---|---|---|
| $CF_3$ | H | H | F | H | H | H |
| $CF_3$ | H | H | H | $CH_3$ | H | H |
| $CF_3$ | H | H | H | F | H | H |
| $CF_3$ | H | H | H | H | F | H |
| $CF_3$ | H | H | H | H | H | $OCH_3$ |
| $CF_3$ | H | H | H | H | Cl | H |
| $CF_3$ | H | H | H | H | $OCH_3$ | H |
| $CH_3$ | H | H | F | H | H | H |
| $CH_3$ | H | H | H | $CH_3$ | H | H |
| $CH_3$ | H | H | H | F | H | H |
| $CH_3$ | H | H | H | H | F | H |
| $CH_3$ | H | H | H | H | H | $OCH_3$ |
| $CH_3$ | H | H | H | H | Cl | H |
| $CH_3$ | H | H | H | H | $OCH_3$ | H |
| Cl | H | H | F | H | F | H |
| Cl | H | H | F | H | H | H |
| Cl | H | H | H | $CH_3$ | H | H |
| Cl | H | H | H | F | F | H |
| Cl | H | H | H | F | H | H |
| Cl | H | H | H | H | Cl | H |
| Cl | H | H | H | H | F | H |
| Cl | H | H | H | H | H | $OCF_2H$ |
| Cl | H | H | H | H | H | $OCH_3$ |
| Cl | H | H | H | H | $OCF_2H$ | H |
| Cl | H | H | H | H | $OCH_3$ | H |
| F | H | H | F | H | H | H |
| F | H | H | H | $CH_3$ | H | H |
| F | H | H | H | F | H | H |
| F | H | H | H | H | F | H |
| F | H | H | H | H | H | $OCH_3$ |
| F | H | H | H | H | Cl | H |
| F | H | H | H | H | $OCH_3$ | H |
| H | H | $CF_3$ | F | H | H | H |
| H | H | $CF_3$ | H | $CH_3$ | H | H |
| H | H | $CF_3$ | H | F | H | H |
| H | H | $CF_3$ | H | H | F | H |
| H | H | $CF_3$ | H | H | H | $OCH_3$ |
| H | H | $CF_3$ | H | H | Cl | H |
| H | H | $CF_3$ | H | H | $OCH_3$ | H |
| H | H | $CH_3$ | F | H | H | H |
| H | H | $CH_3$ | H | $CH_3$ | H | H |
| H | H | $CH_3$ | H | F | H | H |

TABLE 2-continued

| $R_1$ | $R_{11}$ | $R_{12}$ | $R_2^I$ | $R_3^I$ | $R_4^I$ | $R_5^I$ |
|---|---|---|---|---|---|---|
| H | H | $CH_3$ | H | H | F | H |
| H | H | $CH_3$ | H | H | H | $OCH_3$ |
| H | H | $CH_3$ | H | H | Cl | H |
| H | H | $CH_3$ | H | H | $OCH_3$ | H |
| H | H | $OCF_2H$ | F | H | H | H |
| H | H | $OCF_2H$ | H | $CH_3$ | H | H |
| H | H | $OCF_2H$ | H | F | H | H |
| H | H | $OCF_2H$ | H | H | F | H |
| H | H | $OCF_2H$ | H | H | H | $OCH_3$ |
| H | H | $OCF_2H$ | H | H | Cl | H |
| H | H | $OCF_2H$ | H | H | $OCH_3$ | H |
| H | H | $OCH_2CH_2N(CH_3)_2$ | F | H | H | H |
| H | H | $OCH_2CH_2N(CH_3)_2$ | H | $CH_3$ | H | H |
| H | H | $OCH_2CH_2N(CH_3)_2$ | H | F | H | H |
| H | H | $OCH_2CH_2N(CH_3)_2$ | H | H | F | H |
| H | H | $OCH_2CH_2N(CH_3)_2$ | H | H | H | $OCH_3$ |
| H | H | $OCH_2CH_2N(CH_3)_2$ | H | H | Cl | H |
| H | H | $OCH_2CH_2N(CH_3)_2$ | H | H | $OCH_3$ | H |
| $OCF_2H$ | H | H | F | H | H | H |
| $OCF_2H$ | H | H | H | $CH_3$ | H | H |
| $OCF_2H$ | H | H | H | F | H | H |
| $OCF_2H$ | H | H | H | H | F | H |
| $OCF_2H$ | H | H | H | H | H | $OCH_3$ |
| $OCF_2H$ | H | H | H | H | Cl | H |
| $OCF_2H$ | H | H | H | H | $OCH_3$ | H |
| $OCH_3$ | H | H | F | H | H | H |
| $OCH_3$ | H | H | H | $CH_3$ | H | H |
| $OCH_3$ | H | H | H | F | H | H |
| $OCH_3$ | H | H | H | H | F | H |
| $OCH_3$ | H | H | H | H | H | $OCH_3$ |
| $OCH_3$ | H | H | H | H | Cl | H |
| $OCH_3$ | H | H | H | H | $OCH_3$ | H |
| $CF_3$ | F | H | F | H | H | H |
| $CF_3$ | F | H | H | $CH_3$ | H | H |
| $CF_3$ | F | H | H | F | H | H |
| $CF_3$ | F | H | H | H | F | H |
| $CF_3$ | F | H | H | H | H | $OCH_3$ |
| $CF_3$ | F | H | H | H | Cl | H |
| $CF_3$ | F | H | H | H | $OCH_3$ | H |
| $CH_3$ | F | H | F | H | H | H |
| $CH_3$ | F | H | H | $CH_3$ | H | H |
| $CH_3$ | F | H | H | F | H | H |
| $CH_3$ | F | H | H | H | F | H |
| $CH_3$ | F | H | H | H | H | $OCH_3$ |
| $CH_3$ | F | H | H | H | Cl | H |
| $CH_3$ | F | H | H | H | $OCH_3$ | H |
| Cl | F | H | F | H | F | H |
| Cl | F | H | F | H | H | H |
| Cl | F | H | H | $CH_3$ | H | H |
| Cl | F | H | H | F | F | H |
| Cl | F | H | H | F | H | H |
| Cl | F | H | H | H | Cl | H |
| Cl | F | H | H | H | F | H |
| Cl | F | H | H | H | H | $OCF_2H$ |
| Cl | F | H | H | H | H | $OCH_3$ |
| F | F | H | F | H | H | H |
| F | F | H | H | $CH_3$ | H | H |
| F | F | H | H | F | H | H |
| F | F | H | H | H | F | H |
| F | F | H | H | H | H | $OCH_3$ |
| F | F | H | H | H | Cl | H |
| F | F | H | H | H | $OCH_3$ | H |
| H | F | $CF_3$ | F | H | H | H |
| H | F | $CF_3$ | H | $CH_3$ | H | H |
| H | F | $CF_3$ | H | F | H | H |
| H | F | $CF_3$ | H | H | F | H |
| H | F | $CF_3$ | H | H | H | $OCH_3$ |
| H | F | $CF_3$ | H | H | Cl | H |
| H | F | $CF_3$ | H | H | $OCH_3$ | H |
| H | F | $CH_3$ | F | H | H | H |
| H | F | $CH_3$ | H | $CH_3$ | H | H |
| H | F | $CH_3$ | H | F | H | H |
| H | F | $CH_3$ | H | H | F | H |
| H | F | $CH_3$ | H | H | H | $OCH_3$ |
| H | F | $CH_3$ | H | H | Cl | H |
| H | F | $CH_3$ | H | H | $OCH_3$ | H |
| H | F | $OCF_2H$ | F | H | H | H |
| H | F | $OCF_2H$ | H | $CH_3$ | H | H |

TABLE 2-continued

| $R_1$ | $R_{11}$ | $R_{12}$ | $R_2^I$ | $R_3^I$ | $R_4^I$ | $R_5^I$ |
|---|---|---|---|---|---|---|
| H | F | $OCF_2H$ | H | F | H | H |
| H | F | $OCF_2H$ | H | H | F | H |
| H | F | $OCF_2H$ | H | H | H | $OCH_3$ |
| H | F | $OCF_2H$ | H | H | Cl | H |
| H | F | $OCF_2H$ | H | H | $OCH_3$ | H |
| $OCF_2H$ | F | H | F | H | H | H |
| $OCF_2H$ | F | H | H | $CH_3$ | H | H |
| $OCF_2H$ | F | H | H | F | H | H |
| $OCF_2H$ | F | H | H | H | F | H |
| $OCF_2H$ | F | H | H | H | H | $OCH_3$ |
| $OCF_2H$ | F | H | H | H | Cl | H |
| $OCF_2H$ | F | H | H | H | $OCH_3$ | H |
| $OCH_3$ | F | H | F | H | H | H |
| $OCH_3$ | F | H | H | $CH_3$ | H | H |
| $OCH_3$ | F | H | H | F | H | H |
| $OCH_3$ | F | H | H | H | F | H |
| $OCH_3$ | F | H | H | H | H | $OCH_3$ |
| $OCH_3$ | F | H | H | H | Cl | H |
| $OCH_3$ | F | H | H | H | $OCH_3$ | H |

Preferably, the compound of formula (Ic)

(Ic)

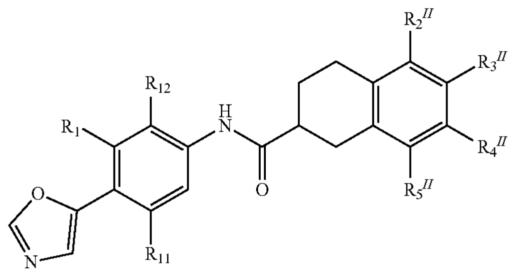

is selected from the group consisting of compounds of the formula (I), wherein $R_1$, $R_{11}$, $R_{12}$, $R_2^{II}$, $R_3^{II}$, $R_4^{II}$ and $R_5^{II}$ are as indicated in Table 3:

TABLE 3

| $R_1$ | $R_{11}$ | $R_{12}$ | $R_2^{II}$ | $R_3^{II}$ | $R_4^{II}$ | $R_5^{II}$ |
|---|---|---|---|---|---|---|
| $CF_3$ | H | H | F | H | H | H |
| $CF_3$ | H | H | H | $CH_3$ | H | H |
| $CF_3$ | H | H | H | F | H | H |
| $CF_3$ | H | H | H | H | F | H |
| $CF_3$ | H | H | H | H | H | $OCH_3$ |
| $CF_3$ | H | H | H | H | Cl | H |
| $CF_3$ | H | H | H | H | $OCH_3$ | H |
| $CH_3$ | H | H | F | H | H | H |
| $CH_3$ | H | H | H | $CH_3$ | H | H |
| $CH_3$ | H | H | H | F | H | H |
| $CH_3$ | H | H | H | H | F | H |
| $CH_3$ | H | H | H | H | H | $OCH_3$ |
| $CH_3$ | H | H | H | H | Cl | H |
| $CH_3$ | H | H | H | H | $OCH_3$ | H |
| Cl | H | H | F | H | F | H |
| Cl | H | H | F | H | H | H |
| Cl | H | H | H | $CH_3$ | H | H |
| Cl | H | H | H | F | F | H |
| Cl | H | H | H | F | H | H |
| Cl] | H | H | H | H | Cl | H |
| Cl | H | H | H | H | F | H |
| Cl] | H | H | H | H | H | $OCF_2H$ |
| Cl | H | H | H | H | H | $OCH_3$ |
| Cl | H | H | H | H | $OCF_2H$ | H |
| Cl | H | H | H | $OCH_3$ | H | H |
| F | H | H | F | H | H | H |
| F | H | H | H | $CH_3$ | H | H |
| F | H | H | H | F | H | H |
| F | H | H | H | H | F | H |

TABLE 3-continued

| $R_1$ | $R_{11}$ | $R_{12}$ | $R_2^{II}$ | $R_3^{II}$ | $R_4^{II}$ | $R_5^{II}$ |
|---|---|---|---|---|---|---|
| F | H | H | H | H | H | $OCH_3$ |
| F | H | H | H | H | Cl | H |
| F | H | H | H | H | $OCH_3$ | H |
| H | H | $CF_3$ | F | H | H | H |
| H | H | $CF_3$ | H | $CH_3$ | H | H |
| H | H | $CF_3$ | H | F | H | H |
| H | H | $CF_3$ | H | H | F | H |
| H | H | $CF_3$ | H | H | H | $OCH_3$ |
| H | H | CF | H | H | Cl | H |
| H | H | $CF_3$ | H | H | $OCH_3$ | H |
| H | H | $CH_3$ | F | H | H | H |
| H | H | $CH_3$ | H | $CH_3$ | H | H |
| H | H | $CH_3$ | H | F | H | H |
| H | H | $CH_3$ | H | H | F | H |
| H | H | $CH_3$ | H | H | H | $OCH_3$ |
| H | H | $CH_3$ | H | H | Cl | H |
| H | H | $CH_3$ | H | H | $OCH_3$ | H |
| H | H | $OCF_2H$ | F | H | H | H |
| H | H | $OCF_2H$ | H | $CH_3$ | H | H |
| H | H | $OCF_2H$ | H | F | H | H |
| H | H | $OCF_2H$ | H | H | F | H |
| H | H | $OCF_2H$ | H | H | H | $OCH_3$ |
| H | H | $OCF_2H$ | H | H | Cl | H |
| H | H | $OCF_2H$ | H | H | $OCH_3$ | H |
| H | H | $OCH_2CH_2N(CH_3)_2$ | F | H | H | H |
| H | H | $OCH_2CH_2N(CH_3)_2$ | H | $CH_3$ | H | H |
| H | H | $OCH_2CH_2N(CH_3)_2$ | H | F | H | H |
| H | H | $OCH_2CH_2N(CH_3)_2$ | H | H | F | H |
| H | H | $OCH_2CH_2N(CH_3)_2$ | H | H | H | $OCH_3$ |
| H | H | $OCH_2CH_2N(CH_3)_2$ | H | H | Cl | H |
| H | H | $OCH_2CH_2N(CH_3)_2$ | H | H | $OCH_3$ | H |
| $OCF_2H$ | H | H | F | H | H | H |
| $OCF_2H$ | H | H | H | $CH_3$ | H | H |
| $OCF_2H$ | H | H | H | F | H | H |
| $OCF_2H$ | H | H | H | H | F | H |
| $OCF_2H$ | H | H | H | H | H | $OCH_3$ |
| $OCF_2H$ | H | H | H | H | Cl | H |
| $OCF_2H$ | H | H | H | H | $OCH_3$ | H |
| $OCH_3$ | H | H | F | H | H | H |
| $OCH_3$ | H | H | H | $CH_3$ | H | H |
| $OCH_3$ | H | H | H | F | H | H |
| $OCH_3$ | H | H | H | H | F | H |
| $OCH_3$ | H | H | H | H | H | $OCH_3$ |
| $OCH_3$ | H | H | H | H | Cl | H |
| $OCH_3$ | H | H | H | H | $OCH_3$ | H |
| $CF_3$ | F | H | F | H | H | H |
| $CF_3$ | F | H | H | $CH_3$ | H | H |
| $CF_3$ | F | H | H | F | H | H |
| $CF_3$ | F | H | H | H | F | H |
| $CF_3$ | F | H | H | H | H | $OCH_3$ |
| $CF_3$ | F | H | H | H | Cl | H |
| $CF_3$ | F | H | H | H | $OCH_3$ | H |
| $CH_3$ | F | H | F | H | H | H |
| $CH_3$ | F | H | H | $CH_3$ | H | H |
| $CH_3$ | F | H | H | F | H | H |
| $CH_3$ | F | H | H | H | F | H |
| $CH_3$ | F | H | H | H | H | $OCH_3$ |
| $CH_3$ | F | H | H | H | Cl | H |
| $CH_3$ | F | H | H | H | $OCH_3$ | H |
| Cl | F | H | F | H | F | H |
| Cl | F | H | F | H | H | H |
| Cl | F | H | H | $CH_3$ | H | H |
| Cl | F | H | H | F | F | H |
| Cl | F | H | H | F | H | H |
| Cl | F | H | H | H | Cl | H |
| Cl | F | H | H | H | F | H |
| Cl | F | H | H | H | H | $OCF_2H$ |
| Cl | F | H | H | H | H | $OCH_3$ |
| F | F | H | F | H | H | H |
| F | F | H | H | $CH_3$ | H | H |
| F | F | H | H | F | H | H |
| F | F | H | H | H | F | H |
| F | F | H | H | H | H | $OCH_3$ |
| F | F | H | H | H | Cl | H |
| F | F | H | H | H | $OCH_3$ | H |
| H | F | $CF_3$ | F | H | H | H |
| H | F | $CF_3$ | H | $CH_3$ | H | H |
| H | F | $CF_3$ | H | F | H | H |

TABLE 3-continued

| $R_1$ | $R_{11}$ | $R_{12}$ | $R_2^{II}$ | $R_3^{II}$ | $R_4^{II}$ | $R_5^{II}$ |
|---|---|---|---|---|---|---|
| H | F | $CF_3$ | H | H | F | H |
| H | F | $CF_3$ | H | H | H | $OCH_3$ |
| H | F | $CF_3$ | H | H | Cl | H |
| H | F | $CF_3$ | H | H | $OCH_3$ | H |
| H | F | $CH_3$ | F | H | H | H |
| H | F | $CH_3$ | H | $CH_3$ | H | H |
| H | F | $CH_3$ | H | F | H | H |
| H | F | $CH_3$ | H | H | F | H |
| H | F | $CH_3$ | H | H | H | $OCH_3$ |
| H | F | $CH_3$ | H | H | Cl | H |
| H | F | $CH_3$ | H | H | $OCH_3$ | H |
| H | F | $OCF_2H$ | F | H | H | H |
| H | F | $OCF_2H$ | H | $CH_3$ | H | H |
| H | F | $OCF_2H$ | H | F | H | H |
| H | F | $OCF_2H$ | H | H | F | H |
| H | F | $OCF_2H$ | H | H | H | $OCH_3$ |
| H | F | $OCF_2H$ | H | H | Cl | H |
| H | F | $OCF_2H$ | H | H | $OCH_3$ | H |
| $OCF_2H$ | F | H | F | H | H | H |
| $OCF_2H$ | F | H | H | $CH_3$ | H | H |
| $OCF_2H$ | F | H | H | F | H | H |
| $OCF_2H$ | F | H | H | H | F | H |
| $OCF_2H$ | F | H | H | H | H | $OCH_3$ |
| $OCF_2H$ | F | H | H | H | Cl | H |
| $OCF_2H$ | F | H | H | H | $OCH_3$ | H |
| $OCH_3$ | F | H | F | H | H | H |
| $OCH_3$ | F | H | H | $CH_3$ | H | H |
| $OCH_3$ | F | H | H | F | H | H |
| $OCH_3$ | F | H | H | H | F | H |
| $OCH_3$ | F | H | H | H | H | $OCH_3$ |
| $OCH_3$ | F | H | H | H | Cl | H |
| $OCH_3$ | F | H | H | H | $OCH_3$ | H |

Preferably, the compound of formula (Id)

(Id)

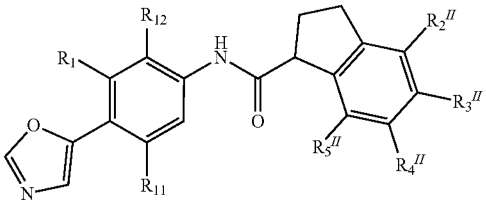

is selected from the group consisting of compounds of the formula (I), wherein A, $R_1$, $R_{12}$, $R_2^{III}$, $R_3^{III}$, $R_4^{III}$ and $R_5^{III}$ are as indicated in Table 4:

TABLE 4

| $R_1$ | $R_{11}$ | $R_{12}$ | $R_2^{III}$ | $R_3^{III}$ | $R_4^{III}$ | $R_5^{III}$ |
|---|---|---|---|---|---|---|
| $CF_3$ | H | H | F | H | H | H |
| $CF_3$ | H | H | H | $CH_3$ | H | H |
| $CF_3$ | H | H | H | F | H | H |
| $CF_3$ | H | H | H | H | F | H |
| $CF_3$ | H | H | H | H | H | $OCH_3$ |
| $CF_3$ | H | H | H | H | Cl | H |
| $CF_3$ | H | H | H | H | $OCH_3$ | H |
| $CH_3$ | H | H | F | H | H | H |
| $CH_3$ | H | H | H | $CH_3$ | H | H |
| $CH_3$ | H | H | H | F | H | H |
| $CH_3$ | H | H | H | H | F | H |
| $CH_3$ | H | H | H | H | H | $OCH_3$ |
| $CH_3$ | H | H | H | H | Cl | H |
| $CH_3$ | H | H | H | H | $OCH_3$ | H |
| Cl | H | H | F | H | F | H |
| Cl | H | H | F | H | H | H |
| Cl | H | H | H | $CH_3$ | H | H |
| Cl | H | H | H | H | F | H |

TABLE 4-continued

| $R_1$ | $R_{11}$ | $R_{12}$ | $R_2^{III}$ | $R_3^{III}$ | $R_4^{III}$ | $R_5^{III}$ |
|---|---|---|---|---|---|---|
| Cl | H | H | H | F | H | H |
| Cl | H | H | H | H | Cl | H |
| Cl | H | H | H | H | F | H |
| Cl | H | H | H | H | H | $OCF_2H$ |
| Cl | H | H | H | H | H | $OCH_3$ |
| Cl | H | H | H | H | $OCF_2H$ | H |
| Cl | H | H | H | H | $OCH_3$ | H |
| F | H | H | F | H | H | H |
| F | H | H | H | $CH_3$ | H | H |
| F | H | H | H | F | H | H |
| F | H | H | H | H | F | H |
| F | H | H | H | H | H | $OCH_3$ |
| F | H | H | H | H | Cl | H |
| H | H | H | H | H | $OCH_3$ | H |
| H | H | $CF_3$ | F | H | H | H |
| H | H | $CF_3$ | H | $CH_3$ | H | H |
| H | H | $CF_3$ | H | F | H | H |
| H | H | $CF_3$ | H | H | F | H |
| H | H | $CF_3$ | H | H | H | $OCH_3$ |
| H | H | $CF_3$ | H | H | Cl | H |
| H | H | $CF_3$ | H | H | $OCH_3$ | H |
| H | H | $CH_3$ | F | H | H | H |
| H | H | $CH_3$ | H | $CH_3$ | H | H |
| H | H | $CH_3$ | H | F | H | H |
| H | H | $CH_3$ | H | H | F | H |
| H | H | $CH_3$ | H | H | H | $OCH_3$ |
| H | H | $CH_3$ | H | H | Cl | H |
| H | H | $CH_3$ | H | H | $OCH_3$ | H |
| H | H | $OCF_2H$ | F | H | H | H |
| H | H | $OCF_2H$ | H | $CH_3$ | H | H |
| H | H | $OCF_2H$ | H | F | H | H |
| H | H | $OCF_2H$ | H | H | F | H |
| H | H | $OCF_2H$ | H | H | H | $OCH_3$ |
| H | H | $OCF_2H$ | H | H | Cl | H |
| H | H | $OCF_2H$ | H | H | $OCH_3$ | H |
| H | H | $OCH_2CH_2N(CH_3)_2$ | F | H | H | H |
| H | H | $OCH_2CH_2N(CH_3)_2$ | H | $CH_3$ | H | H |
| H | H | $OCH_2CH_2N(CH_3)_2$ | H | F | H | H |
| H | H | $OCH_2CH_2N(CH_3)_2$ | H | H | H | H |
| H | H | $OCH_2CH_2N(CH_3)_2$ | H | H | H | $OCH_3$ |
| H | H | $OCH_2CH_2N(CH_3)_2$ | H | H | Cl | H |
| H | H | $OCH_2CH_2N(CH_3)_2$ | H | H | $OCH_3$ | H |
| $OCF_2H$ | H | H | F | H | H | H |
| $OCF_2H$ | H | H | H | $CH_3$ | H | H |
| $OCF_2H$ | H | H | H | F | H | H |
| $OCF_2H$ | H | H | H | H | F | H |
| $OCF_2H$ | H | H | H | H | H | $OCH_3$ |
| $OCF_2H$ | H | H | H | H | Cl | H |
| $OCF_2H$ | H | H | H | H | $OCH_3$ | H |
| $OCH_3$ | H | H | F | H | H | H |
| $OCH_3$ | H | H | H | $CH_3$ | H | H |
| $OCH_3$ | H | H | H | F | H | H |
| $OCH_3$ | H | H | H | H | F | H |
| $OCH_3$ | H | H | H | H | H | $OCH_3$ |
| $OCH_3$ | H | H | H | H | Cl | H |
| $OCH_3$ | H | H | H | H | $OCH_3$ | H |
| $CF_3$ | F | H | F | H | H | H |
| $CF_3$ | F | H | H | $CH_3$ | H | H |
| $CF_3$ | F | H | H | F | H | H |
| $CF_3$ | F | H | H | H | F | H |
| $CF_3$ | F | H | H | H | H | $OCH_3$ |
| $CF_3$ | F | H | H | H | Cl | H |
| $CF_3$ | F | H | H | H | $OCH_3$ | H |
| $CH_3$ | F | H | F | H | H | H |
| $CH_3$ | F | H | H | $CH_3$ | H | H |
| $CH_3$ | F | H | H | F | H | H |
| $CH_3$ | F | H | H | H | F | H |
| $CH_3$ | F | H | H | H | H | $OCH_3$ |
| $CH_3$ | F | H | H | H | Cl | H |
| $CH_3$ | F | H | H | H | $OCH_3$ | H |
| Cl | F | H | F | H | F | H |
| Cl | F | H | F | H | H | H |
| Cl | F | H | H | CH | H | H |
| Cl | F | H | H | F | F | H |
| Cl | F | H | H | F | H | H |
| Cl | F | H | H | H | Cl | H |
| Cl | F | H | H | H | F | H |
| Cl | F | H | H | H | H | $OCF_2H$ |

TABLE 4-continued

| $R_1$ | $R_{11}$ | $R_{12}$ | $R_2^{III}$ | $R_3^{III}$ | $R_4^{III}$ | $R_5^{III}$ |
|---|---|---|---|---|---|---|
| Cl | F | H | H | H | H | $OCH_3$ |
| F | F | H | F | H | H | H |
| F | F | H | H | $CH_3$ | H | H |
| F | F | H | H | F | H | H |
| F | F | H | H | H | F | H |
| F | F | H | H | H | H | $OCH_3$ |
| F | F | H | H | H | Cl | H |
| F | F | H | H | H | $OCH_3$ | H |
| H | F | $CF_3$ | F | H | H | H |
| H | F | $CF_3$ | H | $CH_3$ | H | H |
| H | F | $CF_3$ | H | F | H | H |
| H | F | $CF_3$ | H | H | F | H |
| H | F | $CF_3$ | H | H | H | $OCH_3$ |
| H | F | $CF_3$ | H | H | Cl | H |
| H | F | $CF_3$ | H | H | $OCH_3$ | H |
| H | F | $CH_3$ | F | H | H | H |
| H | F | $CH_3$ | H | $CH_3$ | H | H |
| H | F | $CH_3$ | H | F | H | H |
| H | F | $CH_3$ | H | H | F | H |
| H | F | $CH_3$ | H | H | H | $OCH_3$ |
| H | F | $CH_3$ | H | H | Cl | H |
| H | F | $CH_3$ | H | H | $OCH_3$ | H |
| H | F | $OCF_2H$ | F | H | H | H |
| H | F | $OCF_2H$ | H | $CH_3$ | H | H |
| H | F | $OCF_2H$ | H | F | H | H |
| H | F | $OCF_2H$ | H | H | F | H |
| H | F | $OCF_2H$ | H | H | H | $OCH_3$ |
| H | F | $OCF_2H$ | H | H | Cl | H |
| H | F | $OCF_2H$ | H | H | $OCH_3$ | H |
| $OCF_2H$ | F | H | F | H | H | H |
| $OCF_2H$ | F | H | H | $CH_3$ | H | H |
| $OCF_2H$ | F | H | H | F | H | H |
| $OCF_2H$ | F | H | H | H | F | H |
| $OCF_2H$ | F | H | H | H | H | $OCH_3$ |
| $OCF_2H$ | F | H | H | H | Cl | H |
| $OCF_2H$ | F | H | H | H | $OCH_3$ | H |
| $OCH_3$ | F | H | F | H | H | H |
| $OCH_3$ | F | H | H | $CH_3$ | H | H |
| $OCH_3$ | F | H | H | F | H | H |
| $OCH_3$ | F | H | H | H | F | H |
| $OCH_3$ | F | H | H | H | H | $OCH_3$ |
| $OCH_3$ | F | H | H | H | Cl | H |
| $OCH_3$ | F | H | H | H | $OCH_3$ | H |

Preferably, the compound of formula (Ie)

(Ie)

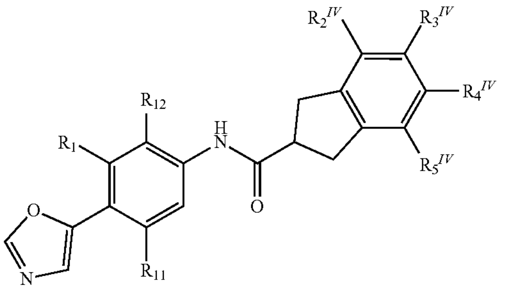

is selected from the group consisting of compounds of the formula (I), wherein $R_1$, $R_{11}$, $R_{12}$, $R_2^{IV}$, $R_3^{IV}$, $R_4^{IV}$ and $R_5^{IV}$ are as indicated in Table 5:

TABLE 5

| $R_1$ | $R_{11}$ | $R_{12}$ | $R_2^{IV}$ | $R_3^{IV}$ | $R_4^{IV}$ | $R_5^{IV}$ |
|---|---|---|---|---|---|---|
| $CF_3$ | H | H | F | H | H | H |
| $CF_3$ | H | H | H | $CH_3$ | H | H |
| $CF_3$ | H | H | H | F | H | H |
| $CF_3$ | H | H | H | H | F | H |

TABLE 5-continued

| $R_1$ | $R_{11}$ | $R_{12}$ | $R_2^{IV}$ | $R_3^{IV}$ | $R_4^{IV}$ | $R_5^{IV}$ |
|---|---|---|---|---|---|---|
| $CF_3$ | H | H | H | H | H | $OCH_3$ |
| $CF_3$ | H | H | H | H | Cl | H |
| $CF_3$ | H | H | H | H | $OCH_3$ | H |
| $CH_3$ | H | H | F | H | H | H |
| $CH_3$ | H | H | H | $CH_3$ | H | H |
| $CH_3$ | H | H | H | F | H | H |
| $CH_3$ | H | H | H | H | F | H |
| $CH_3$ | H | H | H | H | H | $OCH_3$ |
| $CH_3$ | H | H | H | H | Cl | H |
| $CH_3$ | H | H | H | H | $OCH_3$ | H |
| Cl | H | H | F | H | F | H |
| Cl | H | H | F | H | H | H |
| Cl | H | H | H | $CH_3$ | H | H |
| Cl | H | H | H | F | F | H |
| Cl | H | H | H | F | H | H |
| Cl | H | H | H | H | Cl | H |
| Cl | H | H | H | H | F | H |
| Cl | H | H | H | H | H | $OCF_2H$ |
| Cl | H | H | H | H | H | $OCH_3$ |
| Cl | H | H | H | H | $OCF_2H$ | H |
| Cl | H | H | H | H | $OCH_3$ | H |
| F | H | H | F | H | H | H |
| F | H | H | H | $CH_3$ | H | H |
| F | H | H | H | F | H | H |
| F | H | H | H | H | F | H |
| F | H | H | H | H | H | $OCH_3$ |
| F | H | H | H | H | Cl | H |
| F | H | H | H | H | $OCH_3$ | H |
| H | H | $CF_3$ | F | H | H | H |
| H | H | $CF_3$ | H | $CH_3$ | H | H |
| H | H | $CF_3$ | H | F | H | H |
| H | H | $CF_3$ | H | H | F | H |
| H | H | $CF_3$ | H | H | H | $OCH_3$ |
| H | H | $CF_3$ | H | H | Cl | H |
| H | H | $CF_3$ | H | H | $OCH_3$ | H |
| H | H | $CH_3$ | F | H | H | H |
| H | H | $CH_3$ | H | $CH_3$ | H | H |
| H | H | $CH_3$ | H | F | H | H |
| H | H | $CH_3$ | H | H | F | H |
| H | H | $CH_3$ | H | H | H | $OCH_3$ |
| H | H | $CH_3$ | H | H | Cl | H |
| H | H | $CH_3$ | H | H | $OCH_3$ | H |
| H | H | $OCF_2H$ | F | H | H | H |
| H | H | $OCF_2H$ | H | $CH_3$ | H | H |
| H | H | $OCF_2H$ | H | F | H | H |
| H | H | $OCF_2H$ | H | H | F | H |
| H | H | $OCF_2H$ | H | H | H | $OCH_3$ |
| H | H | $OCF_2H$ | H | H | Cl | H |
| H | H | $OCF_2H$ | H | H | $OCH_3$ | H |
| H | H | $OCH_2CH_2N(CH_3)_2$ | F | H | H | H |
| H | H | $OCH_2CH_2N(CH_3)_2$ | H | $CH_3$ | H | H |
| H | H | $OCH_2CH_2N(CH_3)_2$ | H | F | H | H |
| H | H | $OCH_2CH_2N(CH_3)_2$ | H | H | F | H |
| H | H | $OCH_2CH_2N(CH_3)_2$ | H | H | H | $OCH_3$ |
| H | H | $OCH_2CH_2N(CH_3)_2$ | H | H | Cl | H |
| H | H | $OCH_2CH_2N(CH_3)_2$ | H | H | $OCH_3$ | H |
| $OCF_2H$ | H | H | F | H | H | H |
| $OCF_2H$ | H | H | H | $CH_3$ | H | H |
| $OCF_2H$ | H | H | H | F | H | H |
| $OCF_2H$ | H | H | H | H | F | H |
| $OCF_2H$ | H | H | H | H | H | $OCH_3$ |
| $OCF_2H$ | H | H | H | H | Cl | H |
| $OCF_2H$ | H | H | H | H | $OCH_3$ | H |
| $OCH_3$ | H | H | F | H | H | H |
| $OCH_3$ | H | H | H | $CH_3$ | H | H |
| $OCH_3$ | H | H | H | F | H | H |
| $OCH_3$ | H | H | H | H | F | H |
| $OCH_3$ | H | H | H | H | H | $OCH_3$ |
| $OCH_3$ | H | H | H | H | Cl | H |
| $OCH_3$ | H | H | H | H | $OCH_3$ | H |
| $CF_3$ | F | H | F | H | H | H |
| $CF_3$ | F | H | H | $CH_3$ | H | H |
| $CF_3$ | F | H | H | F | H | H |
| $CF_3$ | F | H | H | H | F | H |
| $CF_3$ | F | H | H | H | H | $OCH_3$ |
| $CF_3$ | F | H | H | H | Cl | H |
| $CF_3$ | F | H | H | H | $OCH_3$ | H |
| $CH_3$ | F | H | F | H | H | H |

TABLE 5-continued

| $R_1$ | $R_{11}$ | $R_{12}$ | $R_2^{IV}$ | $R_3^{IV}$ | $R_4^{IV}$ | $R_5^{IV}$ |
|---|---|---|---|---|---|---|
| $CH_3$ | F | H | H | $CH_3$ | H | H |
| $CH_3$ | F | H | H | F | H | H |
| $CH_3$ | F | H | H | H | F | H |
| $CH_3$ | F | H | H | H | H | $OCH_3$ |
| $CH_3$ | F | H | H | H | Cl | H |
| $CH_3$ | F | H | H | H | $OCH_3$ | H |
| Cl | F | H | F | H | F | H |
| Cl | F | H | F | H | H | H |
| Cl | F | H | H | $CH_3$ | H | H |
| Cl | F | H | H | F | F | H |
| Cl | F | H | H | F | H | H |
| Cl | F | H | H | H | Cl | H |
| Cl | F | H | H | H | F | H |
| Cl | F | H | H | H | H | $OCF_2H$ |
| Cl | F | H | H | H | H | $OCH_3$ |
| F | F | H | F | H | H | H |
| F | F | H | H | $CH_3$ | H | H |
| F | F | H | H | F | H | H |
| F | F | H | H | H | F | H |
| F | F | H | H | H | H | $OCH_3$ |
| F | F | H | H | H | Cl | H |
| F | F | H | H | H | $OCH_3$ | H |
| H | F | $CF_3$ | F | H | H | H |
| H | F | $CF_3$ | H | $CH_3$ | H | H |
| H | F | $CF_3$ | H | F | H | H |
| H | F | $CF_3$ | H | H | F | H |
| H | F | $CF_3$ | H | H | H | $OCH_3$ |
| H | F | $CF_3$ | H | H | Cl | H |
| H | F | $CF_3$ | H | H | $OCH_3$ | H |
| H | F | $CH_3$ | F | H | H | H |
| H | F | $CH_3$ | H | $CH_3$ | H | H |
| H | F | $CH_3$ | H | F | H | H |
| H | F | $CH_3$ | H | H | F | H |
| H | F | $CH_3$ | H | H | H | $OCH_3$ |
| H | F | $CH_3$ | H | H | Cl | H |
| H | F | $CH_3$ | H | H | $OCH_3$ | H |
| H | F | $OCF_2H$ | F | H | H | H |
| H | F | $OCF_2H$ | H | $CH_3$ | H | H |
| H | F | $OCF_2H$ | H | F | H | H |
| H | F | $OCF_2H$ | H | H | F | H |
| H | F | $OCF_2H$ | H | H | H | $OCH_3$ |
| H | F | $OCF_2H$ | H | H | Cl | H |
| H | F | $OCF_2H$ | H | H | $OCH_3$ | H |
| $OCF_2H$ | F | H | F | H | H | H |
| $OCF_2H$ | F | H | H | $CH_3$ | H | H |
| $OCF_2H$ | F | H | H | F | H | H |
| $OCF_2H$ | F | H | H | H | F | H |
| $OCF_2H$ | F | H | H | H | H | $OCH_3$ |
| $OCF_2H$ | F | H | H | H | Cl | H |
| $OCF_2H$ | F | H | H | H | $OCH_3$ | H |
| $OCH_3$ | F | H | F | H | H | H |
| $OCH_3$ | F | H | H | $CH_3$ | H | H |
| $OCH_3$ | F | H | H | F | H | H |
| $OCH_3$ | F | H | H | H | F | H |
| $OCH_3$ | F | H | H | H | H | $OCH_3$ |
| $OCH_3$ | F | H | H | H | Cl | H |
| $OCH_3$ | F | H | H | H | $OCH_3$ | H |

Preferably, the compound of formula (If)

(If)

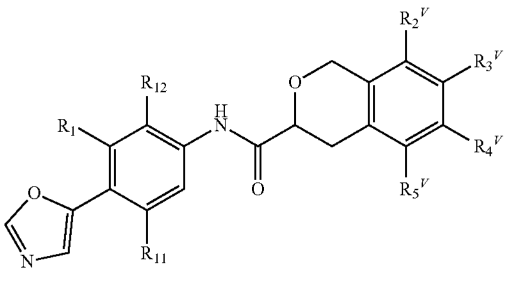

is selected from the group consisting of compounds of the formula (I), wherein $R_1$, $R_{11}$, $R_{12}$, $R_2^V$, $R_3^V$, $R_4^V$ and $R_5^V$ are as indicated in Table 6:

TABLE 6

| $R_1$ | $R_{11}$ | $R_{12}$ | $R_2^V$ | $R_3^V$ | $R_4^V$ | $R_5^V$ |
|---|---|---|---|---|---|---|
| $CF_3$ | H | H | F | H | H | H |
| $CF_3$ | H | H | H | $CH_3$ | H | H |
| $CF_3$ | H | H | H | F | H | H |
| $CF_3$ | H | H | H | H | F | H |
| $CF_3$ | H | H | H | H | H | $OCH_3$ |
| $CF_3$ | H | H | H | H | Cl | H |
| $CF_3$ | H | H | H | H | $OCH_3$ | H |
| $CH_3$ | H | H | F | H | H | H |
| $CH_3$ | H | H | H | $CH_3$ | H | H |
| $CH_3$ | H | H | H | F | H | H |
| $CH_3$ | H | H | H | H | F | H |
| $CH_3$ | H | H | H | H | H | $OCH_3$ |
| $CH_3$ | H | H | H | H | Cl | H |
| $CH_3$ | H | H | H | H | $OCH_3$ | H |
| Cl | H | H | F | H | F | H |
| Cl | H | H | F | H | H | H |
| Cl | H | H | H | $CH_3$ | H | H |
| Cl | H | H | H | F | F | H |
| Cl | H | H | H | F | H | H |
| Cl | H | H | H | H | Cl | H |
| Cl | H | H | H | H | F | H |
| Cl | H | H | H | H | H | $OCF_2H$ |
| Cl | H | H | H | H | H | $OCH_3$ |
| Cl | H | H | H | H | $OCF_2H$ | H |
| Cl | H | H | H | H | $OCH_3$ | H |
| F | H | H | F | H | H | H |
| F | H | H | H | $CH_3$ | H | H |
| F | H | H | H | F | H | H |
| F | H | H | H | H | F | H |
| F | H | H | H | H | H | $OCH_3$ |
| F | H | H | H | H | Cl | H |
| F | H | H | H | H | $OCH_3$ | H |
| H | H | $CF_3$ | F | H | H | H |
| H | H | $CF_3$ | H | $CH_3$ | H | H |
| H | H | $CF_3$ | H | H | H | H |
| H | H | $CF_3$ | H | H | F | H |
| H | H | $CF_3$ | H | H | H | $OCH_3$ |
| H | H | $CF_3$ | H | H | Cl | H |
| H | H | $CF_3$ | H | H | $OCH_3$ | H |
| H | H | $CH_3$ | F | H | H | H |
| H | H | $CH_3$ | H | $CH_3$ | H | H |
| H | H | $CH_3$ | H | F | H | H |
| H | H | $CH_3$ | H | H | F | H |
| H | H | $CH_3$ | H | H | H | $OCH_3$ |
| H | H | $CH_3$ | H | H | Cl | H |
| H | H | $CH_3$ | H | H | $OCH_3$ | H |
| H | H | $OCF_2H$ | F | H | H | H |
| H | H | $OCF_2H$ | H | $CH_3$ | H | H |
| H | H | $OCF_2H$ | H | F | H | H |
| H | H | $OCF_2H$ | H | H | F | H |
| H | H | $OCF_2H$ | H | H | H | $OCH_3$ |
| H | H | $OCF_2H$ | H | H | Cl | H |
| H | H | $OCF_2H$ | H | H | $OCH_3$ | H |
| H | H | $OCH_2CH_2N(CH_3)_2$ | F | H | H | H |
| H | H | $OCH_2CH_2N(CH_3)_2$ | H | $CH_3$ | H | H |
| H | H | $OCH_2CH_2N(CH_3)_2$ | H | F | H | H |
| H | H | $OCH_2CH_2N(CH_3)_2$ | H | H | F | H |
| H | H | $OCH_2CH_2N(CH_3)_2$ | H | H | H | $OCH_3$ |
| H | H | $OCH_2CH_2N(CH_3)_2$ | H | H | Cl | H |
| H | H | $OCH_2CH_2N(CH_3)_2$ | H | H | $OCH_3$ | H |
| $OCF_2H$ | H | H | F | H | H | H |
| $OCF_2H$ | H | H | H | $CH_3$ | H | H |
| $OCF_2H$ | H | H | H | F | H | H |
| $OCF_2H$ | H | H | H | H | F | H |
| $OCF_2H$ | H | H | H | H | H | $OCH_3$ |
| $OCF_2H$ | H | H | H | H | Cl | H |
| $OCF_2H$ | H | H | H | H | $OCH_3$ | H |
| $OCH_3$ | H | H | F | H | H | H |
| $OCH_3$ | H | H | H | $CH_3$ | H | H |
| $OCH_3$ | H | H | H | F | H | H |
| $OCH_3$ | H | H | H | H | F | H |
| $OCH_3$ | H | H | H | H | H | $OCH_3$ |
| $OCH_3$ | H | H | H | H | Cl | H |

TABLE 6-continued

| $R_1$ | $R_{11}$ | $R_{12}$ | $R_2^V$ | $R_3^V$ | $R_4^V$ | $R_5^V$ |
|---|---|---|---|---|---|---|
| $OCH_3$ | H | H | H | H | $OCH_3$ | H |
| $CF_3$ | F | H | F | H | H | H |
| $CF_3$ | F | H | H | $CH_3$ | H | H |
| $CF_3$ | F | H | H | F | H | H |
| $CF_3$ | F | H | H | H | F | H |
| $CF_3$ | F | H | H | H | H | $OCH_3$ |
| $CF_3$ | F | H | H | H | Cl | H |
| $CF_3$ | F | H | H | H | $OCH_3$ | H |
| $CH_3$ | F | H | F | H | H | H |
| $CH_3$ | F | H | H | $CH_3$ | H | H |
| $CH_3$ | F | H | H | F | H | H |
| $CH_3$ | F | H | H | H | F | H |
| $CH_3$ | F | H | H | H | H | $OCH_3$ |
| $CH_3$ | F | H | H | H | Cl | H |
| $CH_3$ | F | H | H | H | $OCH_3$ | H |
| Cl | F | H | F | H | F | H |
| Cl | F | H | F | H | H | H |
| Cl | F | H | H | $CH_3$ | H | H |
| Cl | F | H | H | F | F | H |
| Cl | F | H | H | F | H | H |
| Cl | F | H | H | H | Cl | H |
| Cl | F | H | H | H | F | H |
| Cl | F | H | H | H | H | $OCF_2H$ |
| Cl | F | H | H | H | H | $OCH_3$ |
| F | F | H | F | H | H | H |
| F | F | H | H | $CH_3$ | H | H |
| F | F | H | H | F | H | H |
| F | F | H | H | H | F | H |
| F | F | H | H | H | H | $OCH_3$ |
| F | F | H | H | H | Cl | H |
| F | F | H | H | H | $OCH_3$ | H |
| H | F | $CF_3$ | F | H | H | H |
| H | F | $CF_3$ | H | $CH_3$ | H | H |
| H | F | $CF_3$ | H | F | H | H |
| H | F | $CF_3$ | H | H | F | H |
| H | F | $CF_3$ | H | H | H | $OCH_3$ |
| H | F | $CF_3$ | H | H | Cl | H |
| H | F | $CF_3$ | H | H | $OCH_3$ | H |
| H | F | $CH_3$ | F | H | H | H |
| H | F | $CH_3$ | H | $CH_3$ | H | H |
| H | F | $CH_3$ | H | F | H | H |
| H | F | $CH_3$ | H | H | F | H |
| H | F | $CH_3$ | H | H | H | $OCH_3$ |
| H | F | $CH_3$ | H | H | Cl | H |
| H | F | $CH_3$ | H | H | $OCH_3$ | H |
| H | F | $OCF_2H$ | F | H | H | H |
| H | F | $OCF_2H$ | H | $CH_3$ | H | H |
| H | F | $OCF_2H$ | H | F | H | H |
| H | F | $OCF_2H$ | H | H | F | H |
| H | F | $OCF_2H$ | H | H | H | $OCH_3$ |
| H | F | $OCF_2H$ | H | H | Cl | H |
| H | F | $OCF_2H$ | H | H | $OCH_3$ | H |
| $OCF_2H$ | F | H | F | H | H | H |
| $OCF_2H$ | F | H | H | $CH_3$ | H | H |
| $OCF_2H$ | F | H | H | F | H | H |
| $OCF_2H$ | F | H | H | H | F | H |
| $OCF_2H$ | F | H | H | H | H | $OCH_3$ |
| $OCF_2H$ | F | H | H | H | Cl | H |
| $OCF_2H$ | F | H | H | H | $OCH_3$ | H |
| $OCH_3$ | F | H | F | H | H | H |
| $OCH_3$ | F | H | H | $CH_3$ | H | H |
| $OCH_3$ | F | H | H | F | H | H |
| $OCH_3$ | F | H | H | H | F | H |
| $OCH_3$ | F | H | H | H | H | $OCH_3$ |
| $OCH_3$ | F | H | H | H | Cl | H |
| $OCH_3$ | F | H | H | H | $OCH_3$ | H |

Especially good results could be obtained by the following compounds according to the present invention:

TABLE 7

| Comp. No. | Chemical structure | Relative Pigmentation |
|---|---|---|
| 1 | 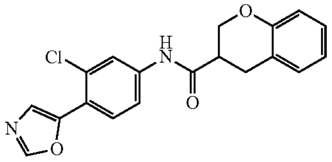 [SMILES: O=C(Nc1ccc(-c2cnco2)c(Cl)c1)C1COc2ccccc2C1] enantiomer with the shorter retention time from the chiral HPLC resolution | 3.05 |
| 2 | 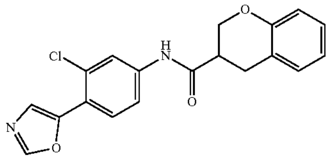 enantiomer with the longer retention time from the chiral HPLC resolution | 1.68 |
| 3 | 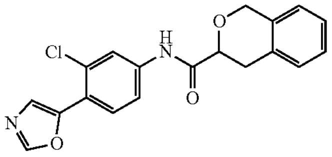 [SMILES: O=C(Nc1ccc(-c2cnco2)c(Cl)c1)C1Cc2ccccc2CO1] (racemate) | 1.66 |
| 4 | 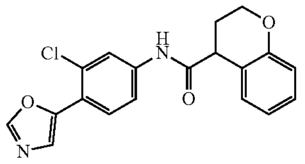 [SMILES: O=C(Nc1ccc(-c2cnco2)c(Cl)c1)C1CCOc2ccccc21] (racemate) | 2.65 |
| 5 | 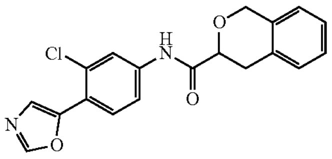 [SMILES: O=C(Nc1ccc(-c2cnco2)c(Cl)c1)C1Cc2ccccc2CO1] (racemate) | 1.18 |
| 6 | 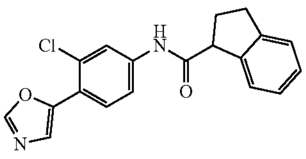 [SMILES: O=C(Nc1ccc(-c2cnco2)c(Cl)c1)C1CCc2ccccc21] (racemate) | 1.86 |

TABLE 7-continued

| Comp. No. | Chemical structure | Relative Pigmentation |
|---|---|---|
| 7 | 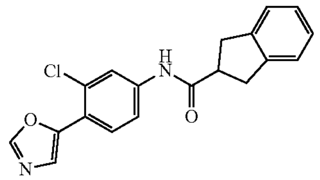 [SMILES: O=C(Nc1ccc(-c2cnco2)c(Cl)c1)C1Cc2ccccc2C1] | 2.92 |
| C* | — | 1 |

C* = Control experiment (absence of a compound according to the present invention).

In particular, the compounds (1) and (7) show excellent results with regard to the pigmentation of RPE cells.

Further preferred compounds providing a good activity are depicted in Table 8. The expression "enantiomer with the shorter retention time from the chiral HPLC resolution" means that the enantiomer comes first in the chiral HPLC when applying the conditions described in the corresponding Chiral Separation Method A, B, C, D, E, F, G, H, I and K below. Within the context of the present invention the enantiomer with the shorter retention time is also called "first enantiomer" and the one with the longer retention time "second enantiomer".

TABLE 8

| Comp. No. | Chemical structure |
|---|---|
| 8 | 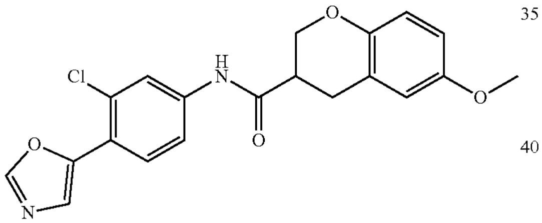 (racemate) |
| 9 | 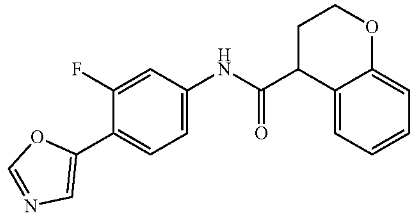 [SMILES: O=C(Nc1ccc(-c2cnco2)c(F)c1)C1CCOc2ccccc21] (racemate) |
| 10 | 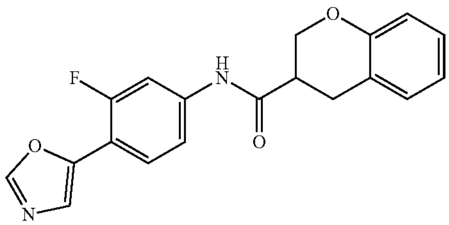 [SMILES: O=C(Nc1ccc(-c2cnco2)c(F)c1)C1COc2ccccc2C1] (racemate) |

TABLE 8-continued

| Comp. No. | Chemical structure |
|---|---|
| 11 | 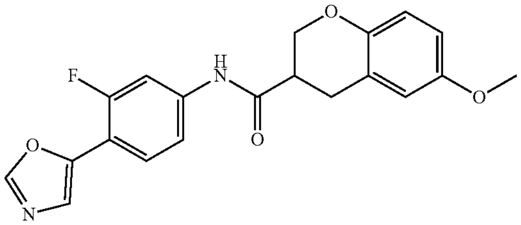 [SMILES: COc1ccc2c(c1)CC(C(=O)Nc1ccc(-c3cnco3)c(F)c1)CO2] (racemate) |
| 12 | 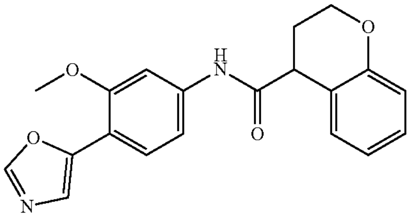 [SMILES: COc1cc(NC(=O)C2CCOc3ccccc32)ccc1-c1cnco1] (racemate) |
| 13 | 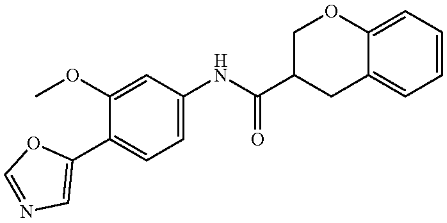 [SMILES: COc1cc(NC(=O)C2COc3ccccc3C2)ccc1-c1cnco1] (racemate) |
| 14 | 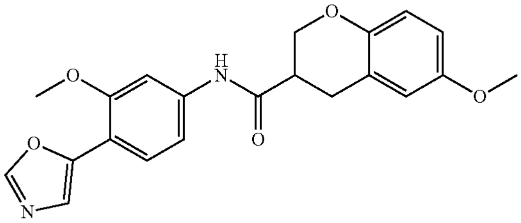 [SMILES: COc1ccc2c(c1)CC(C(=O)Nc1ccc(-c3cnco3)c(OC)c1)CO2] (racemate) |
| 15 | 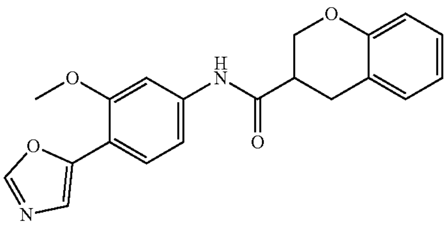 [SMILES: COc1cc(NC(=O)C2COc3ccccc3C2)ccc1-c1cnco1] enantiomer with the shorter retention time from the chiral HPLC resolution |

TABLE 8-continued

| Comp. No. | Chemical structure |
|---|---|
| 16 | 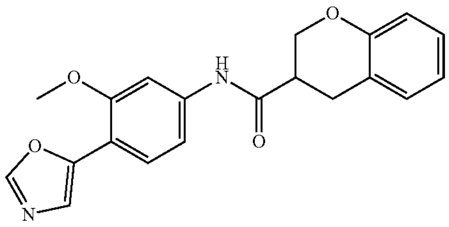 [SMILES: COc1cc(NC(=O)C2COc3ccccc3C2)ccc1-c1cnco1]<br>enantiomer with the longer retention time from the chiral HPLC resolution |
| 17 | 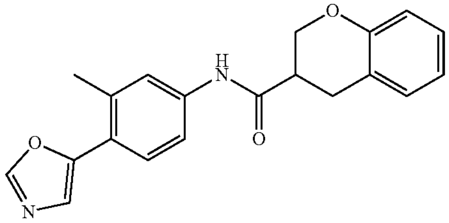 [SMILES: Cc1cc(NC(=O)C2COc3ccccc3C2)ccc1-c1cnco1]<br>(racemate) |
| 18 | 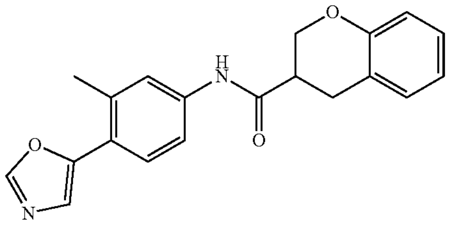 [SMILES: Cc1cc(NC(=O)C2COc3ccccc3C2)ccc1-c1cnco1]<br>enantiomer with the shorter retention time from the chiral HPLC resolution |
| 19 | 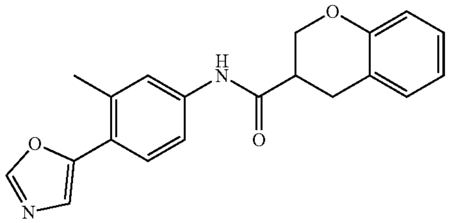 [SMILES: Cc1cc(NC(=O)C2COc3ccccc3C2)ccc1-c1cnco1]<br>enantiomer with the longer retention time from the chiral HPLC resolution |
| 20 | 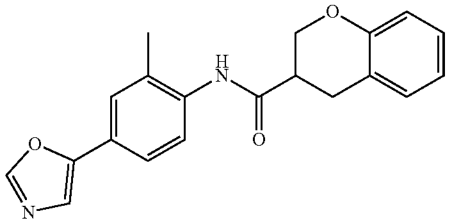 [SMILES: Cc1cc(-c2cnco2)ccc1NC(=O)C1COc2ccccc2C1]<br>(racemate) |
| 21 | 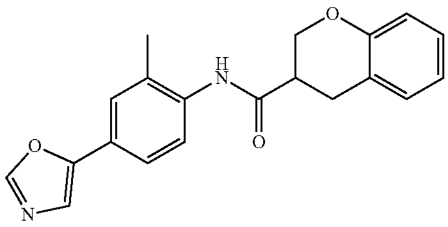 [SMILES: Cc1cc(-c2cnco2)ccc1NC(=O)C1COc2ccccc2C1]<br>enantiomer with the shorter retention time from the chiral HPLC resolution |
| 22 | 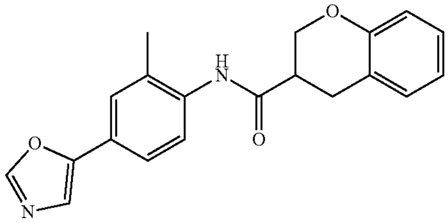 [SMILES: Cc1cc(-c2cnco2)ccc1NC(=O)C1COc2ccccc2C1]<br>enantiomer with the longer retention time from the chiral HPLC resolution |
| 23 | 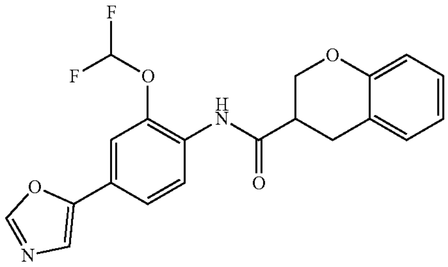 [SMILES: O=C(Nc1ccc(-c2cnco2)cc1OC(F)F)C1COc2ccccc2C1]<br>(racemate) |
| 24 | 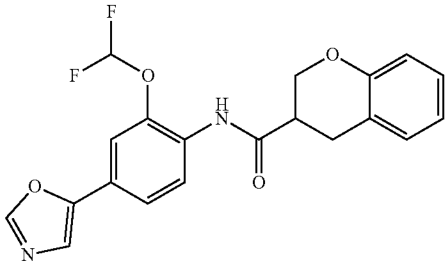 [SMILES: O=C(Nc1ccc(-c2cnco2)cc1OC(F)F)C1COc2ccccc2C1]<br>enantiomer with the shorter retention time from the chiral HPLC resolution |
| 25 | 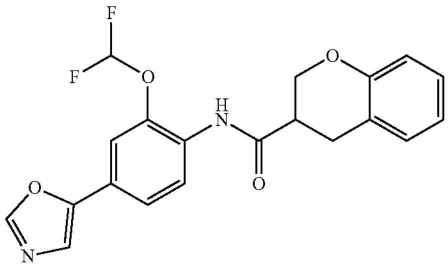 [SMILES: O=C(Nc1ccc(-c2cnco2)cc1OC(F)F)C1COc2ccccc2C1]<br>enantiomer with the longer retention time from the chiral HPLC resolution |

TABLE 8-continued

| Comp. No. | Chemical structure |
|---|---|
| 26 | 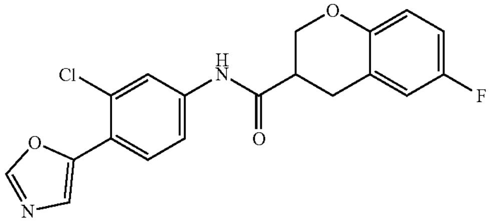 [SMILES: O=C(Nc1ccc(-c2cnco2)c(Cl)c1)C1COc2ccc(F)cc2C1]<br>enantiomer with the shorter retention time from the chiral HPLC resolution |
| 27 | 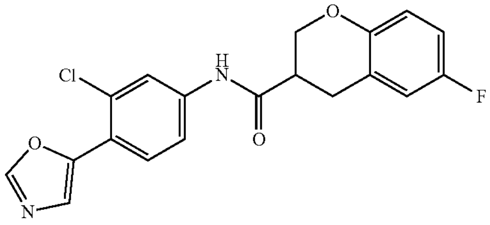 [SMILES: O=C(Nc1ccc(-c2cnco2)c(Cl)c1)C1COc2ccc(F)cc2C1]<br>enantiomer with the longer retention time from the chiral HPLC resolution |
| 28 | 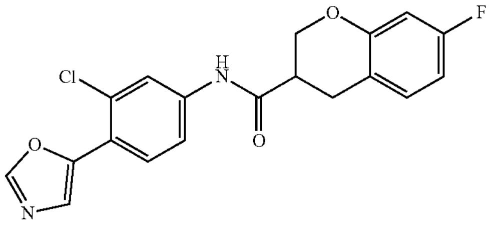 [SMILES: O=C(Nc1ccc(-c2cnco2)c(Cl)c1)C1COc2cc(F)ccc2C1]<br>(racemate) |
| 29 | 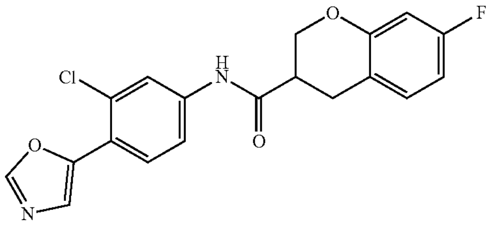 [SMILES: O=C(Nc1ccc(-c2cnco2)c(Cl)c1)C1COc2cc(F)ccc2C1]<br>enantiomer with the shorter retention time from the chiral HPLC resolution |
| 30 | 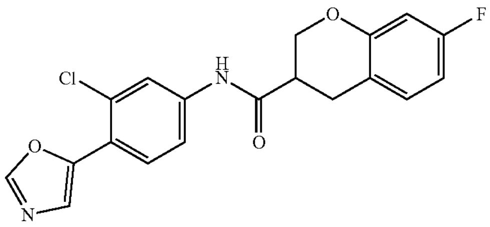 [SMILES: O=C(Nc1ccc(-c2cnco2)c(Cl)c1)C1COc2cc(F)ccc2C1]<br>enantiomer with the longer retention time from the chiral HPLC resolution |
| 31 | 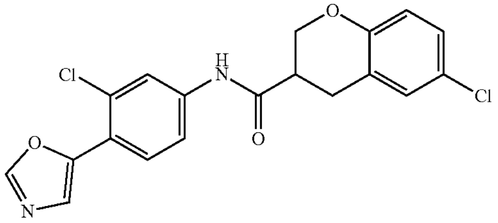 [SMILES: O=C(Nc1ccc(-c2cnco2)c(Cl)c1)C1COc2ccc(Cl)cc2C1]<br>(racemate) |
| 32 | 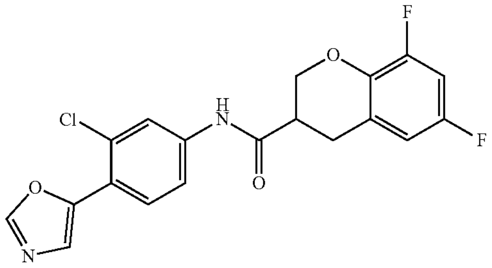 [SMILES: O=C(Nc1ccc(-c2cnco2)c(Cl)c1)C1COc2c(F)cc(F)cc2C1]<br>(racemate) |
| 33 | 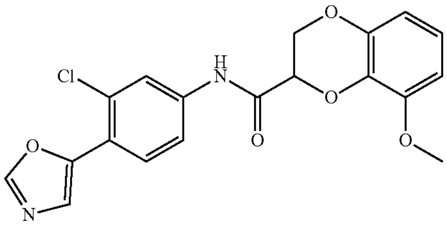 [SMILES: COc1cccc2c1OC(C(=O)Nc1ccc(-c3cnco3)c(Cl)c1)CO2]<br>(racemate) |
| 34 | 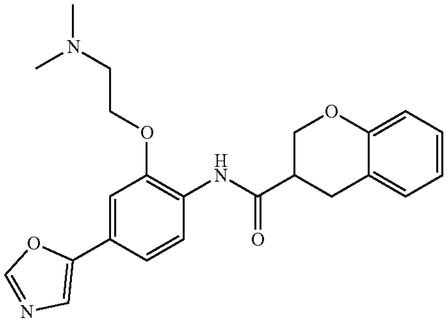 [SMILES: CN(C)CCOc1cc(-c2cnco2)ccc1NC(=O)C1COc2ccccc2C1]<br>(racemate) |

TABLE 8-continued

| Comp. No. | Chemical structure |
|---|---|
| 35 | 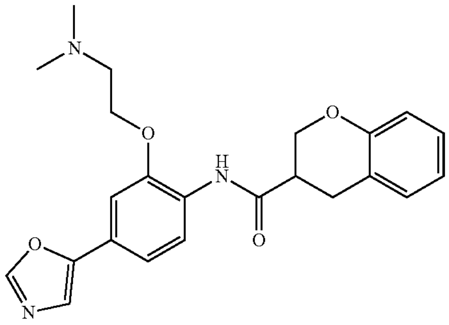 [SMILES: CN(C)CCOc1cc(-c2cnco2)ccc1NC(=O)C1COc2ccccc2C1] enantiomer with the shorter retention time from the chiral HPLC resolution |
| 36 | 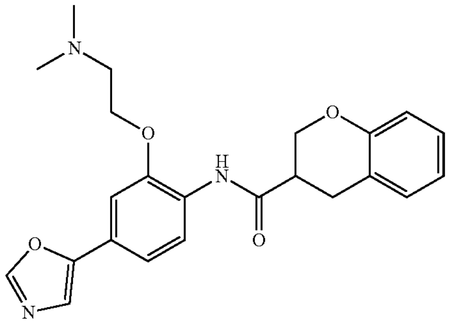 [SMILES: CN(C)CCOc1cc(-c2cnco2)ccc1NC(=O)C1COc2ccccc2C1] enantiomer with the longer retention time from the chiral HPLC resolution |
| 37 | 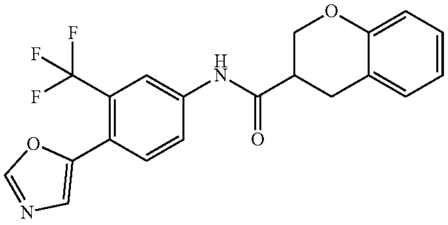 [SMILES: O=C(Nc1ccc(-c2cnco2)c(C(F)(F)F)c1)C1COc2ccccc2C1] (racemate) |
| 38 | 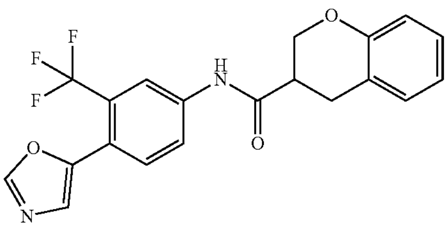 [SMILES: O=C(Nc1ccc(-c2cnco2)c(C(F)(F)F)c1)C1COc2ccccc2C1] enantiomer with the shorter retention time from the chiral HPLC resolution |
| 39 | 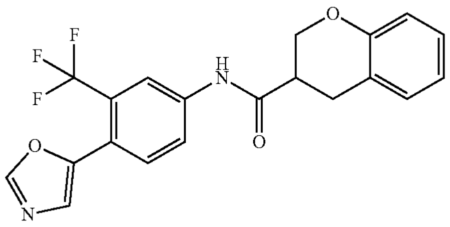 [SMILES: O=C(Nc1ccc(-c2cnco2)c(C(F)(F)F)c1)C1COc2ccccc2C1] enantiomer with the longer retention time from the chiral HPLC resolution |
| 40 | 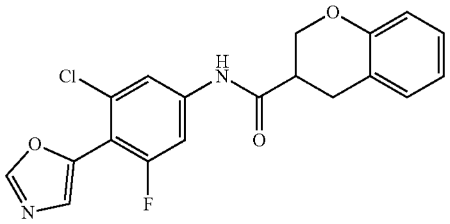 [SMILES: O=C(Nc1cc(F)c(-c2cnco2)c(Cl)c1)C1COc2ccccc2C1] enantiomer with the shorter retention time from the chiral HPLC resolution |
| 41 | 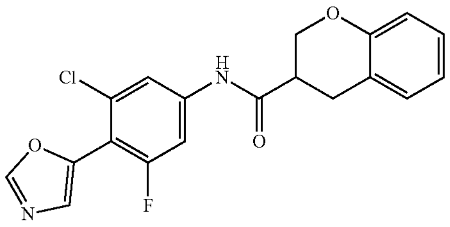 [SMILES: O=C(Nc1cc(F)c(-c2cnco2)c(Cl)c1)C1COc2ccccc2C1] enantiomer with the longer retention time from the chiral HPLC resolution |
| 42 | 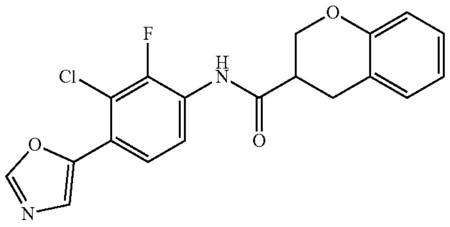 [SMILES: O=C(Nc1ccc(-c2cnco2)c(Cl)c1F)C1COc2ccccc2C1] (racemate) |
| 43 | 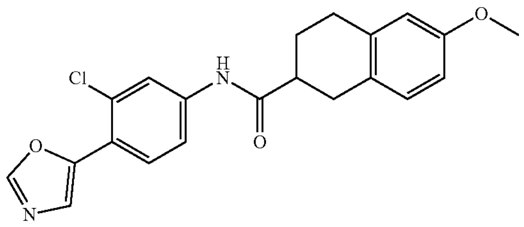 [SMILES: COc1ccc2c(c1)CCC(C(=O)Nc1ccc(-c3cnco3)c(Cl)c1)C2] (racemate) |

TABLE 8-continued

| Comp. No. | Chemical structure |
| --- | --- |
| 44 | 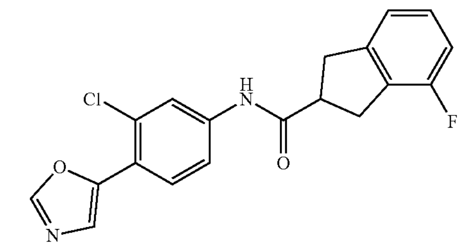 [SMILES: O=C(Nc1ccc(-c2cnco2)c(Cl)c1)C1Cc2cccc(F)c2C1] (racemate) |
| 45 | 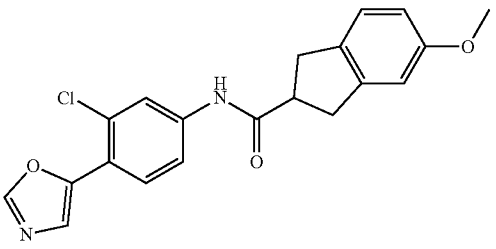 [SMILES: COc1ccc2c(c1)CC(C(=O)Nc1ccc(-c3cnco3)c(Cl)c1)C2] (racemate) |
| 46 | 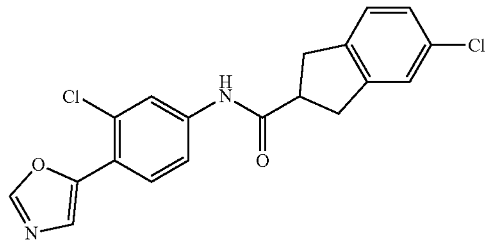 [SMILES: O=C(Nc1ccc(-c2cnco2)c(Cl)c1)C1Cc2ccc(Cl)cc2C1] (racemate) |
| 47 | 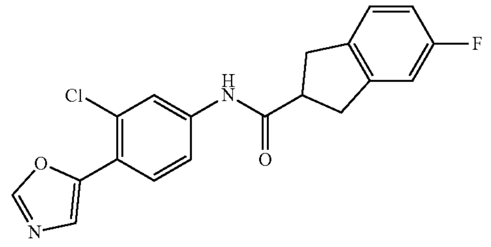 [SMILES: O=C(Nc1ccc(-c2cnco2)c(Cl)c1)C1Cc2ccc(F)cc2C1] (racemate) |

As already mentioned, the compounds according to the present invention and the compositions according to the present invention stimulate the proliferation and/or differentiation of RPE cells. Thus, the compounds according to the present invention can be used in the treatment and/or prevention of RPE-related diseases, in particular of RPE diseases from the family of macular degeneration leading to loss of vision. Most preferably, the disease is a disease leading to atrophy, degeneration or death of the retinal pigment epithelium that might further result in retinal neovascularization and/or death of photoreceptors.

Compounds and compositions according to the present invention are particularly useful in the treatment and/or prevention of disease selected from the group consisting of the family of macular degenerations consisting of early age-related macular degeneration (AMD), dry AMD and geographic atrophy (GA) as well as wet AMD by inducing the proliferation and/or differentiation of RPE cells. Thus, due to the compounds and compositions of the present invention, it is possible to reverse RPE cell damage caused by an illness by restoring or regenerating endogenous RPE cells, and not only to treat the loss of vision caused by RPE cell disfunction and/or damage.

Compounds of formula (I) of the invention can be used, inter alia, to prevent the onset of dry age-related macular degeneration (dry AMD) and/or wet age-related macular degeneration (wet AMD), to prevent the progression of early AMD to advanced forms of AMD including wet AMD or geographic atrophy (GA), to slow and/or prevent progression of GA, to prevent or reduce the loss of vision from AMD, and to improve vision lost due to pre-existing early or advanced dry or wet AMD. It can also be used in combination with anti-VEGF therapies for the treatment of neovascular AMD patients or for the prevention of neovascular AMD.

Compounds and compositions according to the present invention are also useful in the treatment and/or prevention of disease selected from the group consisting of Best disease, autosomal recessive bestrophinopathy (ARB), gyrate atrophy, North Carolina macular dystrophy, central areolar choroidal dystrophy (CACD), Sorsby macular dystrophy, familial dominant drusen, cuticular or basal laminar drusen, retinopathy of prematurity, myopic degeneration, polypoidal choroidal vasculopathy (PCV), central serious retinopathy, angioid streaks, retinal detachment, retinal dialysis, Vogt-Koyanagi-Harada (VKH), acute posterior multifocal placoid pigment epitheliopathy (APMPPE), persistent placoid maculopathy (PPM) relentless placoid chorioretinopathy (RPC), serpiginous choroiditis, serpiginous-like choroiditis (multifocal serpiginoid choroiditis), multiple evanescence white dot syndrome (MEWDS) or Birdshot uveitis (vitiliginous chorioretinitis).

Compounds and compositions according to the present invention are particularly useful in the treatment and/or prevention of disease selected from the group consisting of a retinal disease leading to choroidal neovasculatization or vascular leakage. Said retinal diseases are preferably selected from the group consisting of toxoplasmosis, toxocariasis, rubella, Behgets disease, choroidal hemangioma, trauma, choroidal rupture and idiopathic retinitis—vasculitis—aneurysms and neuroretinitis (IRVAN).

Compounds and compositions according to the present invention are particularly useful in the treatment and/or prevention of disease selected from the group consisting of a retinal disease that causes retinal inflammation and degeneration like sympathetic ophthalmia, post-operative inflammation or non-arteritic ischemic optic neuropathy as well as retinal degeneration associated with systemic disease such as diabetes mellitus, sickle cell disease or radiation retinopathy.

In a further embodiment, the present invention relates to a pharmaceutical composition for use in the treatment and/or prevention of a disease involving the retinal pigment epithelium, said pharmaceutical composition comprising a pharmaceutically acceptable carrier and/or adjuvant; and a compound of the formula (I)

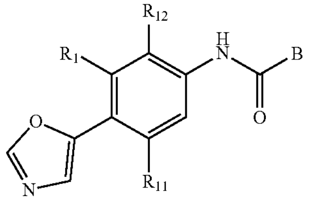

or a pharmaceutically acceptable salt, a racemic mixture, a corresponding enantiomer or, if applicable, a corresponding diastereomer thereof, wherein:

$R_1$, $R_{11}$ and $R_{12}$ are independently selected from the group consisting of hydrogen, fluoro, chloro, methoxy, trifluoromethyl, methyl and difluoromethoxy, whereby at least one of $R_1$, $R_{11}$ and $R_{12}$ is not hydrogen, B is selected from the group consisting of a residue of formula (II), (III), (IV), (V), (VI), (VII)

(II)

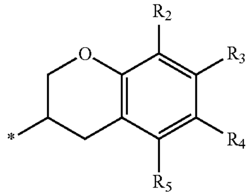

(III)

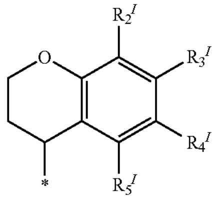

(IV)

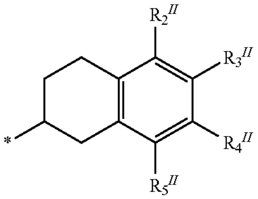

(V)

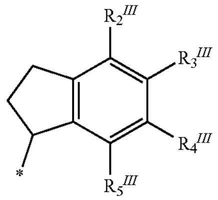

(VI)

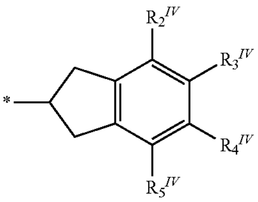

-continued (VII)

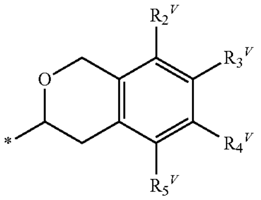

wherein,

"*" denotes the point of attachment to the remainder of the molecule, and $R_2$, $R_3$, $R_4$, $R_5$, $R_2^I$, $R_3^I$, $R_4^I$, $R_5^I$, $R_2^{II}$, $R_3^{II}$, $R_4^{II}$, $R_5^{II}$, $R_2^{III}$, $R_3^{III}$, $R_4^{III}$, $R_5^{III}$, $R_2^{IV}$, $R_3^{IV}$, $R_4^{IV}$, $R_5^{IV}$, $R_2^V$, $R_3^V$, $R_4^V$, $R_5^V$ are independently selected from the group consisting of hydrogen, a linear or branched alkyl having 1 to 3 carbon atoms, fluoro, chloro, bromo, methoxy, ethoxy, propoxy, trifluoromethyl and difluoromethoxy, as a therapeutically active substance and a pharmaceutically acceptable carrier and/or adjuvant for use in the treatment and/or prevention of a disease involving the retinal pigment epithelium.

In a further embodiment, the present invention relates to a pharmaceutical composition for use in the treatment and/or prevention of a disease involving the retinal pigment epithelium, said pharmaceutical composition comprising a pharmaceutically acceptable carrier and/or adjuvant; and a compound of the formula (I)

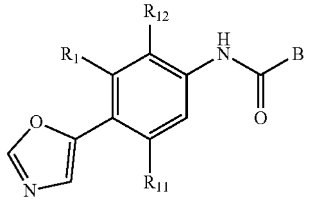

or a pharmaceutically acceptable salt, a racemic mixture, a corresponding enantiomer or, if applicable, a corresponding diastereomer thereof, wherein:

$R_1$, $R_{11}$ and $R_{12}$ are independently selected from the group consisting of hydrogen, fluoro, chloro, methoxy, trifluoromethyl, methyl and difluoromethoxy, whereby at least one of $R_1$, $R_{11}$ and $R_{12}$ is not hydrogen, B is selected from the group consisting of a residue of formula (II), (III), (IV), (V), (VI), (VII)

(II)

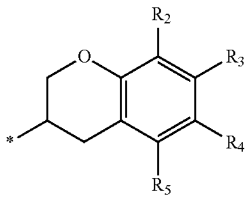

-continued (III)

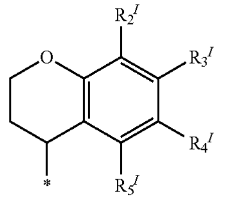

(IV)

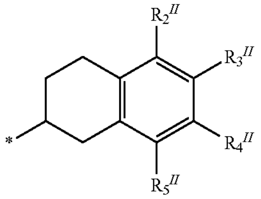

(V)

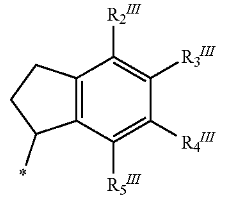

(VI)

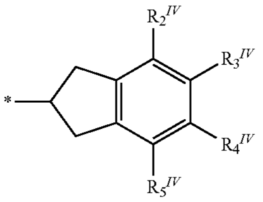

(VII)

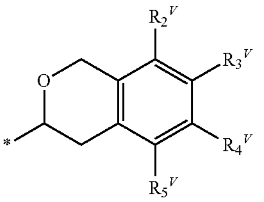

wherein,

"*" denotes the point of attachment to the remainder of the molecule, and $R_2$, $R_3$, $R_4$, $R_5$, $R_2^I$, $R_3^I$, $R_4^I$, $R_5^I$, $R_2^{II}$, $R_3^{II}$, $R_4^{II}$, $R_5^{II}$, $R_2^{III}$, $R_3^{III}$, $R_4^{III}$, $R_5^{III}$, $R_2^{IV}$, $R_3^{IV}$, $R_4^{IV}$, $R_5^{IV}$, $R_2^V$, $R_3^V$, $R_4^V$, $R_5^V$ are independently selected from the group consisting of hydrogen, a linear or branched alkyl having 1 to 3 carbon atoms, fluoro, chloro, bromo, methoxy, ethoxy, propoxy, trifluoromethyl and difluoromethoxy, with the proviso that if a) $R_{11}$ is hydrogen and b) one of $R_1$ and $R_{12}$ is selected from the group consisting of fluoro, chloro and methoxy, trifluoromethyl, methyl and difluoromethoxy, whereas the other of $R_1$ and $R_{12}$ is hydrogen, then B is either a residue of formula (IV) or (VII)

as a therapeutically active substance.

The compound or the composition according to the present invention can be administered to a patient, either alone or in combination with one or more additional therapeutic agents. "Patient" as used herein, includes mammals such as humans, non-human primates, rats, mice, rabbits, hares, dogs, cats, horses, cows and pigs, preferably human.

The pharmaceutical composition according to the present invention may comprise one or more additional therapeutic agents.

In a preferred embodiment of the present invention, the pharmaceutical composition comprises a pharmaceutically acceptable carrier and/or adjuvant; and a compound of the formula (I) as defined above, preferably a compound of formula (Ia), (Ib), (Ic), (Id), (Ie) or (If). Most preferably, it comprises a compound of formula (Ia), (Ib), (Ic), (Id), (Ie) or (If) as disclosed in Table 1, Table 2, Table 3, Table 4, Table 5, Table 6, Table 7 and Table 8 above.

Preferably, such a pharmaceutical composition provides controlled release properties. The term "controlled release pharmaceutical compositions" herein refers to any composition or dosage form, which comprises the compound of the present invention and which is formulated to provide a longer duration of pharmacological response after administration of the dosage form than is ordinarily experienced after administration of a corresponding immediate release composition comprising the same drug in the same amount. Controlled release may be extended up to several months depending on the matrix used. Preferably, the release of the compound according to the present invention takes place over a period of up to 12 months, most preferably over a period of up to 6 months. Such a controlled release formulation results in an increased patient comfort and in significant lower costs.

The matrix material used for a pharmaceutical composition according to the present may comprise hydrophobic release controlling agents. It is preferably selected from but not limited to polyvinyl acetate dispersion, ethyl cellulose, cellulose acetate, cellulose propionate (lower, medium or higher molecular weight), cellulose acetate propionate, cellulose acetate butyrate, cellulose acetate phthalate, cellulose triacetate, poly (methyl methacrylate), poly (ethyl methacrylate), poly (butyl methacrylate), poly (isobutyl methacrylate), and poly (hexyl methacrylate), poly (isodecyl methacrylate), poly (lauryl methacrylate), poly (phenyl methacrylate), poly (methyl acrylate), poly (isopropyl acrylate), poly (isobutyl acrylate), poly (octadecyl acrylate), waxes such as beeswax, carnauba wax, paraffin wax, microcrystalline wax, and ozokerite; fatty alcohols such as cetostearyl alcohol, stearyl alcohol, cetyl alcohol and myristyl alcohol, and fatty acid esters such as glyceryl monostearate; glycerol monooleate, acetylated monoglycerides, tristearin, tripalmitin, cetyl esters wax, glyceryl palmitostearate, glyceryl behenate, or hydrogenated vegetable oils.

The compound of the invention can be delivered to the eye through a variety of routes, including but not limited to topical application to the eye or by intraocular injection into, for example, the vitreous, subretinal (interphotoreceptor) or subconjunctival space; locally by insertion or injection into the tissue surrounding the eye; systemically through an oral route or by subcutaneous, intravenous or intramuscular injection; or via catheter or implant. Most preferably, the compound of the present invention is delivered by intraocular injection. Examples for topical ophthalmic compositions are eye drops, ointments, gels, solutions and suspensions.

The compound of the invention can be administered prior to the onset of the condition to prevent its occurrence, such as during eye surgery, immediately after the onset of the pathological condition, or during the occurrence of an acute or protracted condition.

Depending on the intended mode of administration, the compound according to the present invention may be incorporated in any pharmaceutically acceptable dosage form, such as for example, liquids, including solutions, suspensions and emulsions, tablets, suppositories, pills, capsules, powders or the like, preferably dosage forms suitable for single administration of precise dosages, or sustained release dosage forms for continuous controlled administration. Most preferred are liquids.

Liquid pharmaceutically administrable dosage forms can be for example a solution, a suspension or an emulsion, preferably a suspension comprising a compound of the present invention and optional pharmaceutical adjutants in a carrier, such as for example, water, saline, aqueous dextrose, glycerol, hyaluronic acid, ethanol, DMSO and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate and triethanolamine oleate.

The present invention also relates to a method of the treating and/or preventing RPE-related diseases, comprising administering a compound of formula (I), preferably (Ia), (Ib), (Ic), (Id), (Ie) and (If) or a pharmaceutically acceptable salt, a racemic mixture, a corresponding enantiomer or, if applicable, a corresponding diastereomer thereof to a patient having the retinal disease so as to be delivered to an eye of the patient in an amount effective to treat the retinal disease. The compounds of formula (Ia), (Ib), (Ic), (Id), (Ie) and (If) are defined above in detail.

In a further embodiment, the present invention relates new compound of the formula (I)

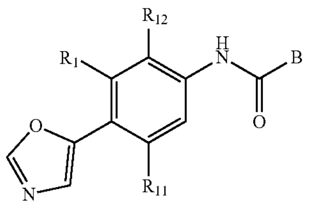

or a pharmaceutically acceptable salt, a racemic mixture, a corresponding enantiomer or, if applicable, a corresponding diastereomer thereof, wherein:

$R_1$, $R_{11}$ and $R_{12}$ are independently selected from the group consisting of hydrogen, fluoro, chloro, methoxy, trifluoromethyl, methyl and difluoromethoxy, whereby at least one of $R_1$, $R_{11}$ and $R_{12}$ is not hydrogen, B is selected from the group consisting of a residue of formula (II), (III), (IV), (V), (VI), (VII)

(II)

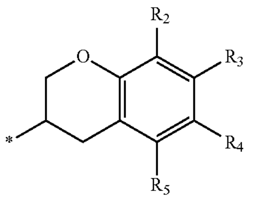

-continued (III)

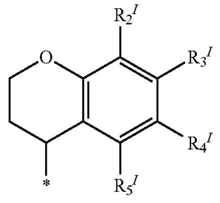

(IV)

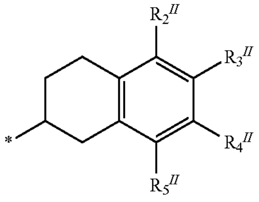

(V)

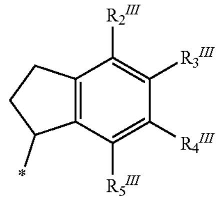

(VI)

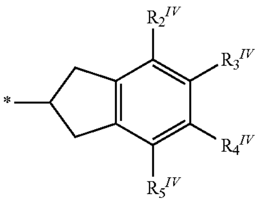

(VII)

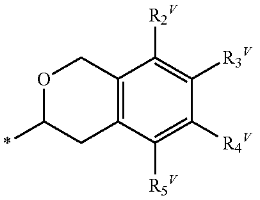

wherein,

"*" denotes the point of attachment to the remainder of the molecule, and $R_2$, $R_3$, $R_4$, $R_5$, $R_2^{I}$, $R_3^{I}$, $R_4^{I}$, $R_5^{I}$, $R_2^{II}$, $R_3^{II}$, $R_4^{II}$, $R_5^{II}$, $R_2^{III}$, $R_3^{III}$, $R_4^{III}$, $R_5^{III}$, $R_2^{IV}$, $R_3^{IV}$, $R_4^{IV}$, $R_5^{IV}$, $R_2^{V}$, $R_3^{V}$, $R_4^{V}$, $R_5^{V}$ are independently selected from the group consisting of hydrogen, a linear or branched alkyl having 1 to 3 carbon atoms, fluoro, chloro, bromo, methoxy, ethoxy, propoxy, trifluoromethyl and difluoromethoxy as a therapeutically active substance.

In a further embodiment the present invention relates to a new compound of the formula (I), wherein the asymmetric center at ring position * of the residue of formula (II), (III), (IV), (V), (VI) and (VII) has the configuration as depicted below (I)

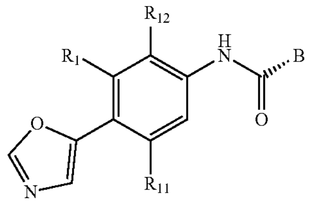

and B is selected from the group consisting of a residue of formula (II), (III), (IV), (V), (VII)

(II)

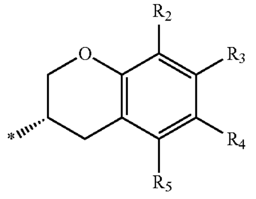

(III)

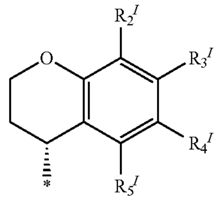

(IV)

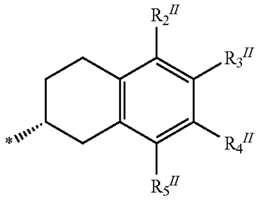

(V)

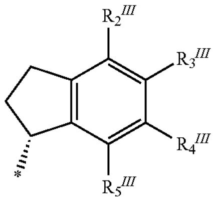

(VI)

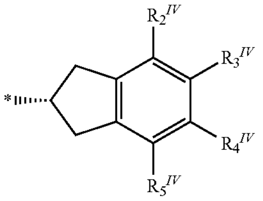

(VII)

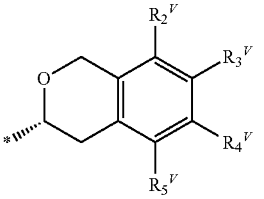

and $R_2$, $R_3$, $R_4$, $R_5$, $R_2^{I}$, $R_3^{I}$, $R_4^{I}$, $R_5^{I}$, $R_2^{II}$, $R_3^{II}$, $R_4^{II}$, $R_5^{II}$, $R_2^{III}$, $R_3^{III}$, $R_4^{III}$, $R_5^{III}$, $R_2^{IV}$, $R_3^{IV}$, $R_4^{IV}$, $R_5^{IV}$, $R_2^{V}$, $R_3^{V}$, $R_4^{V}$, $R_5^{V}$ have the same definition as above, with the proviso that if a) $R_{11}$ is hydrogen and b) one of $R_1$ and $R_{12}$ is selected from the group consisting of fluoro, chloro and methoxy, trifluoromethyl, methyl and difluoromethoxy, whereas the other of $R_1$ and $R_{12}$ is hydrogen, then B is either a residue of formula (IV) or (VII).

In one embodiment of the present invention relates to compounds of (Ia)

(Ia)

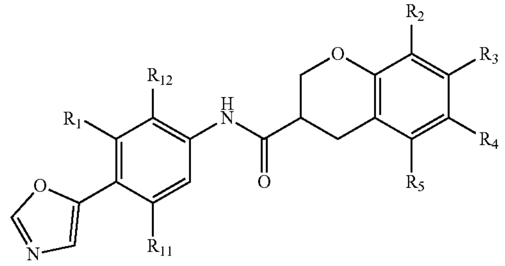

selected from the group consisting of compounds of the formula (Ia) indicated in Table 11, wherein $R_1$, $R_{11}$, $R_{12}$, $R_2$, $R_3$, $R_4$ and $R_5$:

TABLE 11

| $R_1$ | $R_{11}$ | $R_{12}$ | $R_2$ | $R_3$ | $R_4$ | $R_5$ |
|---|---|---|---|---|---|---|
| $CF_3$ | H | H | F | H | H | H |
| $CF_3$ | H | H | H | H | F | H |
| $CF_3$ | H | H | H | H | Cl | H |
| $CH_3$ | H | H | H | H | F | H |
| $CH_3$ | H | H | H | H | Cl | H |
| Cl | H | H | H | F | F | H |
| F | H | H | F | H | H | H |
| F | H | H | H | H | F | H |
| F | H | H | H | H | Cl | H |
| $OCF_2H$ | H | H | H | H | F | H |
| $OCF_2H$ | H | H | H | H | Cl | H |
| $OCH_3$ | H | H | H | H | F | H |
| $OCH_3$ | H | H | H | H | Cl | H |
| H | H | $CF_3$ | F | H | H | H |
| H | H | $CF_3$ | H | H | F | H |
| H | H | $CF_3$ | H | H | Cl | H |
| H | H | $CF_3$ | H | H | $OCH_3$ | H |
| H | H | $CH_3$ | F | H | H | H |
| H | H | $CH_3$ | H | H | F | H |
| H | H | $CH_3$ | H | H | Cl | H |
| H | H | $CH_3$ | H | H | $OCH_3$ | H |
| H | H | $OCF_2H$ | F | H | H | H |
| H | H | $OCF_2H$ | H | H | F | H |
| H | H | $OCF_2H$ | H | H | Cl | H |
| H | H | $OCF_2H$ | H | H | $OCH_3$ | H |
| H | H | $OCH_2CH_2N(CH_3)_2$ | F | H | H | H |
| H | H | $OCH_2CH_2N(CH_3)_2$ | H | $CH_3$ | H | H |
| H | H | $OCH_2CH_2N(CH_3)_2$ | H | F | H | H |
| H | H | $OCH_2CH_2N(CH_3)_2$ | H | H | F | H |
| H | H | $OCH_2CH_2N(CH_3)_2$ | H | H | H | $OCH_3$ |
| H | H | $OCH_2CH_2N(CH_3)_2$ | H | H | Cl | H |
| H | H | $OCH_2CH_2N(CH_3)_2$ | H | H | $OCH_3$ | H |
| $CF_3$ | F | H | F | H | H | H |
| $CF_3$ | F | H | H | $CH_3$ | H | H |
| $CF_3$ | F | H | H | F | H | H |
| $CF_3$ | F | H | H | H | F | H |
| $CF_3$ | F | H | H | H | H | $OCH_3$ |
| $CF_3$ | F | H | H | H | Cl | H |
| $CF_3$ | F | H | H | H | $OCH_3$ | H |
| $CH_3$ | F | H | F | H | H | H |

TABLE 11-continued

| $R_1$ | $R_{11}$ | $R_{12}$ | $R_2$ | $R_3$ | $R_4$ | $R_5$ |
|---|---|---|---|---|---|---|
| $CH_3$ | F | H | H | $CH_3$ | H | H |
| $CH_3$ | F | H | H | F | H | H |
| $CH_3$ | F | H | H | H | F | H |
| $CH_3$ | F | H | H | H | H | $OCH_3$ |
| $CH_3$ | F | H | H | H | Cl | H |
| $CH_3$ | F | H | H | H | $OCH_3$ | H |
| Cl | F | H | F | H | F | H |
| Cl | F | H | F | H | H | H |
| Cl | F | H | H | $CH_3$ | H | H |
| Cl | F | H | H | F | F | H |
| Cl | F | H | H | F | H | H |
| Cl | F | H | H | H | Cl | H |
| Cl | F | H | H | H | F | H |
| Cl | F | H | H | H | H | $OCF_2H$ |
| Cl | F | H | H | H | H | $OCH_3$ |
| F | F | H | H | H | H | H |
| F | F | H | H | $CH_3$ | H | H |
| F | F | H | H | F | H | H |
| F | F | H | H | H | F | H |
| F | F | H | H | H | H | $OCH_3$ |
| F | F | H | H | H | Cl | H |
| F | F | H | H | H | $OCH_3$ | H |
| H | F | $CF_3$ | F | H | H | H |
| H | F | $CF_3$ | H | $CH_3$ | H | H |
| H | F | $CF_3$ | H | F | H | H |
| H | F | $CF_3$ | H | H | F | H |
| H | F | $CF_3$ | H | H | H | $OCH_3$ |
| H | F | $CF_3$ | H | H | Cl | H |
| H | F | $CF_3$ | H | H | $OCH_3$ | H |
| H | F | $CH_3$ | F | H | H | H |
| H | F | $CH_3$ | H | $CH_3$ | H | H |
| H | F | $CH_3$ | H | F | H | H |
| H | F | $CH_3$ | H | H | F | H |
| H | F | $CH_3$ | H | H | H | $OCH_3$ |
| H | F | $CH_3$ | H | H | Cl | H |
| H | F | $CH_3$ | H | H | $OCH_3$ | H |
| H | F | $OCF_2H$ |  | H | H | H |
| H | F | $OCF_2H$ | H | $CH_3$ | H | H |
| H | F | $OCF_2H$ | H | F | H | H |
| H | F | $OCF_2H$ | H | H | F | H |
| H | F | $OCF_2H$ | H | H | H | $OCH_3$ |
| H | F | $OCF_2H$ | H | H | Cl | H |
| H | F | $OCF_2H$ | H | H | $OCH_3$ | H |
| $OCF_2H$ | F | H | F | H | H | H |
| $OCF_2H$ | F | H | H | $CH_3$ | H | H |
| $OCF_2H$ | F | H | H | F | H | H |
| $OCF_2H$ | F | H | H | H | F | H |
| $OCF_2H$ | F | H | H | H | H | $OCH_3$ |
| $OCF_2H$ | F | H | H | H | Cl | H |
| $OCF_2H$ | F | H | H | H | $OCH_3$ | H |
| $OCH_3$ | F | H | F | H | H | H |
| $OCH_3$ | F | H | H | $CH_3$ | H | H |
| $OCH_3$ | F | H | H | F | H | H |
| $OCH_3$ | F | H | H | H | F | H |
| $OCH_3$ | F | H | H | H | H | $OCH_3$ |
| $OCH_3$ | F | H | H | H | Cl | H |
| $OCH_3$ | F | H | H | H | $OCH_3$ | H |

In a further embodiment of the present invention relates to compounds of (Ib)

(Ib)

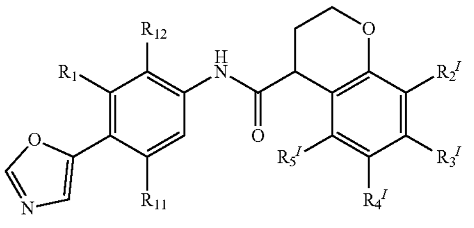

selected from the group consisting of compounds of the formula (Ia) indicated in Table 12, wherein $R_1$, $R_{11}$, $R_{12}$, $R_2^I$, $R_3^I$, $R_4^I$ and $R_5^I$:

TABLE 12

| $R_1$ | $R_{11}$ | $R_{12}$ | $R_2^I$ | $R_3^I$ | $R_4^I$ | $R_5^I$ |
|---|---|---|---|---|---|---|
| $CF_3$ | H | H | F | H | H | H |
| $CF_3$ | H | H | H | H | F | H |
| $CF_3$ | H | H | H | H | Cl | H |
| $CH_3$ | H | H | H | H | F | H |
| $CH_3$ | H | H | H | H | Cl | H |
| Cl | H | H | H | F | F | H |
| F | H | H | F | H | H | H |
| F | H | H | H | H | F | H |
| F | H | H | H | H | Cl | H |
| $OCF_2H$ | H | H | H | H | F | H |
| $OCF_2H$ | H | H | H | H | Cl | H |
| $OCH_3$ | H | H | H | H | F | H |
| $OCH_3$ | H | H | H | H | Cl | H |
| H | H | $CF_3$ | F | H | H | H |
| H | H | $CF_3$ | H | H | F | H |
| H | H | $CF_3$ | H | H | Cl | H |
| H | H | $CF_3$ | H | H | $OCH_3$ | H |
| H | H | $CH_3$ | F | H | H | H |
| H | H | $CH_3$ | H | H | F | H |
| H | H | $CH_3$ | H | H | Cl | H |
| H | H | $CH_3$ | H | H | $OCH_3$ | H |
| H | H | $OCF_2H$ | F | H | H | H |
| H | H | $OCF_2H$ | H | H | F | H |
| H | H | $OCF_2H$ | H | H | Cl | H |
| H | H | $OCF_2H$ | H | H | $OCH_3$ | H |
| H | H | $OCH_2CH_2N(CH_3)_2$ | F | H | H | H |
| H | H | $OCH_2CH_2N(CH_3)_2$ | H | $CH_3$ | H | H |
| H | H | $OCH_2CH_2N(CH_3)_2$ | H | F | H | H |
| H | H | $OCH_2CH_2N(CH_3)_2$ | H | H | F | H |
| H | H | $OCH_2CH_2N(CH_3)_2$ | H | H | H | $OCH_3$ |
| H | H | $OCH_2CH_2N(CH_3)_2$ | H | H | Cl | H |
| H | H | $OCH_2CH_2N(CH_3)_2$ | H | H | $OCH_3$ | H |
| $CF_3$ | F | H | F | H | H | H |
| $CF_3$ | F | H | H | $CH_3$ | H | H |
| $CF_3$ | F | H | H | F | H | H |
| $CF_3$ | F | H | H | H | F | H |
| $CF_3$ | F | H | H | H | H | $OCH_3$ |
| $CF_3$ | F | H | H | H | Cl | H |
| $CF_3$ | F | H | H | H | $OCH_3$ | H |
| $CH_3$ | F | H | F | H | H | H |
| $CH_3$ | F | H | H | $CH_3$ | H | H |
| $CH_3$ | F | H | H | F | H | H |
| $CH_3$ | F | H | H | H | F | H |
| $CH_3$ | F | H | H | H | H | $OCH_3$ |
| $CH_3$ | F | H | H | H | Cl | H |
| $CH_3$ | F | H | H | H | $OCH_3$ | H |
| Cl | F | H | F | H | F | H |
| Cl | F | H | F | H | H | H |
| Cl | F | H | H | $CH_3$ | H | H |
| Cl | F | H | H | F | F | H |
| Cl | F | H | H | F | H | H |
| Cl | F | H | H | H | Cl | H |
| Cl | F | H | H | H | F | H |
| Cl | F | H | H | H | H | $OCF_2H$ |
| Cl | F | H | H | H | H | $OCH_3$ |
| F | F | H | F | H | H | H |
| F | F | H | H | $CH_3$ | H | H |
| F | F | H | H | F | H | H |
| F | F | H | H | H | F | H |
| F | F | H | H | H | H | $OCH_3$ |
| F | F | H | H | H | Cl | H |
| F | F | H | H | H | $OCH_3$ | H |
| H | F | $CF_3$ | F | H | H | H |
| H | F | $CF_3$ | H | $CH_3$ | H | H |
| H | F | $CF_3$ | H | F | H | H |
| H | F | $CF_3$ | H | H | F | H |
| H | F | $CF_3$ | H | H | H | $OCH_3$ |
| H | F | $CF_3$ | H | H | Cl | H |
| H | F | $CF_3$ | H | H | $OCH_3$ | H |
| H | F | $CH_3$ | F | H | H | H |
| H | F | $CH_3$ | H | $CH_3$ | H | H |
| H | F | $CH_3$ | H | F | H | H |
| H | F | $CH_3$ | H | H | F | H |

TABLE 12-continued

| $R_1$ | $R_{11}$ | $R_{12}$ | $R_2^I$ | $R_3^I$ | $R_4^I$ | $R_5^I$ |
|---|---|---|---|---|---|---|
| H | F | $CH_3$ | H | H | H | $OCH_3$ |
| H | F | $CH_3$ | H | H | Cl | H |
| H | F | $CH_3$ | H | H | $OCH_3$ | H |
| H | F | $OCF_2H$ | F | H | H | H |
| H | F | $OCF_2H$ | H | $CH_3$ | H | H |
| H | F | $OCF_2H$ | H | F | H | H |
| H | F | $OCF_2H$ | H | H | F | H |
| H | F | $OCF_2H$ | H | H | H | $OCH_3$ |
| H | F | $OCF_2H$ | H | H | Cl | H |
| H | F | $OCF_2H$ | H | H | $OCH_3$ | H |
| $OCF_2H$ | F | H | F | H | H | H |
| $OCF_2H$ | F | H | H | $CH_3$ | H | H |
| $OCF_2H$ | F | H | H | F | H | H |
| $OCF_2H$ | F | H | H | H | F | H |
| $OCF_2H$ | F | H | H | H | H | $OCH_3$ |
| $OCF_2H$ | F | H | H | H | Cl | H |
| $OCF_2H$ | F | H | H | H | $OCH_3$ | H |
| $OCH_3$ | F | H | F | H | H | H |
| $OCH_3$ | F | H | H | $CH_3$ | H | H |
| $OCH_3$ | F | H | H | F | H | H |
| $OCH_3$ | F | H | H | H | F | H |
| $OCH_3$ | F | H | H | H | H | $OCH_3$ |
| $OCH_3$ | F | H | H | H | Cl | H |
| $OCH_3$ | F | H | H | H | $OCH_3$ | H |

In a further embodiment of the present invention relates to compounds of (Ic)

(Ic)

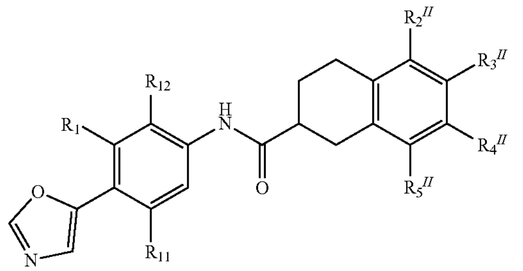

selected from the group consisting of compounds of the formula (Ia) indicated in Table 13, wherein $R_1$, $R_{11}$, $R_{12}$, $R_2^{II}$, $R_3^{II}$, $R_4^{II}$ and $R_5^{II}$:

TABLE 13

| $R_1$ | $R_{11}$ | $R_{12}$ | $R_2^{II}$ | $R_3^{II}$ | $R_4^{II}$ | $R_5^{II}$ |
|---|---|---|---|---|---|---|
| $CF_3$ | H | H | F | H | H | H |
| $CF_3$ | H | H | H | H | F | H |
| $CF_3$ | H | H | H | H | Cl | H |
| $CH_3$ | H | H | H | H | F | H |
| $CH_3$ | H | H | H | H | Cl | H |
| Cl | H | H | H | F | F | H |
| F | H | H | F | H | H | H |
| F | H | H | H | H | F | H |
| F | H | H | H | H | Cl | H |
| $OCF_2H$ | H | H | H | H | F | H |
| $OCF_2H$ | H | H | H | H | Cl | H |
| $OCH_3$ | H | H | H | H | F | H |
| $OCH_3$ | H | H | H | H | Cl | H |
| H | H | $CF_3$ | F | H | H | H |
| H | H | $CF_3$ | H | H | F | H |
| H | H | $CF_3$ | H | H | Cl | H |
| H | H | $CF_3$ | H | H | $OCH_3$ | H |
| H | H | $CH_3$ | F | H | H | H |
| H | H | $CH_3$ | H | H | F | H |
| H | H | $CH_3$ | H | H | Cl | H |
| H | H | $CH_3$ | H | H | $OCH_3$ | H |
| H | H | $OCF_2H$ | F | H | H | H |
| H | H | $OCF_2H$ | H | H | F | H |

TABLE 13-continued

| $R_1$ | $R_{11}$ | $R_{12}$ | $R_2^{II}$ | $R_3^{II}$ | $R_4^{II}$ | $R_5^{II}$ |
|---|---|---|---|---|---|---|
| H | H | $OCF_2H$ | H | H | Cl | H |
| H | H | $OCF_2H$ | H | H | $OCH_3$ | H |
| H | H | $OCH_2CH_2N(CH_3)_2$ | F | H | H | H |
| H | H | $OCH_2CH_2N(CH_3)_2$ | H | $CH_3$ | H | H |
| H | H | $OCH_2CH_2N(CH_3)_2$ | H | F | H | H |
| H | H | $OCH_2CH_2N(CH_3)_2$ | H | H | F | H |
| H | H | $OCH_2CH_2N(CH_3)_2$ | H | H | H | $OCH_3$ |
| H | H | $OCH_2CH_2N(CH_3)_2$ | H | H | Cl | H |
| H | H | $OCH_2CH_2N(CH_3)_2$ | H | H | $OCH_3$ | H |
| $CF_3$ | F | H | F | H | H | H |
| $CF_3$ | F | H | H | $CH_3$ | H | H |
| $CF_3$ | F | H | H | F | H | H |
| $CF_3$ | F | H | H | H | F | H |
| $CF_3$ | F | H | H | H | H | $OCH_3$ |
| $CF_3$ | F | H | H | H | Cl | H |
| $CF_3$ | F | H | H | H | $OCH_3$ | H |
| $CH_3$ | F | H | F | H | H | H |
| $CH_3$ | F | H | H | $CH_3$ | H | H |
| $CH_3$ | F | H | H | F | H | H |
| $CH_3$ | F | H | H | H | F | H |
| $CH_3$ | F | H | H | H | H | $OCH_3$ |
| $CH_3$ | F | H | H | H | Cl | H |
| $CH_3$ | F | H | H | H | $OCH_3$ | H |
| Cl | F | H | F | H | F | H |
| Cl | F | H | F | H | H | H |
| Cl | F | H | H | $CH_3$ | H | H |
| Cl | F | H | H | F | F | H |
| Cl | F | H | H | F | H | H |
| Cl | F | H | H | H | Cl | H |
| Cl | F | H | H | H | F | H |
| Cl | F | H | H | H | H | $OCF_2H$ |
| Cl | F | H | H | H | H | $OCH_3$ |
| F | F | H | F | H | H | H |
| F | F | H | H | $CH_3$ | H | H |
| F | F | H | H | F | H | H |
| F | F | H | H | H | F | H |
| F | F | H | H | H | H | $OCH_3$ |
| F | F | H | H | H | Cl | H |
| F | F | H | H | H | $OCH_3$ | H |
| H | F | $CF_3$ | F | H | H | H |
| H | F | $CF_3$ | H | $CH_3$ | H | H |
| H | F | $CF_3$ | H | F | H | H |
| H | F | $CF_3$ | H | H | F | H |
| H | F | $CF_3$ | H | H | H | $OCH_3$ |
| H | F | $CF_3$ | H | H | Cl | H |
| H | F | $CF_3$ | H | H | $OCH_3$ | H |
| H | F | $CH_3$ | F | H | H | H |
| H | F | $CH_3$ | H | $CH_3$ | H | H |
| H | F | $CH_3$ | H | F | H | H |
| H | F | $CH_3$ | H | H | F | H |
| H | F | $CH_3$ | H | H | H | $OCH_3$ |
| H | F | $CH_3$ | H | H | Cl | H |
| H | F | $CH_3$ | H | H | $OCH_3$ | H |
| H | F | $OCF_2H$ | F | H | H | H |
| H | F | $OCF_2H$ | H | $CH_3$ | H | H |
| H | F | $OCF_2H$ | H | F | H | H |
| H | F | $OCF_2H$ | H | H | F | H |
| H | F | $OCF_2H$ | H | H | H | $OCH_3$ |
| H | F | $OCF_2H$ | H | H | Cl | H |
| H | F | $OCF_2H$ | H | H | $OCH_3$ | H |
| $OCF_2H$ | F | H | F | H | H | H |
| $OCF_2H$ | F | H | H | $CH_3$ | H | H |
| $OCF_2H$ | F | H | H | F | H | H |
| $OCF_2H$ | F | H | H | H | F | H |
| $OCF_2H$ | F | H | H | H | H | $OCH_3$ |
| $OCF_2H$ | F | H | H | H | Cl | H |
| $OCF_2H$ | F | H | H | H | $OCH_3$ | H |
| $OCH_3$ | F | H | F | H | H | H |
| $OCH_3$ | F | H | H | $CH_3$ | H | H |
| $OCH_3$ | F | H | H | F | H | H |
| $OCH_3$ | F | H | H | H | F | H |
| $OCH_3$ | F | H | H | H | H | $OCH_3$ |
| $OCH_3$ | F | H | H | H | Cl | H |
| $OCH_3$ | F | H | H | H | $OCH_3$ | H |

In a further embodiment of the present invention relates to compounds of (Id)

(Id)

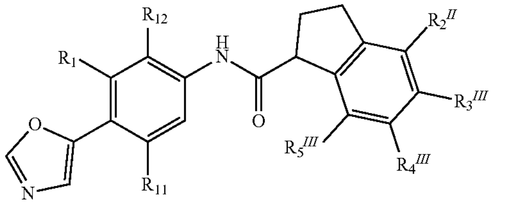

selected from the group consisting of compounds of the formula (Ia) indicated in Table 14, wherein $R_1$, $R_{11}$, $R_{12}$, $R_2^{III}$, $R_3^{III}$, $R_4^{III}$ and $R_5^{III}$:

TABLE 14

| $R_1$ | $R_{11}$ | $R_{12}$ | $R_2^{III}$ | $R_3^{III}$ | $R_4^{III}$ | $R_5^{III}$ |
|---|---|---|---|---|---|---|
| $CF_3$ | H | H | F | H | H | H |
| $CF_3$ | H | H | H | H | F | H |
| $CF_3$ | H | H | H | H | Cl | H |
| $CH_3$ | H | H | H | H | F | H |
| $CH_3$ | H | H | H | H | Cl | H |
| Cl | H | H | H | F | F | H |
| F | H | H | F | H | H | H |
| F | H | H | H | H | F | H |
| F | H | H | H | H | Cl | H |
| $OCF_2H$ | H | H | H | H | F | H |
| $OCF_2H$ | H | H | H | H | Cl | H |
| $OCH_3$ | H | H | H | H | F | H |
| $OCH_3$ | H | H | H | H | Cl | H |
| H | H | $CF_3$ | F | H | H | H |
| H | H | $CF_3$ | H | H | F | H |
| H | H | $CF_3$ | H | H | Cl | H |
| H | H | $CF_3$ | H | H | $OCH_3$ | H |
| H | H | $CH_3$ | F | H | H | H |
| H | H | $CH_3$ | H | H | F | H |
| H | H | $CH_3$ | H | H | Cl | H |
| H | H | $CH_3$ | H | H | $OCH_3$ | H |
| H | H | $OCF_2H$ | F | H | H | H |
| H | H | $OCF_2H$ | H | H | F | H |
| H | H | $OCF_2H$ | H | H | Cl | H |
| H | H | $OCF_2H$ | H | H | $OCH_3$ | H |
| H | H | $OCH_2CH_2N(CH_3)_2$ | F | H | H | H |
| H | H | $OCH_2CH_2N(CH_3)_2$ | H | $CH_3$ | H | H |
| H | H | $OCH_2CH_2N(CH_3)_2$ | H | F | H | H |
| H | H | $OCH_2CH_2N(CH_3)_2$ | H | H | F | H |
| H | H | $OCH_2CH_2N(CH_3)_2$ | H | H | H | $OCH_3$ |
| H | H | $OCH_2CH_2N(CH_3)_2$ | H | H | Cl | H |
| H | H | $OCH_2CH_2N(CH_3)_2$ | H | H | $OCH_3$ | H |
| $CF_3$ | F | H | F | H | H | H |
| $CF_3$ | F | H | H | $CH_3$ | H | H |
| $CF_3$ | F | H | H | F | H | H |
| $CF_3$ | F | H | H | H | F | H |
| $CF_3$ | F | H | H | H | H | $OCH_3$ |
| $CF_3$ | F | H | H | H | Cl | H |
| $CF_3$ | F | H | H | H | $OCH_3$ | H |
| $CH_3$ | F | H | F | H | H | H |
| $CH_3$ | F | H | H | $CH_3$ | H | H |
| $CH_3$ | F | H | H | F | H | H |
| $CH_3$ | F | H | H | H | F | H |
| $CH_3$ | F | H | H | H | H | $OCH_3$ |
| $CH_3$ | F | H | H | H | Cl | H |
| $CH_3$ | F | H | H | H | $OCH_3$ | H |
| Cl | F | H | F | H | F | H |
| Cl | F | H | F | H | H | H |
| Cl | F | H | H | $CH_3$ | H | H |
| Cl | F | H | H | F | F | H |
| Cl | F | H | H | F | H | H |
| Cl | F | H | H | H | Cl | H |
| Cl | F | H | H | H | F | H |
| Cl | F | H | H | H | H | $OCF_2H$ |
| Cl | F | H | H | H | H | $OCH_3$ |
| F | F | H | F | H | H | H |
| F | F | H | H | $CH_3$ | H | H |
| F | F | H | H | F | H | H |
| F | F | H | H | H | F | H |

TABLE 14-continued

| $R_1$ | $R_{11}$ | $R_{12}$ | $R_2^{III}$ | $R_3^{III}$ | $R_4^{III}$ | $R_5^{III}$ |
|---|---|---|---|---|---|---|
| F | F | H | H | H | H | $OCH_3$ |
| F | F | H | H | H | Cl | H |
| F | F | H | H | H | $OCH_3$ | H |
| H | F | $CF_3$ | F | H | H | H |
| H | F | $CF_3$ | H | $CH_3$ | H | H |
| H | F | $CF_3$ | H | F | H | H |
| H | F | $CF_3$ | H | H | F | H |
| H | F | $CF_3$ | H | H | H | $OCH_3$ |
| H | F | $CF_3$ | H | H | Cl | H |
| H | F | $CF_3$ | H | H | $OCH_3$ | H |
| H | F | $CH_3$ | F | H | H | H |
| H | F | $CH_3$ | H | $CH_3$ | H | H |
| H | F | $CH_3$ | H | F | H | H |
| H | F | $CH_3$ | H | H | F | H |
| H | F | $CH_3$ | H | H | H | $OCH_3$ |
| H | F | $CH_3$ | H | H | Cl | H |
| H | F | $CH_3$ | H | H | $OCH_3$ | H |
| H | F | $OCF_2H$ | F | H | H | H |
| H | F | $OCF_2H$ | H | $CH_3$ | H | H |
| H | F | $OCF_2H$ | H | F | H | H |
| H | F | $OCF_2H$ | H | H | F | H |
| H | F | $OCF_2H$ | H | H | H | $OCH_3$ |
| H | F | $OCF_2H$ | H | H | Cl | H |
| H | F | $OCF_2H$ | H | H | $OCH_3$ | H |
| $OCF_2H$ | F | H | F | H | H | H |
| $OCF_2H$ | F | H | H | $CH_3$ | H | H |
| $OCF_2H$ | F | H | H | F | H | H |
| $OCF_2H$ | F | H | H | H | F | H |
| $OCF_2H$ | F | H | H | H | H | $OCH_3$ |
| $OCF_2H$ | F | H | H | H | Cl | H |
| $OCF_2H$ | F | H | H | H | $OCH_3$ | H |
| $OCH_3$ | F | H | F | H | H | H |
| $OCH_3$ | F | H | H | $CH_3$ | H | H |
| $OCH_3$ | F | H | H | F | H | H |
| $OCH_3$ | F | H | H | H | F | H |
| $OCH_3$ | F | H | H | H | H | $OCH_3$ |
| $OCH_3$ | F | H | H | H | Cl | H |
| $OCH_3$ | F | H | H | H | $OCH_3$ | H |

In a further embodiment of the present invention relates to compounds of (Ie)

(Ie)

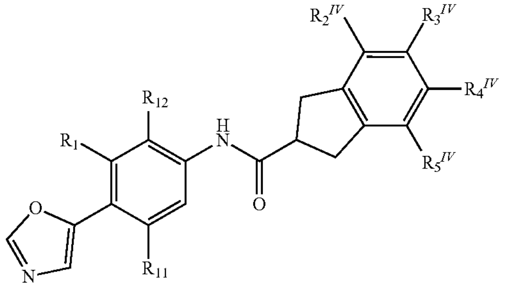

selected from the group consisting of compounds of the formula (Ie) indicated in Table 15, wherein $R_1$, $R_{11}$, $R_{12}$, $R_2^{IV}$, $R_3^{IV}$, $R_4^{IV}$ and $R_5^{IV}$:

TABLE 15

| $R_1$ | $R_{11}$ | $R_{12}$ | $R_2^{IV}$ | $R_3^{IV}$ | $R_4^{IV}$ | $R_5^{IV}$ |
|---|---|---|---|---|---|---|
| $CF_3$ | H | H | F | H | H | H |
| $CF_3$ | H | H | H | H | F | H |
| $CF_3$ | H | H | H | H | Cl | H |
| $CH_3$ | H | H | H | H | F | H |
| $CH_3$ | H | H | H | H | Cl | H |
| Cl | H | H | H | F | F | H |
| F | H | H | F | H | H | H |
| F | H | H | H | H | F | H |

TABLE 15-continued

| $R_1$ | $R_{11}$ | $R_{12}$ | $R_2^{IV}$ | $R_3^{IV}$ | $R_4^{IV}$ | $R_5^{IV}$ |
|---|---|---|---|---|---|---|
| F | H | H | H | H | Cl | H |
| $OCF_2H$ | H | H | H | H | F | H |
| $OCF_2H$ | H | H | H | H | Cl | H |
| $OCH_3$ | H | H | H | H | F | H |
| $OCH_3$ | H | H | H | H | Cl | H |
| H | H | $CF_3$ | F | H | H | H |
| H | H | $CF_3$ | H | H | F | H |
| H | H | $CF_3$ | H | H | Cl | H |
| H | H | $CF_3$ | H | H | $OCH_3$ | H |
| H | H | $CH_3$ | F | H | H | H |
| H | H | $CH_3$ | H | H | F | H |
| H | H | $CH_3$ | H | H | Cl | H |
| H | H | $CH_3$ | H | H | $OCH_3$ | H |
| H | H | $OCF_2H$ | F | H | H | H |
| H | H | $OCF_2H$ | H | H | F | H |
| H | H | $OCF_2H$ | H | H | Cl | H |
| H | H | $OCF_2H$ | H | H | $OCH_3$ | H |
| H | H | $OCH_2CH_2N(CH_3)_2$ | F | H | H | H |
| H | H | $OCH_2CH_2N(CH_3)_2$ | H | $CH_3$ | H | H |
| H | H | $OCH_2CH_2N(CH_3)_2$ | H | F | H | H |
| H | H | $OCH_2CH_2N(CH_3)_2$ | H | H | F | H |
| H | H | $OCH_2CH_2N(CH_3)_2$ | H | H | H | $OCH_3$ |
| H | H | $OCH_2CH_2N(CH_3)_2$ | H | H | Cl | H |
| H | H | $OCH_2CH_2N(CH_3)_2$ | H | H | $OCH_3$ | H |
| $CF_3$ | F | H | F | H | H | H |
| $CF_3$ | F | H | H | $CH_3$ | H | H |
| $CF_3$ | F | H | H | F | H | H |
| $CF_3$ | F | H | H | H | F | H |
| $CF_3$ | F | H | H | H | H | $OCH_3$ |
| $CF_3$ | F | H | H | H | Cl | H |
| $CF_3$ | F | H | H | H | $OCH_3$ | H |
| $CH_3$ | F | H | F | H | H | H |
| $CH_3$ | F | H | H | $CH_3$ | H | H |
| $CH_3$ | F | H | H | F | H | H |
| $CH_3$ | F | H | H | H | F | H |
| $CH_3$ | F | H | H | H | H | $OCH_3$ |
| $CH_3$ | F | H | H | H | Cl | H |
| $CH_3$ | F | H | H | H | $OCH_3$ | H |
| Cl | F | H | F | H | F | H |
| Cl | F | H | F | H | H | H |
| Cl | F | H | H | $CH_3$ | H | H |
| Cl | F | H | H | F | F | H |
| Cl | F | H | H | F | H | H |
| Cl | F | H | H | H | Cl | H |
| Cl | F | H | H | H | F | H |
| Cl | F | H | H | H | H | $OCF_2H$ |
| Cl | F | H | H | H | H | $OCH_3$ |
| F | F | H | F | H | H | H |
| F | F | H | H | $CH_3$ | H | H |
| F | F | H | H | F | H | H |
| F | F | H | H | H | F | H |
| F | F | H | H | H | H | $OCH_3$ |
| F | F | H | H | H | Cl | H |
| F | F | H | H | H | $OCH_3$ | H |
| H | F | $CF_3$ | F | H | H | H |
| H | F | $CF_3$ | H | $CH_3$ | H | H |
| H | F | $CF_3$ | H | F | H | H |
| H | F | $CF_3$ | H | H | F | H |
| H | F | $CF_3$ | H | H | H | $OCH_3$ |
| H | F | $CF_3$ | H | H | Cl | H |
| H | F | $CF_3$ | H | H | $OCH_3$ | H |
| H | F | $CH_3$ | F | H | H | H |
| H | F | $CH_3$ | H | $CH_3$ | H | H |
| H | F | $CH_3$ | H | F | H | H |
| H | F | $CH_3$ | H | H | F | H |
| H | F | $CH_3$ | H | H | H | $OCH_3$ |
| H | F | $CH_3$ | H | H | Cl | H |
| H | F | $CH_3$ | H | H | $OCH_3$ | H |
| H | F | $OCF_2H$ | F | H | H | H |
| H | F | $OCF_2H$ | H | $CH_3$ | H | H |
| H | F | $OCF_2H$ | H | F | H | H |
| H | F | $OCF_2H$ | H | H | F | H |
| H | F | $OCF_2H$ | H | H | H | $OCH_3$ |
| H | F | $OCF_2H$ | H | H | Cl | H |
| H | F | $OCF_2H$ | H | H | $OCH_3$ | H |
| $OCF_2H$ | F | H | F | H | H | H |
| $OCF_2H$ | F | H | H | $CH_3$ | H | H |
| $OCF_2H$ | F | H | H | F | H | H |

TABLE 15-continued

| $R_1$ | $R_{11}$ | $R_{12}$ | $R_2^{IV}$ | $R_3^{IV}$ | $R_4^{IV}$ | $R_5^{IV}$ |
|---|---|---|---|---|---|---|
| $OCF_2H$ | F | H | H | H | F | H |
| $OCF_2H$ | F | H | H | H | H | $OCH_3$ |
| $OCF_2H$ | F | H | H | H | Cl | H |
| $OCF_2H$ | F | H | H | H | $OCH_3$ | H |
| $OCH_3$ | F | H | F | H | H | H |
| $OCH_3$ | F | H | H | $CH_3$ | H | H |
| $OCH_3$ | F | H | H | F | H | H |
| $OCH_3$ | F | H | H | H | F | H |
| $OCH_3$ | F | H | H | H | H | $OCH_3$ |
| $OCH_3$ | F | H | H | H | Cl | H |
| $OCH_3$ | F | H | H | H | $OCH_3$ | H |

In a further embodiment of the present invention relates to compounds of (If)

(If)

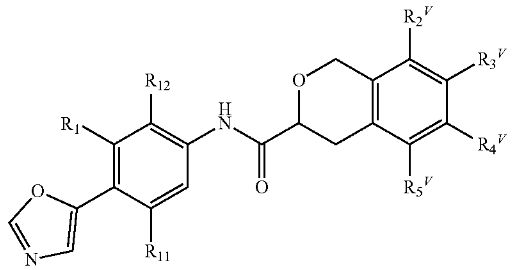

selected from the group consisting of compounds of the formula (If) indicated in Table 16, wherein $R_1$, $R_{11}$, $R_{12}$, $R_2^V$, $R_3^V$, $R_4^V$ and $R_5^V$:

TABLE 16

| $R_1$ | $R_{11}$ | $R_{12}$ | $R_2^V$ | $R_3^V$ | $R_4^V$ | $R_5^V$ |
|---|---|---|---|---|---|---|
| $CF_3$ | H | H | F | H | H | H |
| $CF_3$ | H | H | H | H | F | H |
| $CF_3$ | H | H | H | H | Cl | H |
| $CH_3$ | H | H | H | H | F | H |
| $CH_3$ | H | H | H | H | Cl | H |
| Cl | H | H | H | F | F | H |
| F | H | H | F | H | H | H |
| F | H | H | H | H | F | H |
| F | H | H | H | H | Cl | H |
| $OCF_2H$ | H | H | H | H | F | H |
| $OCF_2H$ | H | H | H | H | Cl | H |
| $OCH_3$ | H | H | H | H | F | H |
| $OCH_3$ | H | H | H | H | Cl | H |
| H | H | $CF_3$ | F | H | H | H |
| H | H | $CF_3$ | H | H | F | H |
| H | H | $CF_3$ | H | H | Cl | H |
| H | H | $CF_3$ | H | H | $OCH_3$ | H |
| H | H | $CH_3$ | F | H | H | H |
| H | H | $CH_3$ | H | H | F | H |
| H | H | $CH_3$ | H | H | Cl | H |
| H | H | $CH_3$ | H | H | $OCH_3$ | H |
| H | H | $OCF_2H$ | F | H | H | H |
| H | H | $OCF_2H$ | H | H | F | H |
| H | H | $OCF_2H$ | H | H | Cl | H |
| H | H | $OCF_2H$ | H | H | $OCH_3$ | H |
| H | H | $OCH_2CH_2N(CH_3)_2$ | F | H | H | H |
| H | H | $OCH_2CH_2N(CH_3)_2$ | H | $CH_3$ | H | H |
| H | H | $OCH_2CH_2N(CH_3)_2$ | H | F | H | H |
| H | H | $OCH_2CH_2N(CH_3)_2$ | H | H | F | H |
| H | H | $OCH_2CH_2N(CH_3)_2$ | H | H | H | $OCH_3$ |
| H | H | $OCH_2CH_2N(CH_3)_2$ | H | H | Cl | H |
| H | H | $OCH_2CH_2N(CH_3)_2$ | H | H | $OCH_3$ | H |
| $CF_3$ | F | H | F | H | H | H |
| $CF_3$ | F | H | H | $CH_3$ | H | H |
| $CF_3$ | F | H | H | F | H | H |
| $CF_3$ | F | H | H | H | F | H |

TABLE 16-continued

| $R_1$ | $R_{11}$ | $R_{12}$ | $R_2^V$ | $R_3^V$ | $R_4^V$ | $R_5^V$ |
|---|---|---|---|---|---|---|
| $CF_3$ | F | H | H | H | H | $OCH_3$ |
| $CF_3$ | F | H | H | H | Cl | H |
| $CF_3$ | F | H | H | H | $OCH_3$ | H |
| $CH_3$ | F | H | F | H | H | H |
| $CH_3$ | F | H | H | $CH_3$ | H | H |
| $CH_3$ | F | H | H | F | H | H |
| $CH_3$ | F | H | H | H | F | H |
| $CH_3$ | F | H | H | H | H | $OCH_3$ |
| $CH_3$ | F | H | H | H | Cl | H |
| $CH_3$ | F | H | H | H | $OCH_3$ | H |
| Cl | F | H | F | H | F | H |
| Cl | F | H | F | H | H | H |
| Cl | F | H | H | $CH_3$ | H | H |
| Cl | F | H | H | F | F | H |
| Cl | F | H | H | F | H | H |
| Cl | F | H | H | H | Cl | H |
| Cl | F | H | H | H | F | H |
| Cl | F | H | H | H | H | $OCF_2H$ |
| Cl | F | H | H | H | H | $OCH_3$ |
| F | F | H | F | H | H | H |
| F | F | H | H | $CH_3$ | H | H |
| F | F | H | H | F | H | H |
| F | F | H | H | H | F | H |
| F | F | H | H | H | H | $OCH_3$ |
| F | F | H | H | H | Cl | H |
| F | F | H | H | H | $OCH_3$ | H |
| H | F | $CF_3$ | F | H | H | H |
| H | F | $CF_3$ | H | $CH_3$ | H | H |
| H | F | $CF_3$ | H | F | H | H |
| H | F | $CF_3$ | H | H | F | H |
| H | F | $CF_3$ | H | H | H | $OCH_3$ |
| H | F | $CF_3$ | H | H | Cl | H |
| H | F | $CF_3$ | H | H | $OCH_3$ | H |
| H | F | $CH_3$ | F | H | H | H |
| H | F | $CH_3$ | H | $CH_3$ | H | H |
| H | F | $CH_3$ | H | F | H | H |
| H | F | $CH_3$ | H | H | F | H |
| H | F | $CH_3$ | H | H | H | $OCH_3$ |
| H | F | $CH_3$ | H | H | Cl | H |
| H | F | $CH_3$ | H | H | $OCH_3$ | H |
| H | F | $OCF_2H$ | F | H | H | H |
| H | F | $OCF_2H$ | H | $CH_3$ | H | H |
| H | F | $OCF_2H$ | H | F | H | H |
| H | F | $OCF_2H$ | H | H | F | H |
| H | F | $OCF_2H$ | H | H | H | $OCH_3$ |
| H | F | $OCF_2H$ | H | H | Cl | H |
| H | F | $OCF_2H$ | H | H | $OCH_3$ | H |
| $OCF_2H$ | F | H | F | H | H | H |
| $OCF_2H$ | F | H | H | $CH_3$ | H | H |
| $OCF_2H$ | F | H | H | F | H | H |
| $OCF_2H$ | F | H | H | H | F | H |
| $OCF_2H$ | F | H | H | H | H | $OCH_3$ |
| $OCF_2H$ | F | H | H | H | Cl | H |
| $OCF_2H$ | F | H | H | H | $OCH_3$ | H |
| $OCH_3$ | F | H | F | H | H | H |
| $OCH_3$ | F | H | H | $CH_3$ | H | H |
| $OCH_3$ | F | H | H | F | H | H |
| $OCH_3$ | F | H | H | H | F | H |
| $OCH_3$ | F | H | H | H | H | $OCH_3$ |
| $OCH_3$ | F | H | H | H | Cl | H |
| $OCH_3$ | F | H | H | H | $OCH_3$ | H |

As already mentioned, it could be shown that the compounds according to the present invention and the compositions according to the present invention stimulate the proliferation and/or differentiation of RPE cells. Thus, they are suitable in the treatment and/or prevention of RPE-related diseases, in particular of RPE diseases from the family of macular degeneration leading to loss of vision.

Especially good results could be obtained by the following compounds according to the present invention:

TABLE 17

| Comp. No. | Chemical structure |
|---|---|
| 34 | 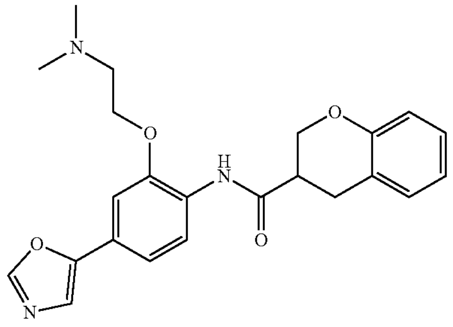 [SMILES: CN(C)CCOc1cc(-c2cnco2)ccc1NC(=O)C1COc2ccccc2C1] (racemate) |
| 35 | 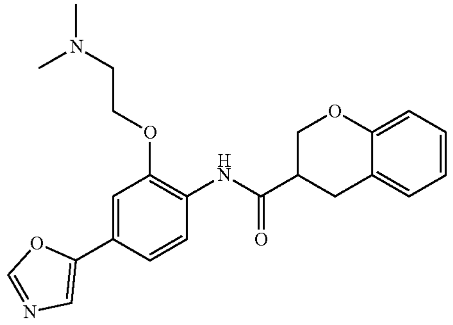 [SMILES: CN(C)CCOc1cc(-c2cnco2)ccc1NC(=O)C1COc2ccccc2C1] enantiomer with the shorter retention time from the chiral HPLC resolution |
| 36 | 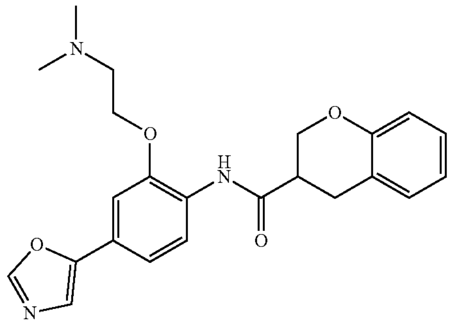 [SMILES: CN(C)CCOc1cc(-c2cnco2)ccc1NC(=O)C1COc2ccccc2C1] enantiomer with the longer retention time from the chiral HPLC resolution |
| 37 | 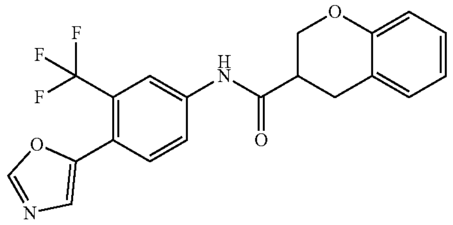 [SMILES: O=C(Nc1ccc(-c2cnco2)c(C(F)(F)F)c1)C1COc2ccccc2C1] (racemate) |

TABLE 17-continued

| Comp. No. | Chemical structure |
| --- | --- |
| 38 | 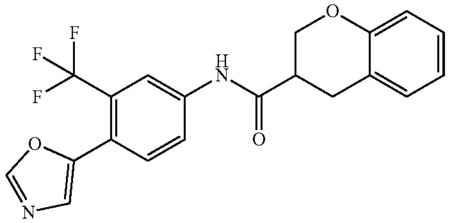 [SMILES: O=C(Nc1ccc(-c2cnco2)c(C(F)(F)F)c1)C1COc2ccccc2C1] enantiomer with the shorter retention time from the chiral HPLC resolution |
| 39 | 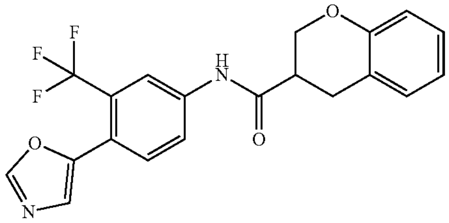 [SMILES: O=C(Nc1ccc(-c2cnco2)c(C(F)(F)F)c1)C1COc2ccccc2C1] enantiomer with the longer retention time from the chiral HPLC resolution |
| 40 | 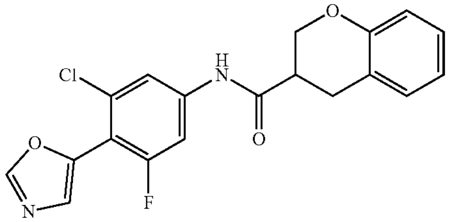 [SMILES: O=C(Nc1cc(F)c(-c2cnco2)c(Cl)c1)C1COc2ccccc2C1] enantiomer with the shorter retention time from the chiral HPLC resolution |
| 41 | 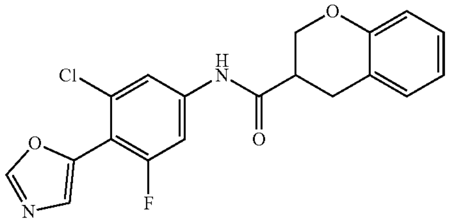 [SMILES: O=C(Nc1cc(F)c(-c2cnco2)c(Cl)c1)C1COc2ccccc2C1] enantiomer with the longer retention time from the chiral HPLC resolution |
| 42 | 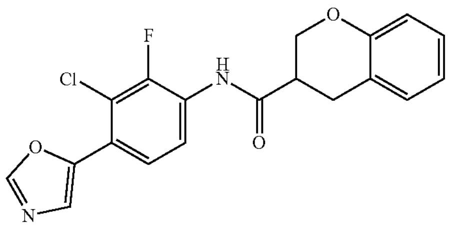 [SMILES: O=C(Nc1ccc(-c2cnco2)c(Cl)c1F)C1COc2ccccc2C1] (racemate) |
| 43 | 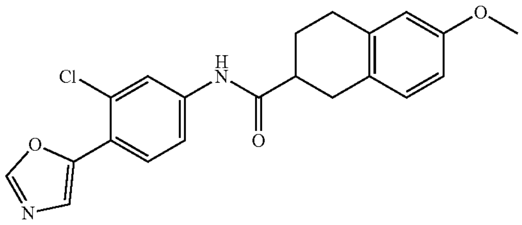 [SMILES: COc1ccc2c(c1)CCC(C(=O)Nc1ccc(-c3cnco3)c(Cl)c1)C2] (racemate) |
| 44 | 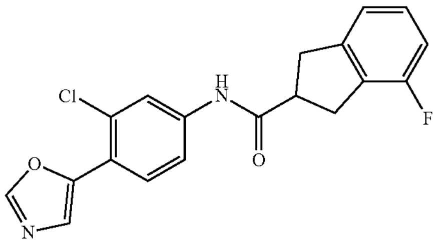 [SMILES: O=C(Nc1ccc(-c2cnco2)c(Cl)c1)C1Cc2cccc(F)c2C1] (racemate) |
| 45 | 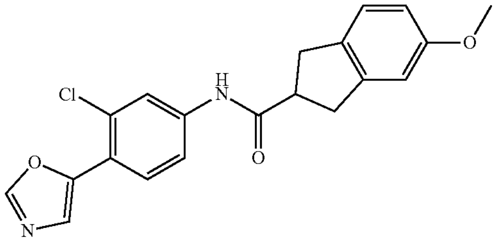 [SMILES: COc1ccc2c(c1)CC(C(=O)Nc1ccc(-c3cnco3)c(Cl)c1)C2] (racemate) |
| 46 | 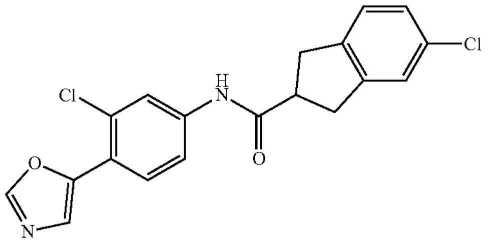 [SMILES: O=C(Nc1ccc(-c2cnco2)c(Cl)c1)C1Cc2ccc(Cl)cc2C1] (racemate) |
| 47 | 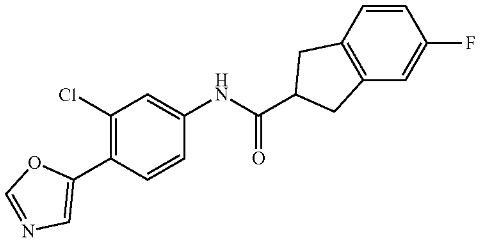 [SMILES: O=C(Nc1ccc(-c2cnco2)c(Cl)c1)C1Cc2ccc(F)cc2C1] (racemate) |

In a preferred embodiment of the present invention, the pharmaceutical composition comprises a pharmaceutically acceptable carrier and/or adjuvant; and a compound of the formula (I) as defined above, preferably a compound of formula (Ia), (Ib), (Ic), (Id), (Ie) or (If). Most preferably, it comprises a compound of formula (Ia), (Ib), (Ic), (Id), (Ie)

or (If) as disclosed in Table 11, Table 12, Table 13, Table 14, Table 15, Table 16, and Table 17 above.

EXPERIMENTAL SECTION

Cell Culture

Induced pluripotent stem cell-derived fetal RPE (iPSC-fRPE) cells acquired from the University of California, Santa Barbara, were generated from human fetal RPE cells that were isolated and reprogramed to iPSC, then differentiated and sorted for cellular markers to collect RPE progenitors. Vials were transported frozen on dry ice and stored in minus 80° C.

For the phenotypic screens, iPSC-fRPE cells were thawed and cultured in Matrigel-coated flasks with N1VA media containing 1×MEM solution supplemented with 2.2 g/L Sodium Bicarbonate, 0.25 mg/ml Taurine, 0.02 ug/ml Hydrocortisone, 0.013 ug/ml Triiodo Thyronine, 0.1 ug/ml Lipoic acid, 1% MEM Non-Essential Amino Acids, 1% Penicillin/Streptomycin, 2% Neurocult SM1 supplement and 1% N1 supplement. For the initial cultures, Thiazovivin was added to the media at 2 uM for the first 24 hr of incubation, after which the media was replaced with fresh N1VA media for additional three-day incubation at 37° C. with 5% CO2.

Compound Screens iPSC-fRPE cells were plated with N1VA media at a density of 10,000 cells per well in Matrigel-coated 96-well plates and cultured for 24 hr prior to the treatment with test compounds at a final concentration of 5 μM in 0.1% DMSO. Internal controls for each test plate were (a) 0.1% DMSO as a negative control and (b) 0.1% DMSO+10 ng/ml human recombinant bFGF (STEMCELL) as a positive control. To identify hits that promote RPE pigmentation, cells were maintained for a period of 32 days and treated with medium containing the test or control compounds according to the media exchange regimen (FIG. 1). The degree of pigmentation was quantified by measuring the light absorbance at 510 nm with Cytation5 imaging reader (BIOTEK). Compounds that increased the normalized absorbance endpoint by more than three standard deviations over the average DMSO readout per plate were considered as hits. Pigmentation values are finally reported relative to plate internal DMSO controls.

Preparation of the Compounds of the Invention

The compounds of formula (I) may be prepared by methods described below, together with synthetic methods known in the art of organic chemistry, or modifications that are familiar to those of ordinary skill in the art. The starting materials used herein are available commercially or may be prepared by routine methods known in the art, such as those methods described in standard reference books such as “Compendium of Organic Synthetic Methods, Vol. I-XIN” (published with Wiley-Interscience, ISSN: 1934-4783). Preferred methods include, but are not limited to, those described below.

The schemes are representative of methods useful in synthesizing the compounds of the present invention and the supporting examples. They are not to constrain the scope of the invention in anyway.

General Methods—Synthesis

Method 1

Scheme 1

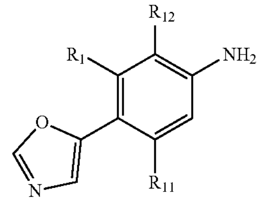

VIII

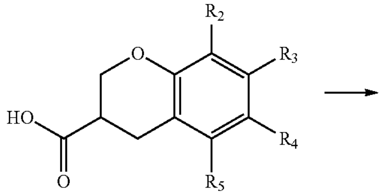

IX

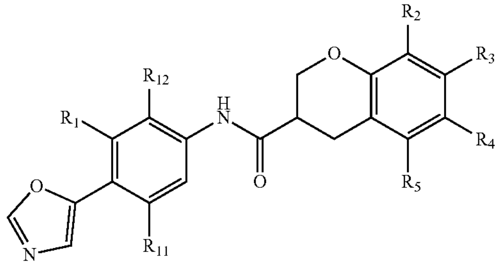

Ia where $R_1$, $R_{11}$, $R_{12}$, $R_2$, $R_3$, $R_4$ and $R_5$ are as described in formula I.

Compounds of general formula Ia (Scheme 1) may be prepared by reacting compounds of general formula VIII with a carboxylic acid of general formula IX using procedures known to chemists skilled in the art.

Method 2

Scheme 2

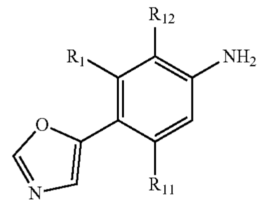

VIII

-continued

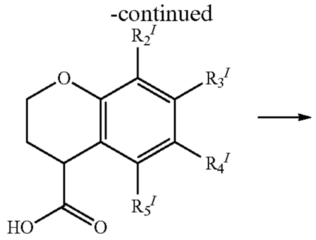

X

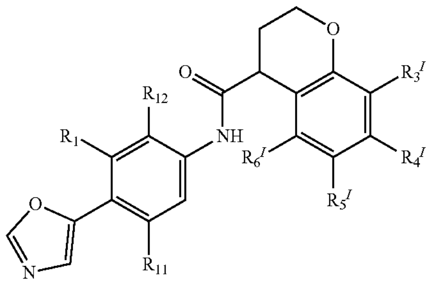

Ib

Where $R_1$, $R_{11}$, $R_{12}$, $R_2^I$, $R_3^I$, $R_4^I$ and $R_5^I$ are as described in formula I.

Compounds of general formula Ib (Scheme 2) may be prepared by reacting compounds of general formula VIII with a carboxylic acid of general formula X using procedures known to chemists skilled in the art.

Method 3

Scheme 3

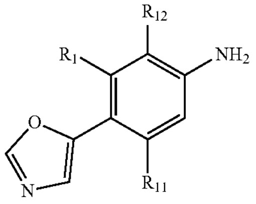

VIII

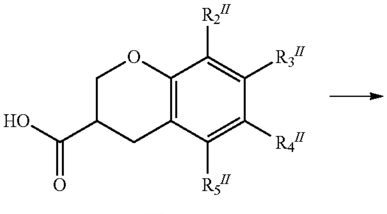

XI

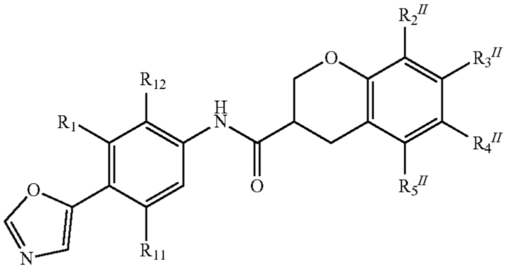

Ic where $R_1$, $R_{11}$, $R_{12}$, $R_2^{II}$, $R_3^{II}$, $R_4^{II}$ and $R_5^{II}$ are as described in formula I.

Compounds of general formula Ic (Scheme 3) may be prepared by reacting compounds of general formula VIII with a carboxylic acid of general formula XI using procedures known to chemists skilled in the art.

Method 4

Scheme 4

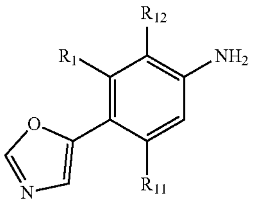

VIII

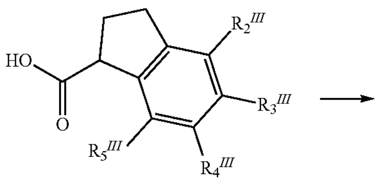

XII

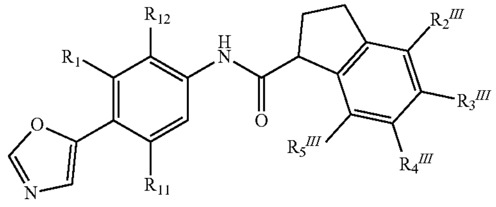

Id where $R_1$, $R_{11}$, $R_{12}$, $R_2^{III}$, $R_3^{III}$, $R_4^{III}$ and $R_5^{III}$ are as described in formula I.

Compounds of general formula Id (Scheme 4) may be prepared by reacting compounds of general formula VIII with a carboxylic acid of general formula XII using procedures known to chemists skilled in the art.

Method 5

Scheme 5

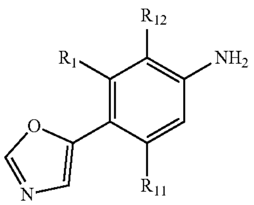

VIII

-continued

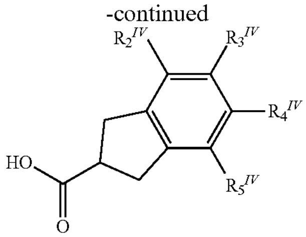

XIII

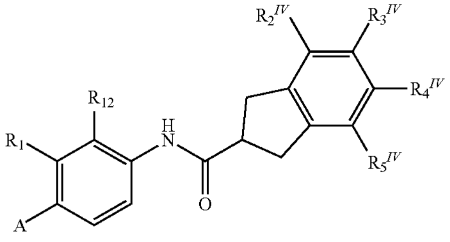

Ie where $R_1$, $R_{11}$, $R_{12}$, $R_2^{IV}$, $R_3^{IV}$, $R_4^{IV}$ and $R_5^{IV}$ are as described in formula I.

Compounds of general formula Id (Scheme 5) may be prepared by reacting compounds of general formula VIII with a carboxylic acid of general formula XIII using procedures known to chemists skilled in the art.

Method 6

Scheme 6

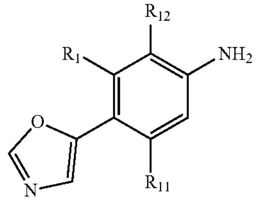

VIII

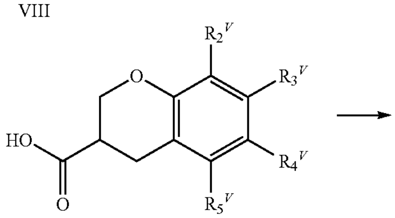

XIV

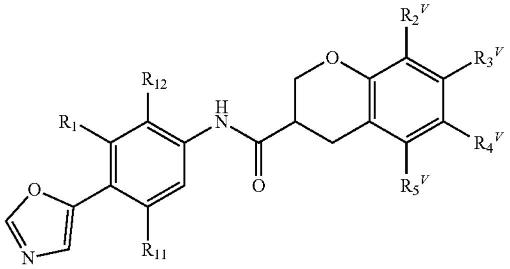

Ie where $R_1$, $R_{11}$, $R_{12}$, $R_2^V$, $R_3^V$, $R_4^V$ and $R_5^V$ are as described in formula I.

Compounds of general formula Ie (Scheme 6) may be prepared by reacting compounds of general formula VIII with a carboxylic acid of general formula XIV using procedures known to chemists skilled in the art.

Method 7

Scheme 7

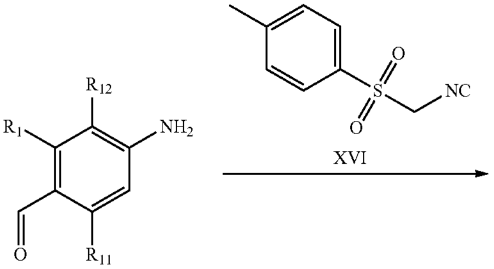

XVI

XV

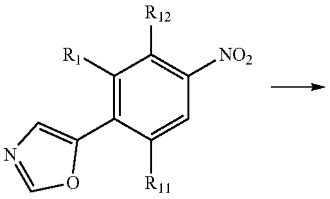

XVII

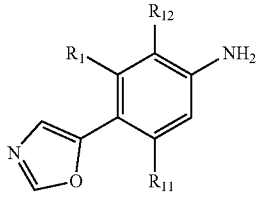

VIII where $R_1$, $R_{12}$ and $R_{11}$ are as described in formula I.

Compounds of general formula VIII (Scheme 7) may be prepared by reduction of the nitro group in compounds of general formula XVII using procedures known to chemists skilled in the art. Compounds of general formula XVII may be prepared from aldehydes of general formula XV by reaction in the presence of a reagent such as tosylmethyl isocyanide (XVI) in the presence of a base such as potassium carbonate.

Method 8

Scheme 8

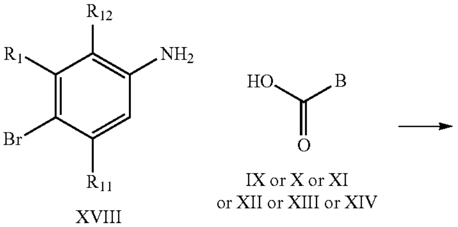

XVIII

IX or X or XI or XII or XIII or XIV

-continued

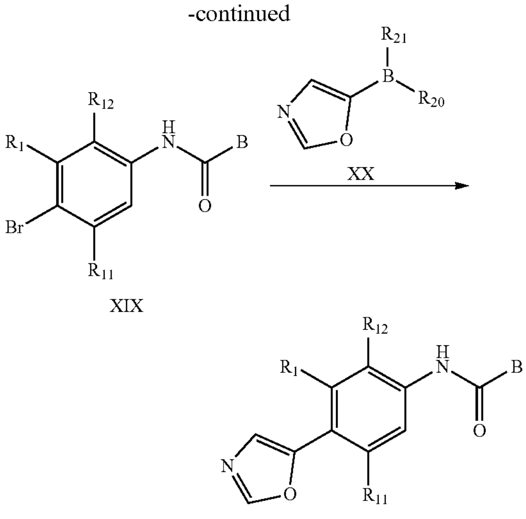

XIX XX I where $R_1$, $R_{11}$ and $R_{12}$ are as described in formula I, $R_{20}$ and $R_{21}$ are both hydroxy groups or form together with the boron atom a 4,4,5,5-tetramethyl-1,3,2-dioxaborolane group.

Compounds of general formula I (Scheme 8) may be prepared from compounds of general formulae XIX and XX in the presence of a palladium catalyst such as tetrakis (triphenylphosphin)palladium(0) and a base such as potassium carbonate or other Suzuki-Miyaura coupling reaction conditions known to chemists skilled in the art of organic synthesis. Compounds of general formula XIX may be prepared by reacting compounds of general formula from XVIII with a carboxylic acid of general formula IX-XIV using procedures known to chemists skilled in the art.

Analytic Methods $^1H$ NMR spectra were recorded in DMSO-$d_6$/$CD_3OD$/$CDCl_3$ solution in 5 mm o.d. tubes [Wilmad NMR tubes (Sigma-Aldrich), 5 mm Thin Wall, 7" Length] at 300.0 K and were collected on Bruker Avance NMRS-400 at 400 MHz for $^1H$. The chemical shifts (5) are relative to $CDCl_3$ ($CDCl_3$=7.26 ppm), DMSO-$d_6$ (DMSO-$d_6$=2.5 ppm), $CD_3OD$ ($CD_3OD$=3.3 ppm) and expressed in ppm. The chemical shifts in $CDCl_3$, DMSO-$d_6$ and $CD_3OD$ are relative to tetramethylsilane (TMS, =0.00 ppm) and expressed in ppm.

Analytical HPLC

Analytical HPLC Method A: Chromegabond WR C18 (3 cm×3.2 mm, 3μ) column operated with a flow rate of 1.5 mL/min. As mobile phases, 0.02% TFA in water (mobile phase C) and 0.02% TFA in $CH_3CN$ (mobile phase D) were used in a gradient starting at 90% C and 10% D, changed to 10% C and 90% D in 3.0 min, then to 90% C and 10% D in 4.0 min, which was held constant up to 5.1 min.

Analytical HPLC Method B: Restek Ultra AQ C18 (30×2.1 mm, 3u) column operated with a flow rate of 1.5 mL/min. As mobile phases, 0.05% HCOOH in water (mobile phase A) and $CH_3CN$ (mobile phase B) were used in a gradient starting at 98% A and 2% B held for 0.75 min, then to 90% A and 10% B in 1.5 min, further to 2% A and 98% B in 3.0 min, held this mobile phase composition up to 4.0 min and finally back to initial condition at 5.0 min.

Analytical HPLC Method C: Column-YMC TRIART C18 (33×2.1 mm, 3μ), (mobile phase: 95% [0.01% HCOOH in water] and 5% [0.01% HCOOH in $CH_3CN$] held for 0.50 min then to 99% [0.01% HCOOH in water] and 1% [0.01% HCOOH in $CH_3CN$] in 3.0 min, held this mobile phase composition up to 4.0 min, and finally back to initial condition in 4.10 min, held this mobile phase composition up to 4.50 min). Flow=1.0 ml/min.

Preparative HPLC

Preparative HPLC Method A: Waters Sunfire C18 OBD Prep Column, 100 A, 5 μm, 19 mm×100 mm with SunFire C18 Prep Guard Cartridge, 100 A, 10 μm, 19 mm×10 mm was used. Deionized Water (phase A) and HPLC-grade Methanol (phase B) were used as an eluent.

Preparative HPLC Method B: Waters auto purification instrument with a YMC Triart C18 (250×21.2 mm, 5μ) column operated at room temperature with a flow rate of 16 mL/min. Samples were eluted with 20 mM ammonium bicarbonate in water (mobile phase A) and acetonitrile (mobile phase B) and a gradient profile of 70% A and 30% B initially, then 45% A and 55% B in 3 min, adapted to 20% A and 80% B in 20 min, then to 5% A and 95% B in 21 min, which was held constant for 2 min. Pure fractions were concentrated to yield the final product.

Methods for Chiral Separation

Chiral Analytical Methods

Chiral Separation Method A: Separation was accomplished using Agilent Prep-HPLC, Column: Regis Reflect C-Amylose A containing Amylose tris(3,5-dimethylphenylcarbamate) (250×30 mm, 5μ), Flow: 35 g/min, Mobile Phase: 35% $CO_2$+65% (0.1% NH3 in MeOH), ABPR: 100 bar, Temperature: 35° C.

Chiral Separation Method B: Separation was accomplished using Agilent Prep-HPLC, Column: Daicel Chiralpak IG (250×20 mm) containing tris(3-chloro-5 methylphenylcarbamate) substituted amylose immobilized on 5 μm silica; Flow: 25 g/min, Mobile Phase: 45% $CO_2$+55% (0.1% NH3 in MeOH), ABPR: 120 bar, Temperature: 35° C.

Chiral Separation Method C: Separation was accomplished using: Column: Regis Reflect C-Amylose A containing Amylose tris(3,5-dimethylphenylcarbamate) (250×30 mm, 5μ), Mobile phase: 40% CO2+60% (0.1% ammonia in MeOH), Flow rate: 25.0 g/min, Run time: 10 min, Wave length: 220 nm, ABPR: 110 bar, Temperature: 35° C.

Chiral Separation Method D: Separation was accomplished using Agilent Prep-HPLC, Column: Chiralpak IG (250×30 mm, 5μ), Flow: 35 g/min, Mobile Phase: 35% $CO_2$+65% (0.1% NH3 in MeOH), ABPR: 100 bar, Temperature: 35° C.

Chiral Separation Method E: Separation was accomplished using Agilent Prep-HPLC, Column: Chiralpak IG (250×30 mm, 5μ), Flow: 25 g/min, Mobile Phase: 60% $CO_2$+40% (0.1% NH3 in MeOH), ABPR: 100 bar, Temperature: 35° C.

Chiral Separation Method F: Separation was accomplished using Agilent Prep-HPLC, Column: Chiralpak IG (250×30 mm, 5μ), Flow: 25 g/min, Mobile Phase: 45% $CO_2$+55% (0.1% NH3 in MeOH), ABPR: 120 bar, Temperature: 35° C.

Chiral Separation Method G: Separation was accomplished using column: Chiralpak AD-H (4.6×250 mm, 5μ); Mobile Phase: 100% EtOH; Flow Rate: 0.5 ml/min; Column Temperature: 24° C.; Wavelength: 286 nm.

Chiral Preparative Methods

Chiral Separation Method H: performed using a Daicel Chiralpak AD-H (250×20 mm×5 μm) column coated with amylose-tris(3,5-dimethylphenylcarbamate); Mobile phase: Hexane-IPA-MeOH, 70-15-15 Flow Rate: 12 mL/min; Column Temperature: 24° C.; Wavelength: 210 nm, 225 nm, 254 nm.

Chiral Separation Method I: performed using a Daicel Chiralpak AD-H (250×20 mm×5 μm) column coated with amylose-tris(3,5-dimethylphenylcarbamate); Mobile phase: Hexane-IPA-MeOH, 70-15-15 Flow Rate: 12 mL/min; Column Temperature: 24° C.; Wavelength: 215 nm, 280 nm.

Chiral Separation Method K: performed using a Daicel Chiralpak AD-H (250×20 mm×5 μm) column coated with amylose-tris(3,5-dimethylphenylcarbamate); Mobile phase: EtOH, Flow Rate: 10 mL/min; Column Temperature: 24° C.; Wavelength: 286 nm.

General Synthetic Procedures

Coupling procedure A: the carboxylic acid (1.1 mmol) and a solution of N-hydroxybenzotriazole in DMSO (100 g/L, 2 mL, 1.5 mmol) were placed in a vial, and the aniline derivative (1 mmol) was added. If amine was used as a hydrochloride, $Et_3N$ (1 mmol) was also added. The reaction mixture was stirred for 30 min in a shaker, and EDC (1.2 mmol) was added. After all the reagents were loaded, the vial was sealed and stirred in a shaker for 1 h. If clear solution was formed, the vial was left at room temperature for 24 h. Otherwise, the reaction mixture was kept in a sonication bath for 24 h (strong heating should be avoided). If strong thickening of the reaction mixture was observed so that stirring was not effective, 0.2 mL of DMSO might be added in one portion. The crude reaction mixture was analyzed by LC-MS and then subjected to chromatographic purification. The purification was performed using Agilent 1260 Infinity systems equipped with DAD and mass-detector.

Synthesis of Intermediates

Preparation of 5-(2-methoxy-4-nitrophenyl)oxazole

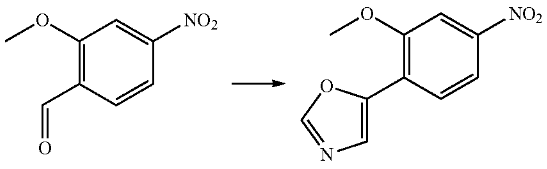 [SMILES: COc1cc([N+](=O)[O-])ccc1C=O ; COc1cc([N+](=O)[O-])ccc1-c1cnco1]

To a stirred solution of 2-methody-4-nitrobenzaldehyde (3.00 g, 16.6 mmol) in methanol (20 mL) was added 1-(isocyanomethane)sulfonyl-4-methylbenzene (3.80 g, 19.9 mmol) followed by $K_2CO_3$ (8.00 g, 58.0 mmol) and the reaction mixture was heated to 80° C. for 2 h. After completion of the reaction, reaction mass was poured into sat $NaHCO_3$ solution (20 mL) and extracted into ethyl acetate (3×100 mL). The organic layer was washed with water, brine, dried over anhydrous sodium sulphate and concentrated under vacuum to get a crude which was purified by flash silica gel chromatography (eluted at 30% ethyl acetate in hexane) to get 5-(2-methoxy-4-nitrophenyl)-1,3-oxazole (2.1 g, 57%). LCMS: 221 (M+H).

Preparation of 3-methoxy-4-(1,3-oxazol-5-yl)aniline

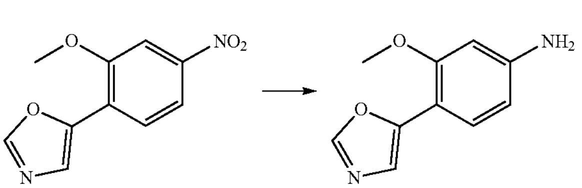 [SMILES: COc1cc([N+](=O)[O-])ccc1-c1cnco1 ; COc1cc(N)ccc1-c1cnco1]

To a stirred solution of 5-(2-methoxy-4-nitrophenyl)-1,3-oxazole (1.00 g, 4.52 mmol) in ethanol (20 mL) were added tin(II) chloride (5.14 g, 27.1 mmol) and conc. HCl (6 mL) solution drop wise at 0° C. and then stirred for 6 h at room temperature. After completion of the reaction, the reaction mixture was diluted with sat. $NaHCO_3$ solution (20 mL), extracted with ethyl acetate (3×200 mL) and the organic layer was washed with water, brine, dried over anhydrous sodium sulphate and concentrated under vacuum to get crude of 3-methoxy-4-(1,3-oxazol-5-yl)aniline (700 mg, 81%). LCMS: 191 (M+H).

Preparation of 5-(2-chloro-4-nitrophenyl)-1,3-oxazole

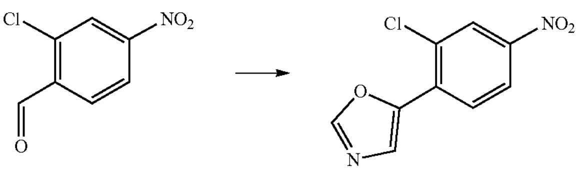 [SMILES: O=Cc1ccc([N+](=O)[O-])cc1Cl ; O=[N+]([O-])c1ccc(-c2cnco2)c(Cl)c1]

To a stirred solution of 2-chloro-4-nitrobenzaldehyde (3 g, 16.16 mmol) and 1-(isocyanomethane)sulfonyl-4-methylbenzene (4.1 g, 21.0 mmol) in MeOH (30 mL) was added $K_2CO_3$ (8.9 g, 64.66 mmol) and the reaction mixture was heated to 80° C. for 2 h. After completion of the reaction, the reaction mass was poured into saturated $NaHCO_3$ solution (20 mL) and extracted with ethyl acetate (2×50 mL). The organic layer was washed with water, brine, dried over anhydrous sodium sulphate and concentrated under vacuum to get a crude which was purified by flash silica gel chromatography (eluted with 30% ethyl acetate in hexane) to afford 5-(2-chloro-4-nitrophenyl)-1,3-oxazole (2.1 g, 57%). LCMS: 225.2 (M+H).

Preparation of 3-chloro-4-(1,3-oxazol-5-yl)aniline

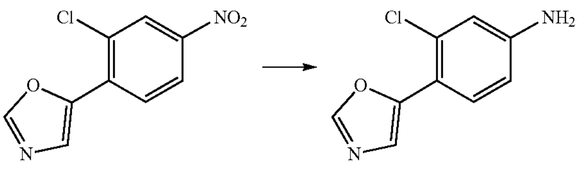 [SMILES: O=[N+]([O-])c1ccc(-c2cnco2)c(Cl)c1 ; Nc1ccc(-c2cnco2)c(Cl)c1]

To a stirred solution of 5-(2-chloro-4-nitrophenyl)-1,3-oxazole (3 g, 13.4 mmol) in EtOH (40 mL) were added tin(II) chloride dihydrate (12.08 g, 53.57 mmol) and conc. HCl (5 mL) dropwise at 0° C. and the reaction mixture was stirred for 30 min at 80° C. After completion of the reaction, the reaction mass was neutralized using a 2N NaOH solution and extracted with ethyl acetate (2×50 mL). The organic layer was thoroughly washed with water, dried over anhydrous sodium sulphate and concentrated under vacuum to afford 3-chloro-4-(1,3-oxazol-5-yl)aniline (1.5 g, 57%). LCMS: 195 (M+H).

Preparation of 5-(2-fluoro-4-nitrophenyl)-1,3-oxazole

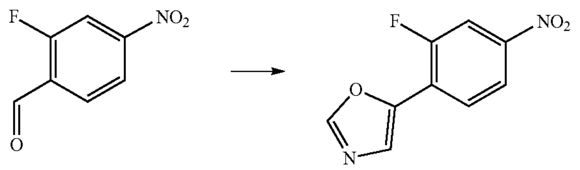 [SMILES: O=Cc1ccc([N+](=O)[O-])cc1F ; O=[N+]([O-])c1ccc(-c2cnco2)c(F)c1]

To a stirred solution of 2-fluoro-4-nitro benzaldehyde (5 g, 29.56 mmol) and 1-(isocyanomethane)sulfonyl-4-methylbenzene (7.5 g, 38.43 mmol) in MeOH (35 mL) was added $K_2CO_3$ (16.3 g, 118.27 mmol) and the reaction mixture was heated to 80° C. for 2 h. After completion of the reaction, reaction mass was poured into saturated $NaHCO_3$ solution (50 mL) and extracted with ethyl acetate (2×50 mL). The organic layer was washed with water, brine, dried over anhydrous sodium sulphate and concentrated under vacuum to get a crude which was purified by flash silica gel chromatography (eluted with 30% ethyl acetate in hexane) to afford 5-(2-fluoro-4-nitrophenyl)-1,3-oxazole (2.5 g, 40%). LCMS: 209.2 (M+H).

Preparation of 3-fluoro-4-(1,3-oxazol-5-yl)aniline

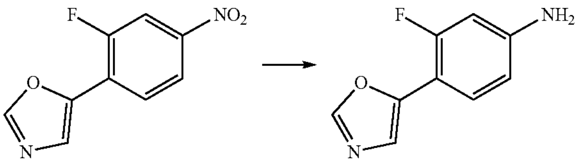 [SMILES: O=[N+]([O-])c1ccc(-c2cnco2)c(F)c1 ; Nc1ccc(-c2cnco2)c(F)c1]

To a stirred solution of 5-(2-fluoro-4-nitrophenyl)-1,3-oxazole (700 mg, 3.36 mmol) in EtOH (35 mL) were added tin(II) chloride dihydrate (3.03 g, 13.46 mmol) and conc. HCl (2 mL) dropwise at 0° C. and the reaction mixture was stirred for 30 min at 80° C. After completion of the reaction, the reaction mass was neutralized with a 2N NaOH solution and extracted with ethyl acetate (2×50 mL). The organic layer was thoroughly washed with water, dried over anhydrous sodium sulphate and concentrated under vacuum to afford 3-fluoro-4-(1,3-oxazol-5-yl)aniline (350 mg, 53%).

LCMS: 179 (M+H).

Preparation of 5-(2-methyl-4-nitrophenyl)oxazole

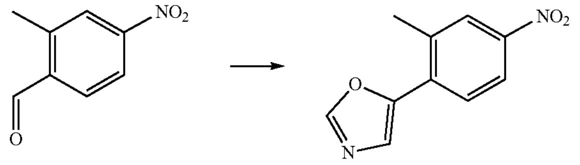

To a stirred solution of 2-methyl-4-nitrobenzaldehyde (1.02 g, 6.05 mmol) and 1-(isocyanomethane)sulfonyl-4-methylbenzene (1.36 g, 7.05 mmol) in MeOH (25 mL) was added potassium carbonate (1.67 g, 12.1 mmol) and the reaction mixture was heated to reflux for 2 h. After consumption of starting material by TLC, the reaction mixture was cooled to room temperature, the solvent was evaporated under reduced pressure, the residue was treated with saturated aqueous solution of $NaHCO_3$ (20 mL), and extracted with ethyl acetate (3×30 mL). The organic layer was washed with water (30 mL), brine (20 mL), dried over anhydrous $Na_2SO_4$, and concentrated under reduced pressure to get crude which was purified by flash column chromatography to get 5-(2-methyl-4-nitrophenyl)oxazole (1.2 g, 91%).

Preparation of 3-methyl-4-(oxazol-5-yl)aniline

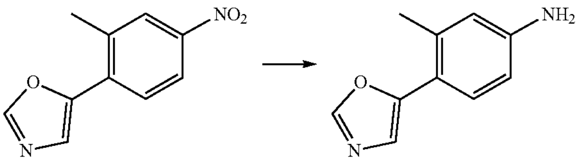

To a stirred solution of 5-(2-methyl-4-nitrophenyl)oxazole (1.1 g, 5.39 mmol) in ethanol (20 mL) was added tin(II) chloride dihyrate (4.08 g, 21.5 mmol) at room temperature. The mixture was cooled to 0° C. and conc. HCl (3.0 mL) was added drop wise. The reaction mixture was then stirred for 0.5 h at 80° C. After completion of the reaction by TLC, the reaction mixture was cooled to room temperature, diluted with saturated aqueous solution of $NaHCO_3$ solution (30 mL), and extracted with ethyl acetate (3×30 mL). Organic layers were combined, washed with water (20 mL), brine (15 mL), dried over anhydrous $Na_2SO_4$, and concentrated under reduced pressure. The crude was purified by column chromatography to get 3-methyl-4-(oxazol-5-yl)aniline (610 mg, 65%).

Preparation of 5-(3-methyl-4-nitrophenyl)oxazole

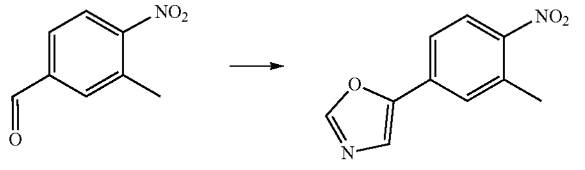

To a stirred solution of 3-methyl-4-nitrobenzaldehyde 2.01 g, 12.1 mmol) and 1-(isocyanomethane)sulfonyl-4-methylbenzene (2.6 g, 13.3 mmol) in MeOH (50 mL) was added $K_2CO_3$ (3.34 g, 24.2 mmol) and the reaction mixture was heated to reflux for 2 h. After complete consumption of starting material by TLC, the reaction was cooled to room temperature, solvent was evaporated under reduced pressure, the residue was treated with saturated aqueous solution of $NaHCO_3$ (40 mL), and extracted with ethyl acetate (3×40 mL). The organic layers were combined, washed with water (30 mL) and brine (20 mL), dried over $Na_2SO_4$, and concentrated under reduced pressure. The crude was purified by column chromatography using silica (to get 5-(3-methyl-4-nitrophenyl)oxazole (1.9 g, 76%).

Preparation of 2-methyl-4-(oxazol-5-yl)aniline

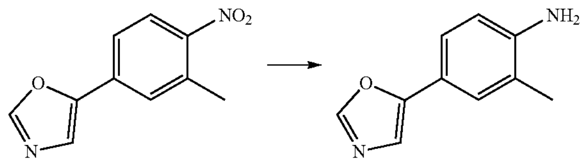

To a stirred solution of 5-(3-methyl-4-nitrophenyl)oxazole (1.8 g, 5.39 mmol) in methanol (20 mL) was added Raney-Nickel (2.0 g) at room temperature. The reaction mixture was stirred under $H_2$ atmosphere for 18 h. After complete consumption of starting material, reaction mixture was filtered through a bed of celite and the filtrate was concentrated under reduced pressure. The crude was purified by column chromatography to get 2-methyl-4-(oxazol-5-yl) aniline (1.3 g, 84%).

LCMS:174.7 (M+H)

Preparation of 5-(4-nitro-2-(trifluoromethyl)phenyl)oxazole

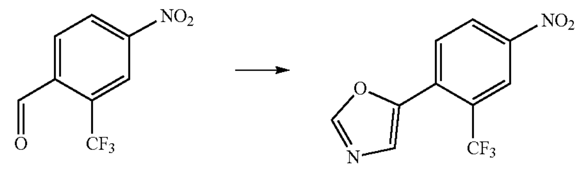 [SMILES: O=Cc1ccc([N+](=O)[O-])cc1C(F)(F)F ; O=[N+]([O-])c1ccc(-c2cnco2)c(C(F)(F)F)c1]

To a stirred solution of 4-nitro-2-(trifluorometyl)benzaldehyde (2.0 g, 9.13 mmol) and 1-(isocyanomethane)sulfonyl-4-methylbenzene (2.05 g, 10.5 mmol) in MeOH (50 mL) was added $K_2CO_3$ (2.52 g, 18.26 mmol) and the reaction mixture was heated to reflux for 2 h. After consumption of starting material by TLC, the reaction mixture was cooled to room temperature, the solvent was evaporated under reduced pressure, the residue was treated with saturated aqueous solution of $NaHCO_3$ (20 mL), and extracted with ethyl acetate (3x30 mL). The organic layer was washed with water (30 mL), brine (20 mL), dried over $Na_2SO_4$, and concentrated under reduced pressure to get crude which was purified by column chromatography to get 5-(4-nitro-2-(trifluoromethyl)phenyl)oxazole (1.66 g, 72%).

Preparation of 4-(oxazol-5-yl)-3-(trifluoromethyl)aniline

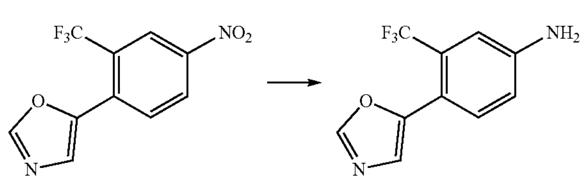 [SMILES: O=[N+]([O-])c1ccc(-c2cnco2)c(C(F)(F)F)c1 ; Nc1ccc(-c2cnco2)c(C(F)(F)F)c1]

To a stirred solution of 5-(4-nitro-2-(trifluoromethyl)phenyl)oxazole (1.545 g, 5.99 mmol) in ethanol (30 mL) was added tin(II) chloride dihydrate (5.40 g, 23.95 mmol) at room temperature. The mixture was cooled to 0° C. and conc. HCl (3.5 mL) was added drop wise. The reaction mixture was then stirred for 2.0 h at 80° C. After completion of the reaction by TLC, the reaction mixture was cooled to room temperature, diluted with saturated aqueous solution of $NaHCO_3$ (70 mL), and extracted with ethyl acetate (3x50 mL). Organic layers were combined, washed with water (40 mL), brine (30 mL), dried over anhydrous $Na_2SO_4$, and concentrated under reduced pressure. The crude was purified by column chromatography to get 4-(oxazol-5-yl)-3-(trifluoromethyl)aniline (1.13 mg, 83%).

Preparation of Chroman-3-carbonyl chloride

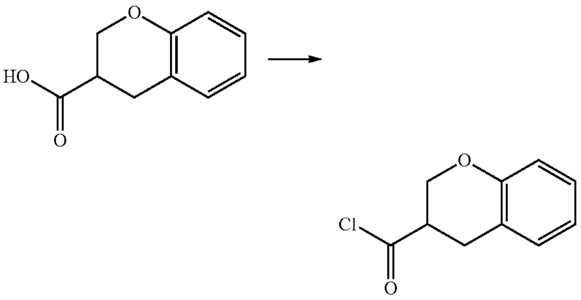

To a solution of chroman-3-carboxylic acid (750 mg, 4.21 mmol) in dry dichloromethane (10 mL) was added thionyl chloride (0.45 mL, 6.32 mmol) at 0° C. followed by DMF (catalytic). After the addition, the reaction mixture was warmed to room temperature and heated to reflux for 2.0 h. The reaction mass was cooled to room temperature, the solvent was evaporated under reduced pressure, and dried under vacuum.

Preparation of N-(4-bromo-2-(difluoromethoxy) phenyl)chroman-3-carboxamide

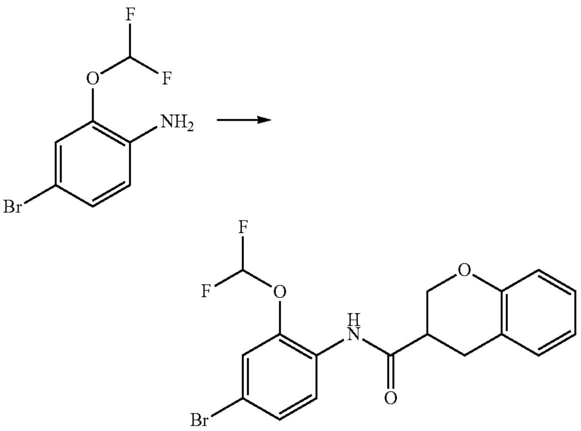

A solution of chroman-3-carbonyl chloride in dry dichloromethane (10 mL) was added to the mixture of 4-bromo-2-(difluoromethoxy)aniline (600 mg, 2.521 mmol) and triethylamine (1.1 mL, 7.563 mmol) in dry dichloromethane (10 mL) at 0° C. After the addition, reaction was slowly warmed to room temperature over 3 h. The reaction was diluted with dichloromethane (5 mL), washed with water (10 mL) and brine (15 mL), dried over $Na_2SO_4$, and concentrated under reduced pressure to get crude. Purification of the crude by column chromatography gave N-(4-bromo-2-(difluoromethoxy)phenyl)chroman-3-carboxamide (520 mg, 62%).

Preparation of 5-(3-methoxy-4-nitrophenyl)oxazole

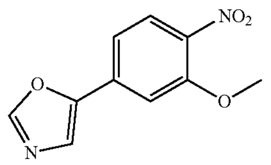 [SMILES: COc1cc(-c2cnco2)ccc1[N+](=O)[O-]]

To a stirred solution of 3-methoxy-4-nitrobenzaldehyde (2.5 g, 13.80 mmol) and toluenesulfonylmethyl isocyanide (3.1 g, 15.87 mmol) in MeOH (60 mL) was added $K_2CO_3$ (3.8 g, 27.60 mmol) and the reaction mixture was heated to reflux for 2 h. After consumption of starting material by TLC, the reaction mixture was cooled to room temperature, the solvent was evaporated under reduced pressure, the residue was treated with saturated aqueous solution of $NaHCO_3$ (40 mL), and extracted with ethyl acetate (3x40 mL). The organic layer was washed with water (40 mL), brine (30 mL), dried over $Na_2SO_4$, and concentrated under reduced pressure to get the crude product which was triturated with dichloromethane/hexane to get 5-(3-methoxy-4-nitrophenyl)oxazole (2.4 g, 78%).

Preparation of 2-nitro-5-(oxazol-5-yl)phenol

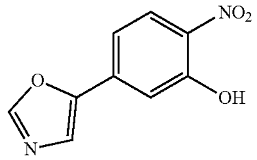 [SMILES: O=[N+]([O-])c1ccc(-c2cnco2)cc1O]

To a stirred solution of 5-(3-methoxy-4-nitrophenyl)oxazole (2.0 g, 9.09 mmol) in dry dichloromethane (50 mL) was added $BBr_3$ (1M in dichloromethane, 22.7 mL, 22.72 mmol) at 0° C. under $N_2$. The resulting mixture was allowed to warm to room temperature and stirred for 2 h. After consumption of starting material by TLC, the reaction mixture was quenched with ice water (30 mL) and stirred for 30 min at room temperature. The reaction mixture was filtered and the solids were washed with dichloromethane (2x25 mL). The filtrate was washed with water (30 mL), brine (20 mL) dried over $Na_2SO_4$ and concentrated under reduced pressure. The crude was purified by column chromatography using silica gel to get 2-nitro-5-(oxazol-5-yl)phenol (1.7 g, 90%) as solid.

Preparation of N-dimethyl-2-(2-nitro-5-(oxazol-5-yl)phenoxy)ethanamine

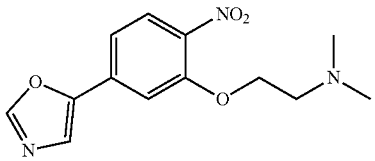

A mixture of 2-nitro-5-(oxazol-5-yl)phenol (1.65 g, 8.01 mmol), dimethylaminoethyl chloride hydrochloride (1.9 g, 13.2 mmol), $K_2CO_3$ (6.6 g, 47.7 mmol), potassium iodine (215 mg, 1.29 mmol), and DMF (35 mL) was heated at 100° C. for 2 h. The reaction was monitored by TLC (part of the starting materials remained unreacted), the reaction mixture was cooled to room temperature, and concentrated. The residue was diluted with saturated aqueous solution of $NH_4Cl$ (20 mL), extracted with ethyl acetate (3x50 mL), the organic layer was washed with water (50 mL), brine (40 mL), dried over anhydrous $Na_2SO_4$, and concentrated under reduced pressure. The crude was purified by column chromatography to get N,N-dimethyl-2-(2-nitro-5-(oxazol-5-yl)phenoxy)ethanamine (750 mg) as solid.

Preparation of 2-(2-(dimethylamino)ethoxy)-4-(oxazol-5-yl) aniline

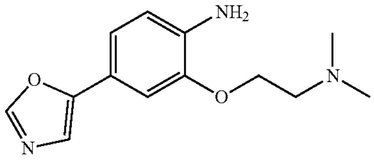 [SMILES: CN(C)CCOc1cc(-c2cnco2)ccc1[N+](=O)[O-]]

To a stirred solution of N,N-dimethyl-2-(2-nitro-5-(oxazol-5-yl)phenoxy)ethanamine (725 mg, 2.62 mmol) in ethanol (20 mL) was added tin(II) chloride dihydrate (2.95 g, 13.08 mmol) and the reaction mixture was heated to 65-70° C. for 1.5 h. After consumption of starting material by TLC, the reaction mixture was cooled room temperature, basified with saturated aqueous solution of $Na_2CO_3$ (45 mL), diluted with dichloromethane (60 mL), and aqueous phase was extracted with dichloromethane (3x30 mL). The organic layers were combined, dried over $Na_2SO_4$, and concentrated under reduced pressure. The crude was purified by column chromatography to get 2-(2-(dimethylamino)ethoxy)-4-(oxazol-5-yl)aniline (575 mg, 86%).

Preparation of 5-(4-nitro-2-(trifluoromethyl)phenyl)oxazole

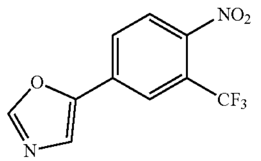 [SMILES: O=[N+]([O-])c1ccc(-c2cnco2)cc1C(F)(F)F]

To a stirred solution of 4-nitro-2-(trifluorometyl)benzaldehyde (2.0 g, 9.13 mmol) and toluenesulfonylmethyl isocyanide (2.05 g, 10.5 mmol) in MeOH (50 mL) was added $K_2CO_3$ (2.52 g, 18.26 mmol) and the reaction mixture was heated to reflux for 2 h. After consumption of starting material by TLC, the reaction mixture was cooled to room temperature, the solvent was evaporated under reduced pressure, the residue was treated with saturated aqueous solution of $NaHCO_3$ (20 mL), and extracted with ethyl acetate (3x30 mL). The organic layer was washed with water (30 mL), brine (20 mL), dried over $Na_2SO_4$, and concentrated under reduced pressure to get the crude product which was purified by column chromatography to get 5-(4-nitro-2-(trifluoromethyl)phenyl)oxazole (1.66 g, 72%) as solid.

Preparation of 4-(oxazol-5-yl)-3-(trifluoromethyl)aniline

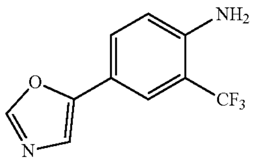 [SMILES: Nc1ccc(-c2cnco2)cc1C(F)(F)F]

To a stirred solution of 5-(4-nitro-2-(trifluoromethyl)phenyl)oxazole (1.545 g, 5.99 mmol) in ethanol (30 mL) was added tin(II) chloride dihydrate (5.40 g, 23.95 mmol) at room temperature. The mixture was cooled to 0° C. and conc. HCl (3.5 mL) was added drop wise. The reaction mixture was then stirred for 2.0 h at 80° C. After completion of the reaction by TLC, the reaction mixture was cooled to room temperature, diluted with saturated aqueous solution of $NaHCO_3$ solution (70 mL), and extracted with ethyl acetate (3×50 mL). Organic layers were combined, washed with water (40 mL), brine (30 mL), dried over anhydrous $Na_2SO_4$, and concentrated under reduced pressure. The crude was purified by column chromatography to get 4-(oxazol-5-yl)-3-(trifluoromethyl)aniline (1.13 g, 83%).

Preparation of N-(4-bromo-3-chloro-5-fluorophenyl) chroman-3-carboxamide

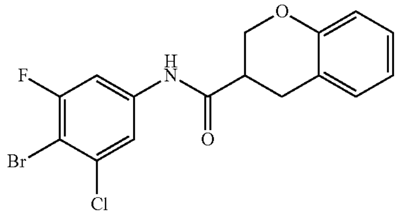 [SMILES: O=C(Nc1cc(F)c(Br)c(Cl)c1)C1COc2ccccc2C1]

A solution of chroman-3-carbonyl chloride in dry dichloromethane (10 mL) was added to the mixture of 4-bromo-3-chloro-5-fluoroaniline (300 mg, 1.34 mmol) and triethylamine (0.56 mL, 4.00 mmol) in dry dichloromethane (10 mL) at 0° C. After the addition, reaction was slowly warmed to room temperature over 3 h. The reaction was diluted with dichloromethane (10 mL), washed with water (10 mL) and brine (15 mL), dried over $Na_2SO_4$, and concentrated under reduced pressure to get crude. Purification of the crude by column chromatography gave N-(4-bromo-3-chloro-5-fluorophenyl)chroman-3-carboxamide (280 mg, 49%) as solid.

Preparation of N-(4-bromo-3-chloro-2-fluorophenyl) chroman-3-carboxamide

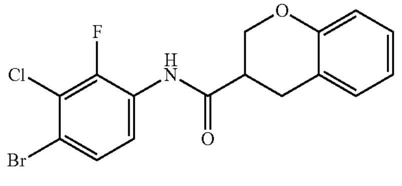 [SMILES: O=C(Nc1ccc(Br)c(Cl)c1F)C1COc2ccccc2C1]

A solution of chroman-3-carbonyl chloride in dry dichloromethane (10 mL) was added to the mixture of 4-bromo-3-chloro-2-fluoroaniline (600 mg, 2.673 mmol) and triethylamine (1.1 mL, 8.02 mmol) in dry dichloromethane (10 mL) at 0° C. After the addition, reaction was slowly warmed to room temperature over 3 h. The reaction mixture was monitored by TLC. After maximum conversion, the reaction mixture was diluted with dichloromethane (5 mL), washed with water (10 mL) and brine (15 mL), dried over sodium sulphate, and concentrated under reduced pressure to get crude N-(4-bromo-3-chloro-2-fluorophenyl) chroman-3-carboxamide. Purification of the crude by column chromatography gave N-(4-bromo-3-chloro-2-fluorophenyl)chroman-3-carboxamide (320 mg, 31.2%) as solid.

Compound (1): first (−)-N-(3-chloro-4-(1,3-oxazol-5-yl)phenyl)chromane-3-carboxamide

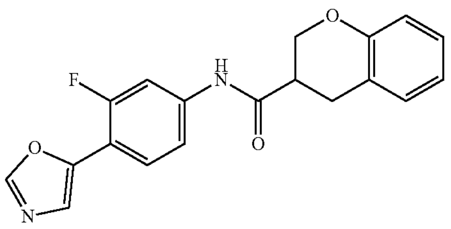 [SMILES: O=C(Nc1ccc(-c2cnco2)c(F)c1)C1COc2ccccc2C1]

To a stirred solution of 3-chloro-4-(oxazol-5-yl)aniline (100 mg, 0.51 mmol) and chromane-3-carboxylic acid (109 mg, 0.61 mmol) in DMF (1 mL) were added DIPEA (0.26 mL) and HATU (392 mg, 1.03 mmol) at room temperature and the reaction was stirred for 16 h at room temperature. After completion of the reaction, the reaction mixture was purified by preparative HPLC to yield N-(3-chloro-4-(1,3-oxazol-5-yl)phenyl)chromane-3-carboxamide (34 mg, 18%). The racemic product was separated by chiral chromatography using Chiral Separation Method C to yield Compound (1), which is characterized by retention time=4.76 min (first eluted from the column).

Analytical HPLC Method A. Rt: 1.73 min; MS: 355 (M+H).

$[\alpha]_D^{25}$=−7.57 (589 nm, c=0.49, DMSO).

Compound (2): second (+)-N-(3-chloro-4-(1,3-oxazol-5-yl)phenyl)chromane-3-carboxamide

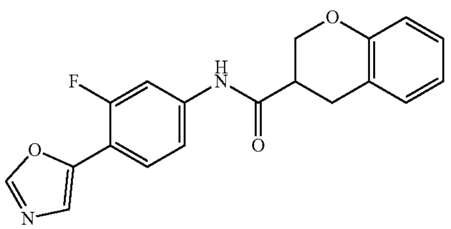 [SMILES: O=C(Nc1ccc(-c2cnco2)c(F)c1)C1COc2ccccc2C1]

To a stirred solution of 3-chloro-4-(oxazol-5-yl)aniline (100 mg, 0.51 mmol) and chromane-3-carboxylic acid (109 mg, 0.61 mmol) in DMF (1 mL) were added DIPEA (0.26 mL) and HATU (392 mg, 1.03 mmol) at room temperature and the reaction was stirred for 16 h at room temperature. After completion of the reaction, the reaction mixture was purified by preparative HPLC to yield N-(3-chloro-4-(1,3-oxazol-5-yl)phenyl)chromane-3-carboxamide (34 mg, 18%). The racemic product was separated by chiral chromatography using Chiral Separation Method C to yield Compound (2), which is characterized by retention time=6.04 min (second eluted from the column).

Analytical HPLC Method A. Rt: 1.73 min; MS: 355 (M+H). $[\alpha]_D^{25}$=+5.83 (589 nm, c=0.55, DMSO).

Compound (3): N-(3-chloro-4-(oxazol-5-yl)phenyl) isochromane-3-carboxamide

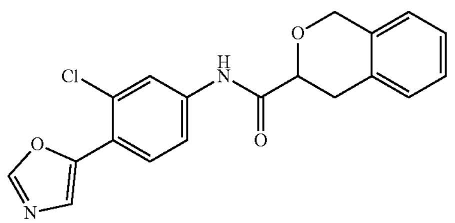

The title compound was prepared from isochromane-3-carboxylic acid and 3-chloro-4-(oxazol-5-yl)aniline using coupling procedure A and preparative HPLC Method A (yield 33%).

MS: 355.0 (M+H).

$^1$H NMR (400 MHz, DMSO-$d_6$) δ 10.25 (s, 1H), 8.53 (s, 1H), 8.11 (d, J=1.7 Hz, 1H), 7.84 (dd, J=8.7, 1.9 Hz, 1H), 7.79 (d, J=8.7 Hz, 1H), 7.72 (s, 1H), 7.25-7.18 (m, 3H), 7.16-7.09 (m, 1H), 5.04-4.85 (m, 2H), 4.48-4.37 (m, 1H), 3.19-2.95 (m, 2H).

Compound (4): N-(3-chloro-4-(oxazol-5-yl)phenyl) chromane-4-carboxamide

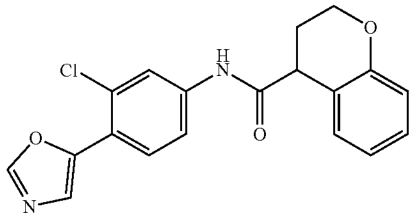

The title compound was prepared from 3,4-dihydro-2H-1-benzopyran-4-carboxylic acid and 3-chloro-4-(oxazol-5-yl) aniline using coupling procedure A and preparative HPLC Method A (yield 12%).

MS: 355.0 (M+H).

Compound (5): N-(3-chloro-4-(oxazol-5-yl)phenyl)-1,2,3,4-tetrahydronaphthalene-2-carboxamide

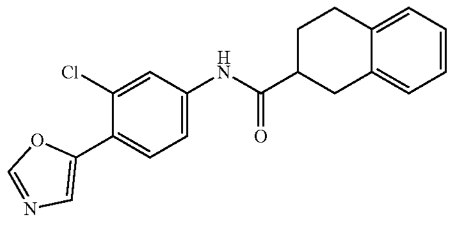 [SMILES: O=C(Nc1ccc(-c2cnco2)c(Cl)c1)C1CCc2ccccc2C1]

A mixture of 3-chloro-4-(oxazol-5-yl)aniline (110 mg, 0,567 mmol), 2,3-dihydro-1H-indene-1-carboxylic acid (105 mg, 0,595 mmol) and N-hydroxybenzotriazole (85 mg, 0,624 mmol) was dissolved in 1 ml of dry dimethyl acetamide and cooled to −10° C. Then 106 mg (0.68 mmol) of 1-ethyl-3-(3-dimethylaminopropyl)carbodiimide were added and the mixture was stirred for 16 h at room temperature. 30 ml of water were added, the obtained precipitate was filtered, washed three times with 10 ml of water, once with 3 ml of isopropanol and twice with 10 ml of hexane. Then it was dried on air at 50° C. 110 mg were obtained (yield 55%).

MS: 353.0 (M+H).

$^1$H NMR (400 MHz, DMSO-$d_6$) δ 10.37 (s, 1H), 8.52 (s, 1H), 8.04 (d, J=2.0 Hz, 1H), 7.78 (d, J=8.7 Hz, 1H), 7.70 (s, 1H), 7.65 (dd, J=8.7, 2.0 Hz, 1H), 7.18-7.00 (m, 4H), 2.94 (d, J=7.8 Hz, 2H), 2.89-2.72 (m, 3H), 2.18-2.01 (m, 1H), 1.87-1.69 (m, 1H).

Compound (6): N-(3-chloro-4-(oxazol-5-yl)phenyl)-2,3-dihydro-1H-indene-1-carboxamide

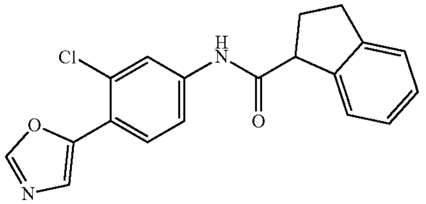 [SMILES: O=C(Nc1ccc(-c2cnco2)c(Cl)c1)C1CCc2ccccc21]

The title compound was prepared from 2,3-dihydro-1H-indene-1-carboxylic acid and 3-chloro-4-(oxazol-5-yl) aniline using coupling procedure A and preparative HPLC Method A (yield 9%).

MS: 339.0 (M+H).

Compound (7): N-(3-chloro-4-(oxazol-5-yl)phenyl)-2,3-dihydro-1H-indene-2-carboxamide

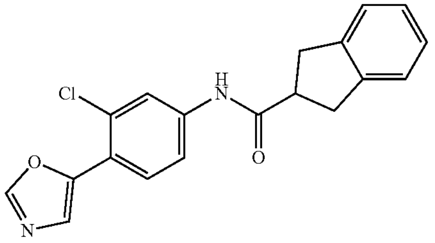 [SMILES: O=C(Nc1ccc(-c2cnco2)c(Cl)c1)C1Cc2ccccc2C1]

The title compound was prepared from 2,3-dihydro-1H-indene-2-carboxylic acid and 3-chloro-4-(oxazol-5-yl) aniline using coupling procedure A and preparative HPLC Method A (yield 14%).

MS: 339.2 (M+H).

Compound (8): N-(3-chloro-4-(oxazol-5-yl)phenyl)-6-methoxychromane-3-carboxamide

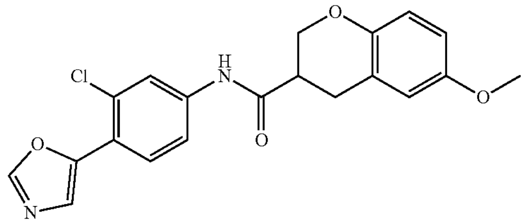 [SMILES: COc1ccc2c(c1)CC(C(=O)Nc1ccc(-c3cnco3)c(Cl)c1)CO2]

To a stirred solution of 3-chloro-4-(oxazol-5-yl)aniline (200 mg, 1.03 mmol) and 6-methoxy-3,4-dihydro-2H-1-benzopyran-3-carboxylic acid (278.76 mg, 1.34 mmol) in DMF (2 mL) were added DIPEA (0.52 mL) and HATU (784 mg, 2.06 mmol) at room temperature and the reaction was stirred for 16 h at room temperature. After completion of the reaction, the reaction mixture was purified by preparative HPLC to yield N-(3-chloro-4-(oxazol-5-yl)phenyl)-6-methoxychromane-3-carboxamide (143 mg, 36%).

Analytical HPLC Method A. Rt: 1.73 min; MS: 385.2 (M+H).

Compound (9): N-(3-fluoro-4-(oxazol-5-yl)phenyl) chromane-4-carboxamide

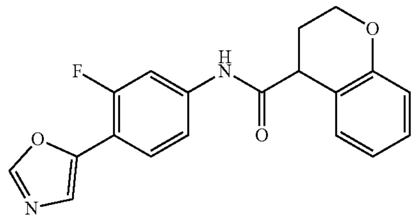 [SMILES: O=C(Nc1ccc(-c2cnco2)c(F)c1)C1CCOc2ccccc21]

To a stirred solution of 3-fluoro-4-(1,3-oxazol-5-yl)aniline (150 mg, 0.84 mmol) and 3,4-dihydro-2H-1-benzopyran-4-carboxylic acid (195.21 mg, 1.09 mmol) in DMF (2 mL) were added DIPEA (0.44 mL) and HATU (640 mg, 1.68 mmol) at room temperature and the reaction was stirred for 16 h at room temperature. After completion of the reaction, the reaction mixture was purified by preparative HPLC to yield N-(3-fluoro-4-(oxazol-5-yl)phenyl)chromane-4-carboxamide (102 mg, 35%).

Analytical HPLC Method A. Rt: 1.50 min; MS: 339.2 (M+H).

Compound (10): N-(3-fluoro-4-(oxazol-5-yl)phenyl) chromane-3-carboxamide

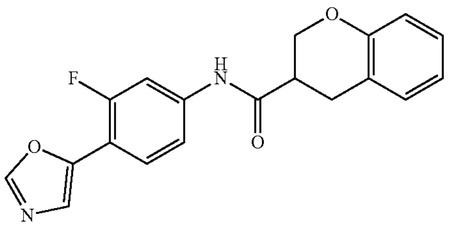 [SMILES: O=C(Nc1ccc(-c2cnco2)c(F)c1)C1COc2ccccc2C1]

To a stirred solution of 3-fluoro-4-(1,3-oxazol-5-yl)aniline (100 mg, 0.56 mmol) and 3,4-dihydro-2H-1-benzopyran-3-carboxylic acid (130.7 mg, 0.73 mmol) in DMF (1 mL) were added DIPEA (0.29 mL) and HATU (427 mg, 1.12 mmol) at room temperature and the reaction was stirred for 16 h at room temperature. After completion of the reaction, the reaction mixture was purified by preparative HPLC to yield N-(3-fluoro-4-(oxazol-5-yl)phenyl)chromane-3-carboxamide (70 mg, 36%).

Analytical HPLC Method A. Rt: 1.62 min; MS: 339.2 (M+H).

Compound (11): N-(3-fluoro-4-(oxazol-5-yl)phenyl)-6-methoxychromane-3-carboxamide

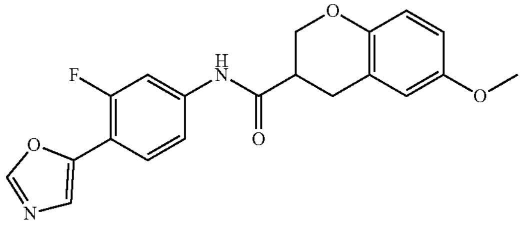 [SMILES: COc1ccc2c(c1)CC(C(=O)Nc1ccc(-c3cnco3)c(F)c1)CO2]

To a stirred solution of 3-fluoro-4-(1,3-oxazol-5-yl)aniline (150 mg, 0.84 mmol) and 6-methoxy-3,4-dihydro-2H-1-benzopyran-3-carboxylic acid (227.86 mg, 1.09 mmol) in DMF (1.5 mL) were added DIPEA (0.44 mL) and HATU (640.5 mg, 1.68 mmol) at room temperature and the reaction was stirred for 16 h at room temperature. After completion of the reaction, the reaction mixture was purified by preparative HPLC to yield N-(3-fluoro-4-(oxazol-5-yl)phenyl)-6-methoxychromane-3-carboxamide (121 mg, 38%).

Analytical HPLC Method A. Rt: 1.64 min; MS: 369.3 (M+H).

Compound (12): N-(3-methoxy-4-(oxazol-5-yl)phenyl)chromane-4-carboxamide

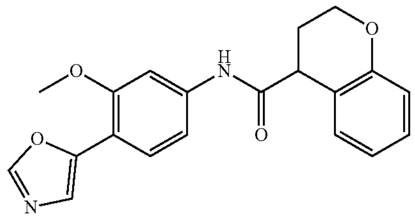 [SMILES: COc1cc(NC(=O)C2CCOc3ccccc32)ccc1-c1cnco1]

To a stirred solution of 3-methoxy-4-(oxazol-5-yl)aniline (75 mg, 0.395 mmol) and 3,4-dihydro-2H-1-benzopyran-4-carboxylic acid (105.3 mg, 0.592 mmol) in DMF (3 mL) were added DIPEA (0.15 mL) and HATU (226 mg, 0.592 mmol) at room temperature and the reaction was stirred for 12 h at room temperature. After completion of the reaction, the reaction mixture was purified by preparative HPLC to yield N-(3-methoxy-4-(oxazol-5-yl)phenyl) chromane-4-carboxamide (60.07 mg, 44%).

Analytical HPLC Method A. Rt: 1.42 min; MS: 351.2 (M+H).

Compound (13): N-(3-methoxy-4-(oxazol-5-yl)phenyl)chromane-3-carboxamide

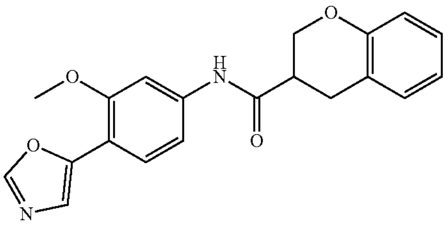 [SMILES: COc1cc(NC(=O)C2COc3ccccc3C2)ccc1-c1cnco1]

To a stirred solution of 3-methoxy-4-(oxazol-5-yl)aniline (75 mg, 0.395 mmol) and 3,4-dihydro-2H-1-benzopyran-3-carboxylic acid (105.3 mg, 0.592 mmol) in DMF (3 mL) were added DIPEA (0.15 mL) and HATU (226 mg, 0.592 mmol) at room temperature and the reaction was stirred for 12 h at room temperature. After completion of the reaction, the reaction mixture was purified by preparative HPLC to yield N-(3-methoxy-4-(oxazol-5-yl)phenyl) chromane-3-carboxamide (77.6 mg, 56%).

Analytical HPLC Method A. Rt: 1.59 min; MS: 351.2 (M+H).

Compound (14): 6-methoxy-N-(3-methoxy-4-(oxazol-5-yl)phenyl)chromane-3-carboxamide

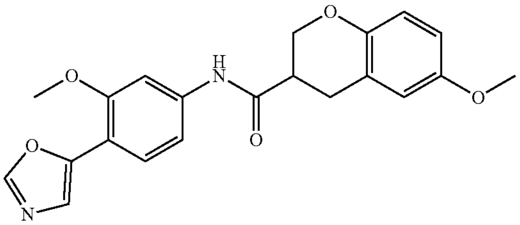 [SMILES: COc1ccc2c(c1)CC(C(=O)Nc1ccc(-c3cnco3)c(OC)c1)CO2]

To a stirred solution of 3-methoxy-4-(oxazol-5-yl)aniline (75 mg, 0.395 mmol) and 6-methoxy-3,4-dihydro-2H-1-benzopyran-3-carboxylic acid (123.1 mg, 0.592 mmol) in DMF (3 mL) were added DIPEA (0.15 mL) and HATU (226 mg, 0.592 mmol) at room temperature and the reaction was stirred for 12 h at room temperature. After completion of the reaction, the reaction mixture was purified by preparative HPLC to yield 6-methoxy-N-(3-methoxy-4-(oxazol-5-yl) phenyl)chromane-3-carboxamide (72.3 mg, 48%).

Analytical HPLC Method A. Rt: 1.55 min; MS: 381.2 (M+H).

Compound (15): first N-(3-methoxy-4-(oxazol-5-yl) phenyl)chromane-3-carboxamide

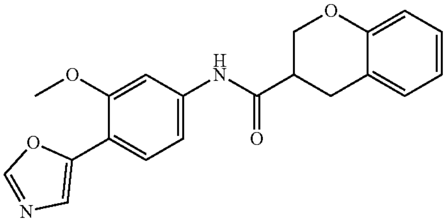 [SMILES: COc1cc(NC(=O)C2COc3ccccc3C2)ccc1-c1cnco1]

The racemic N-(3-methoxy-4-(oxazol-5-yl)phenyl) chromane-3-carboxamide (compound (13)) was subjected to chiral separation using Chiral Separation Method K. First N-(3-methoxy-4-(oxazol-5-yl)phenyl)chromane-3-carboxamide was identified using Chiral Separation Method G, Rt: 9.09 min.

MS: 351.25 (M+H).

Compound (16): second N-(3-methoxy-4-(oxazol-5-yl)phenyl)chromane-3-carboxamide

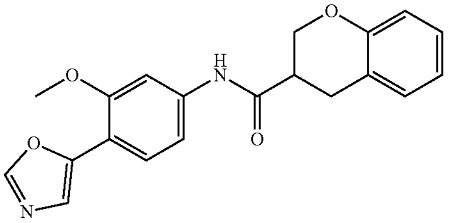 [SMILES: COc1cc(NC(=O)C2COc3ccccc3C2)ccc1-c1cnco1]

The racemic N-(3-methoxy-4-(oxazol-5-yl)phenyl) chromane-3-carboxamide (compound (13)) was subjected to chiral separation using Chiral Separation Method K. First N-(3-methoxy-4-(oxazol-5-yl)phenyl)chromane-3-carboxamide was identified using Chiral Separation Method G, Rt: 10.85 min.

MS: 351.25 (M+H).

Compound (17): N-(3-methyl-4-(oxazol-5-yl)phenyl)chromane-3-carboxamide

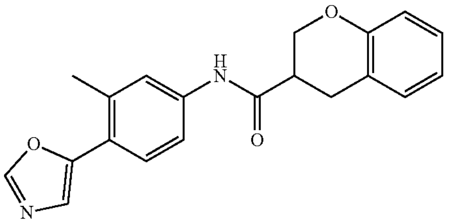 [SMILES: Cc1cc(NC(=O)C2COc3ccccc3C2)ccc1-c1cnco1]

A solution of chroman-3-carbonyl chloride prepared freshly in dry dichloromethane (10 mL) was added to the mixture of 3-methyl-4-(oxazol-5-yl)aniline (500 mg, 2.87 mmol) and triethylamine (1.25 mL, 8.61 mmol) in dry dichloromethane (10 mL) at 0° C. After the addition, reaction was slowly warmed to room temperature over 3 h. The reaction was monitored by TLC, after maximum conversion (part of the starting materials remained unreacted) diluted with dichloromethane (5 mL), washed with water (10 mL) and brine (15 mL), dried over $Na_2SO_4$, and concentrated under reduced pressure. The crude was purified by column chromatography followed by trituration with MTBE to obtain N-(3-methyl-4-(oxazol-5-yl)phenyl)chroman-3-carboxamide (240 mg, 25%).

Analytical HPLC Method B. Rt: 2.47 min, LCMS: 335.08 (M+H).

Compound (18): first N-(3-methyl-4-(oxazol-5-yl) phenyl)chromane-3-carboxamide

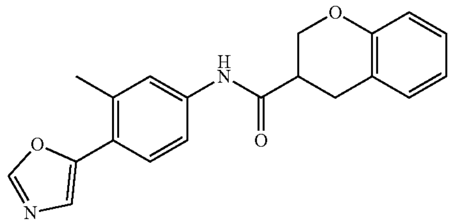 [SMILES: Cc1cc(NC(=O)C2COc3ccccc3C2)ccc1-c1cnco1]

Chiral separation of racemic N-(3-methyl-4-(oxazol-5-yl) phenyl)chromane-3-carboxamide (Compound (17)) using Chiral Separation Method A yields the title compound (65.6 mg) characterized by retention time=5.41. (First compound eluted from the column)

Compound (19): second N-(3-methyl-4-(oxazol-5-yl)phenyl)chromane-3-carboxamide

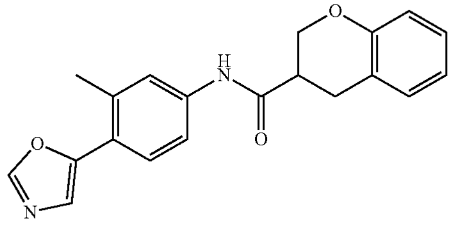 [SMILES: Cc1cc(NC(=O)C2COc3ccccc3C2)ccc1-c1cnco1]

Chiral separation of racemic N-(3-methyl-4-(oxazol-5-yl) phenyl)chromane-3-carboxamide (Compound (17)) using Chiral Separation Method A yields the title compound (75.6 mg) characterized by retention time=11.73 min. Second compound eluted from the column)

Compound (20): N-(2-methyl-4-(oxazol-5-yl)phenyl)chroman-3-carboxamide

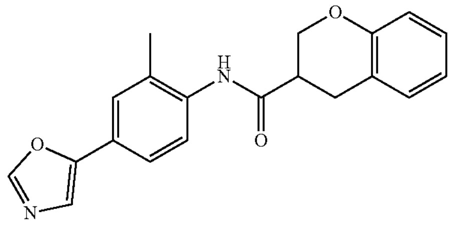 [SMILES: Cc1cc(-c2cnco2)ccc1NC(=O)C1COc2ccccc2C1]

A solution of chroman-3-carbonyl chloride prepared freshly in dry dichloromethane (10 mL) was added to the mixture of 3-methyl-4-(oxazol-5-yl)aniline (500 mg, 2.87 mmol) and triethylamine (1.25 mL, 8.61 mmol) in dry dichloromethane (10 mL) at 0° C. After the addition, reaction was slowly warmed to room temperature over 3 h. The reaction was monitored by TLC, after maximum conversion (part of the starting materials remained unreacted) diluted with dichloromethane (5 mL), washed with water (10 mL) and brine (15 mL), dried over $Na_2SO_4$, and concentrated under reduced pressure. The crude was purified by column chromatography followed by trituration with MTBE to give N-(2-methyl-4-(oxazol-5-yl) phenyl) chroman-3-carboxamide (210 mg, 22%).

Analytical HPLC Method B. Rt: 2.56 min, LCMS:335.1

Compound (21): first N-(2-methyl-4-(oxazol-5-yl) phenyl)chromane-3-carboxamide

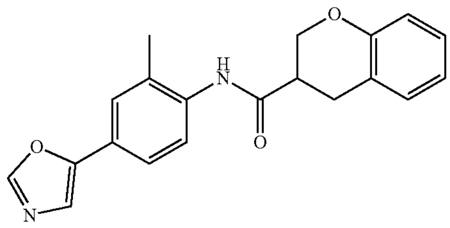 [SMILES: Cc1cc(-c2cnco2)ccc1NC(=O)C1COc2ccccc2C1]

Chiral separation of Compound (20) using Chiral Separation Method A yields (69.9 mg) characterized by retention time=5.41 min. (First eluted compound)

Compound (22): second N-(2-methyl-4-(oxazol-5-yl)phenyl)chromane-3-carboxamide

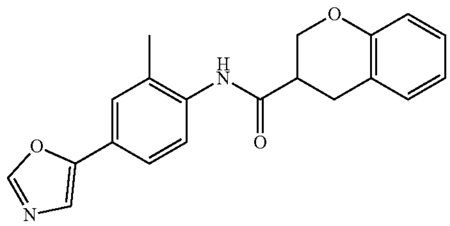 [SMILES: Cc1cc(-c2cnco2)ccc1NC(=O)C1COc2ccccc2C1]

Chiral separation of Compound (20) using Chiral Separation Method A yields (73.2 mg) characterized by retention time=11.73 min. (Second eluted compound)

Compound (23): N-(2-(difluoromethoxy)-4-(oxazol-5-yl)phenyl)chroman-3-carboxamide

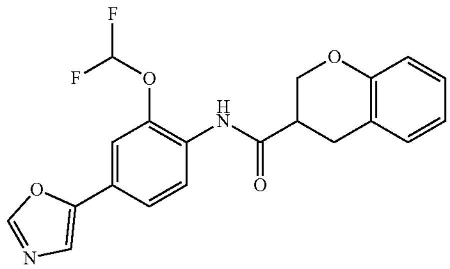 [SMILES: O=C(Nc1ccc(-c2cnco2)cc1OC(F)F)C1COc2ccccc2C1]

To a stirred solution of N-(4-bromo-2-(difluoromethoxy) phenyl)chroman-3-carboxamide (400 mg, 1.01 mmol) in 1,4-dioxane/water (20 mL, 2:1) 5-(4,4,5,5-tetramethyl-1,3,2-dioxaborolan-2-yl)oxazole (255 mg, 1.31 mmol) and $Na_2CO_3$ (213 mg, 2.02 mmol) were added under argon. The reaction mixture was degassed with argon for 20 min. Then $Pd(PPh_3)_4$ (58 mg, 0.05 mmol) was added and the mixture degassed with argon for 5 min. The reaction mixture was sealed and stirred at 80° C. for 10 h. After the maximum consumption of the starting material, the reaction mixture was cooled to room temperature, diluted with water (5.0 mL), and extracted with EtOAc (2×50 mL). Organic layers were combined, washed with water (10 mL) and brine (10 mL), dried over anhydrous $Na_2SO_4$, and evaporated under reduced pressure. The crude was purified column chromatography to give racemic N-(2-(difluoromethoxy)-4-(oxazol-5-yl)phenyl)chroman-3-carboxamide (152 mg, 39%).

Analytical HPLC Method B. Rt: 2.50 min, LCMS: 387 (M+H).

Compound (24): first N-(2-(difluoromethoxy)-4-(oxazol-5-yl)phenyl)chroman-3-carboxamide

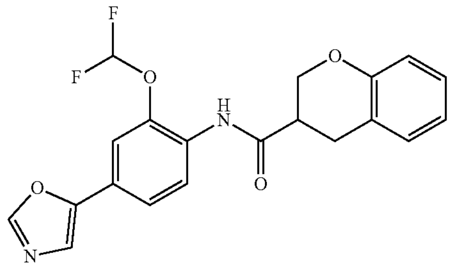 [SMILES: O=C(Nc1ccc(-c2cnco2)cc1OC(F)F)C1COc2ccccc2C1]

Chiral separation of racemic N-(2-(difluoromethoxy)-4-(oxazol-5-yl)phenyl)chroman-3-carboxamide Compound (23) using Chiral Separation Method C yields Compound (24) (44.9 mg) characterized by retention time=6.64 min. (First eluted compound)

Compound (25): second N-(2-(difluoromethoxy)-4-(oxazol-5-yl)phenyl)chroman-3-carboxamide

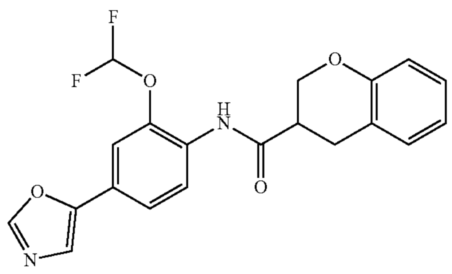 [SMILES: O=C(Nc1ccc(-c2cnco2)cc1OC(F)F)C1COc2ccccc2C1]

Chiral separation of racemic N-(2-(difluoromethoxy)-4-(oxazol-5-yl)phenyl)chroman-3-carboxamide Compound (23) using Chiral Separation Method C yields Compound (25) (47.0 mg) characterized by retention time=8.67 min. (Second eluted compound)

Compound (26): first N-(3-chloro-4-(oxazol-5-yl)phenyl)-6-fluorochromane-3-carboxamide

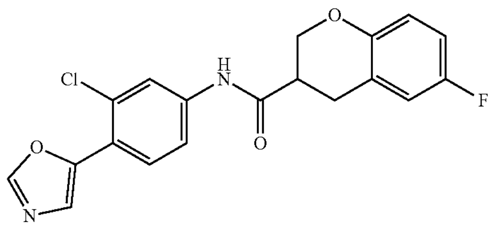 [SMILES: O=C(Nc1ccc(-c2cnco2)c(Cl)c1)C1COc2ccc(F)cc2C1]

The racemic compound was prepared from 6-fluorochromane-3-carboxylic acid and 3-chloro-4-(oxazol-5-yl)aniline using coupling procedure A and preparative HPLC Method A.

MS: 373.0 (M+H).

Chiral separation of racemic N-(3-chloro-4-(oxazol-5-yl)phenyl)-6-fluorochromane-3-carboxamide compound was accomplished using Chiral Separation Method H to yield Compound (26) characterized by retention time=10.9 min. (First eluted compound)

Compound (27): second N-(3-chloro-4-(oxazol-5-yl)phenyl)-6-fluorochromane-3-carboxamide

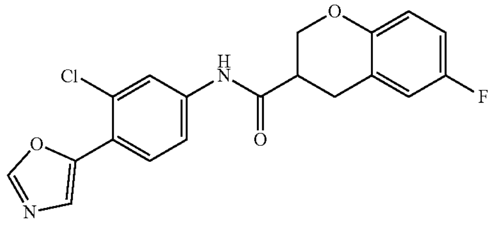 [SMILES: O=C(Nc1ccc(-c2cnco2)c(Cl)c1)C1COc2ccc(F)cc2C1]

Chiral separation of racemic N-(3-chloro-4-(oxazol-5-yl)phenyl)-6-fluorochromane-3-carboxamide compound was accomplished using Chiral Separation Method H to yield compound 26 characterized by retention time=18.9 min. (Second eluted compound)

Compound (28): racemic N-(3-chloro-4-(oxazol-5-yl)phenyl)-7-fluorochromane-3-carboxamide

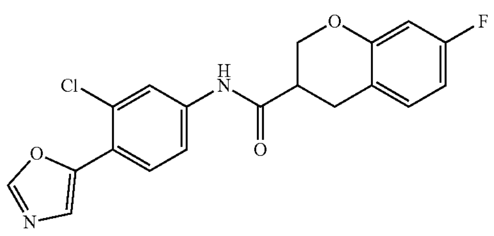 [SMILES: O=C(Nc1ccc(-c2cnco2)c(Cl)c1)C1COc2cc(F)ccc2C1]

The racemic compound was prepared from 7-fluorochromane-3-carboxylic acid (1.1 mmol) and 3-chloro-4-(oxazol-5-yl)aniline using coupling procedure A. The racemic product was purified by preparative HPLC method A (511 mg, 71% yield).

MS: 373.0 (M+H).

Compound (29): first N-(3-chloro-4-(oxazol-5-yl) phenyl)-7-fluorochromane-3-carboxamide

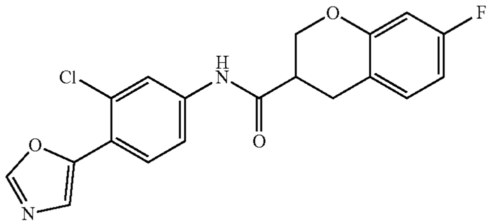 [SMILES: O=C(Nc1ccc(-c2cnco2)c(Cl)c1)C1COc2cc(F)ccc2C1]

Chiral separation of racemic N-(3-chloro-4-(oxazol-5-yl) phenyl)-7-fluorochromane-3-carboxamide compound was accomplished using Chiral Separation Method I to yield compound 26 (100.3 mg) characterized by retention time=11.5 min. (First eluted compound)

Compound (30): second N-(3-chloro-4-(oxazol-5-yl)phenyl)-7-fluorochromane-3-carboxamide

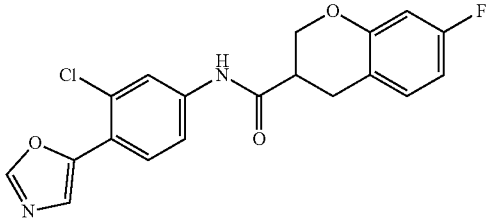 [SMILES: O=C(Nc1ccc(-c2cnco2)c(Cl)c1)C1COc2cc(F)ccc2C1]

Chiral separation of racemic N-(3-chloro-4-(oxazol-5-yl) phenyl)-7-fluorochromane-3-carboxamide compound was accomplished using Chiral Separation Method I to yield compound 26 (87.1 mg) characterized by retention time=15.8 min. (Second eluted compound)

Compound (31): 6-chloro-N-(3-chloro-4-(oxazol-5-yl)phenyl)chromane-3-carboxamide

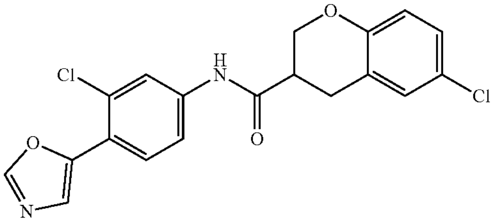 [SMILES: O=C(Nc1ccc(-c2cnco2)c(Cl)c1)C1COc2ccc(Cl)cc2C1]

The title compound was prepared from 6-chlorochromane-3-carboxylic acid and 3-chloro-4-(oxazol-5-yl)aniline using coupling procedure A and preparative HPLC Method A (yield 16%).

MS: 389.0 (M+H).

Compound (32): N-(3-chloro-4-(oxazol-5-yl)phenyl)-6,8-difluorochromane-3-carboxamide

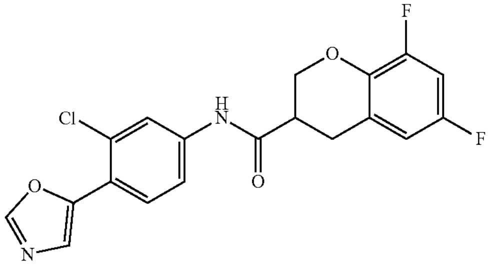 [SMILES: O=C(Nc1ccc(-c2cnco2)c(Cl)c1)C1COc2c(F)cc(F)cc2C1]

The title compound was prepared from 6,8-difluorochromane-3-carboxylic acid and 3-chloro-4-(oxazol-5-yl)aniline using coupling procedure A and preparative HPLC Method A (yield 18%).

MS: 391.0 (M+H).

$^1$H NMR (500 MHz, DMSO-$d_6$) δ 10.58 (s, 1H), 8.52 (s, 1H), 8.01-7.97 (m, 1H), 7.79 (d, J=8.6 Hz, 1H), 7.71 (s, 1H), 7.61 (dd, J=8.5, 1.6 Hz, 1H), 7.14-7.06 (m, 1H), 6.93 (d, J=8.4 Hz, 1H), 4.54-4.48 (m, 1H), 4.16-4.08 (m, 1H), 3.13-3.08 (m, 1H), 3.08-3.00 (m, 2H).

Compound (33): N-(3-chloro-4-(oxazol-5-yl)phenyl)-5-methoxychromane-3-carboxamide

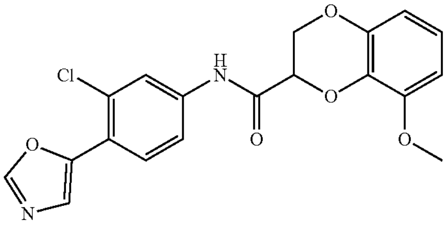 [SMILES: COc1cccc2c1OC(C(=O)Nc1ccc(-c3cnco3)c(Cl)c1)CO2]

The title compound was prepared from 5-methoxychromane-3-carboxylic acid and 3-chloro-4-(oxazol-5-yl)aniline using coupling procedure A and preparative HPLC Method A. (Yield: 16.6%)

MS: 385.0 (M+H)

Compound (34): N-(2-(2-(dimethylamino) ethoxy)-4-(oxazol-5-yl)phenyl)chroman-3-carboxamide

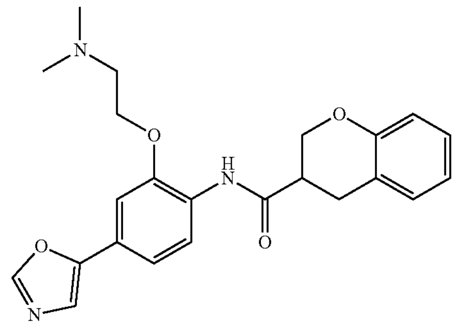 [SMILES: CN(C)CCOc1cc(-c2cnco2)ccc1NC(=O)C1COc2ccccc2C1]

A solution of chroman-3-carbonyl chloride in dry dichloromethane (10 mL) was added to the mixture of 2-(2-(dimethylamino)ethoxy)-4-(oxazol-5-yl)aniline (535 mg, 2.16 mmol) and triethylamine (0.9 mL, 6.50 mmol) in dry dichloromethane (10 mL) at 0° C. After the addition, reaction was slowly warmed to room temperature over 3 h. The reaction was monitored by TLC. After maximum conversion (part of the starting materials remained unreacted) the reaction mixture was diluted with dichloromethane (10 mL), washed with water (30 mL) and brine (20 mL), dried over $Na_2SO_4$, and concentrated under reduced pressure. The crude mixture was purified by column chromatography to give racemic N-(2-(2-(dimethylamino)ethoxy)-4-(oxazol-5-yl)phenyl)chroman-3-carboxamide (410 mg, 45%) as a solid.

Analytical HPLC Method C. Rt: 2.03 min; MS: 408.2 (M+H).

Compound (35): first N-(2-(2-(dimethylamino) ethoxy)-4-(oxazol-5-yl)phenyl)chroman-3-carboxamide

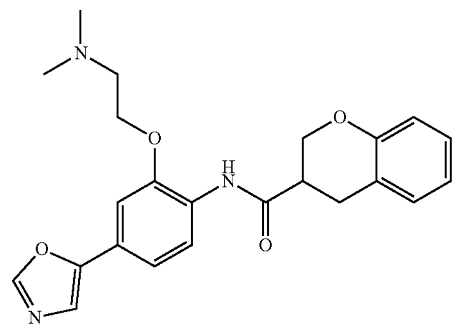 [SMILES: CN(C)CCOc1cc(-c2cnco2)ccc1NC(=O)C1COc2ccccc2C1]

The racemic N-(2-(2-(dimethylamino)ethoxy)-4-(oxazol-5-yl)phenyl)chroman-3-carboxamide (Compound (34)) was subjected to chiral separation using Chiral Separation Method D. First N-(2-(2-(dimethylamino) ethoxy)-4-(oxazol-5-yl)phenyl)chroman-3-carboxamide was eluted first at 4.16 min (83.8 mg).

Analytical HPLC Method C. Rt: 2.03 min; MS: 408.2 (M+H).

Compound (36): second N-(2-(2-(dimethylamino) ethoxy)-4-(oxazol-5-yl)phenyl)chroman-3-carboxamide

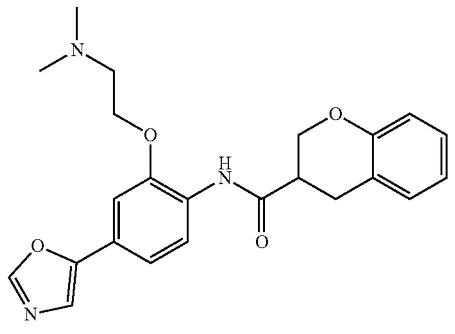 [SMILES: CN(C)CCOc1cc(-c2cnco2)ccc1NC(=O)C1COc2ccccc2C1]

The racemic N-(2-(2-(dimethylamino)ethoxy)-4-(oxazol-5-yl)phenyl)chroman-3-carboxamide (Compound (34)) was subjected to chiral separation using Chiral Separation Method D. Second N-(2-(2-(dimethylamino) ethoxy)-4-(oxazol-5-yl)phenyl)chroman-3-carboxamide was eluted first at 7.89 min (56.3 mg).

Analytical HPLC Method C. Rt: 2.03 min; MS: 408.2 (M+H).

Compound (37): racemic N-(4-(oxazol-5-yl)-3-(trifluoromethyl)phenyl)chromane-3-carboxamide

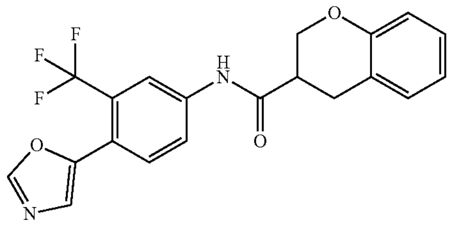 [SMILES: O=C(Nc1ccc(-c2cnco2)c(C(F)(F)F)c1)C1COc2ccccc2C1]

A solution of chroman-3-carbonyl chloride (in dry dichloromethane (10 mL) was added to the mixture of 4-(oxazol-5-yl)-3-(trifluoromethyl)aniline (600 mg, 2.63 mmol) and triethylamine (1.1 mL, 7.90 mmol) in dry dichloromethane (10 mL) at 0° C. After the addition, reaction was slowly warmed to room temperature over 3 h.

The reaction was monitored by TLC, after maximum conversion (part of the starting materials remained unreacted) diluted with dichloromethane (5 mL), washed with water (20 mL) and brine (15 mL), dried over $Na_2SO_4$, and concentrated under reduced pressure. The crude was purified by column chromatography using silica gel to give racemic N-(4-(oxazol-5-yl)-3-(trifluoromethyl)phenyl)chroman-3-carboxamide (350 mg, 35%) as solid.

Analytical HPLC Method C. Rt: 2.79 min; MS: 389.1 (M+H).

Compound (38): first N-(4-(oxazol-5-yl)-3-(trifluoromethyl)phenyl)chromane-3-carboxamide

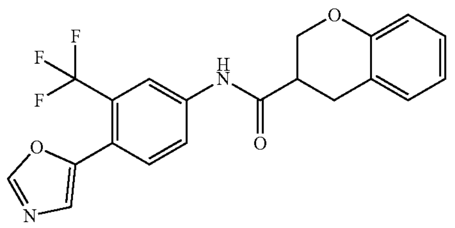 [SMILES: O=C(Nc1ccc(-c2cnco2)c(C(F)(F)F)c1)C1COc2ccccc2C1]

The racemic N-(4-(oxazol-5-yl)-3-(trifluoromethyl)phenyl)chroman-3-carboxamide was subjected to chiral separation using Chiral Separation Method E. First N-(2-(2-(dimethylamino)ethoxy)-4-(oxazol-5-yl)phenyl)chroman-3-carboxamide was eluted at 2.69 min (70.2 mg).

Analytical HPLC Method C. Rt: 2.79 min; MS: 389.1 (M+H).

Compound (39): second N-(4-(oxazol-5-yl)-3-(trifluoromethyl)phenyl)chromane-3-carboxamide

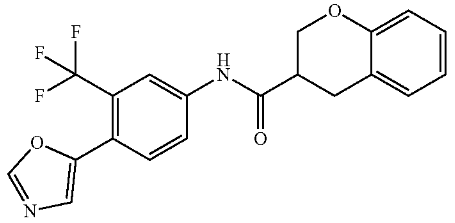 [SMILES: O=C(Nc1ccc(-c2cnco2)c(C(F)(F)F)c1)C1COc2ccccc2C1]

The racemic N-(4-(oxazol-5-yl)-3-(trifluoromethyl)phenyl)chroman-3-carboxamide was subjected to chiral separation using Chiral Separation Method E. Second N-(2-(2-(dimethylamino)ethoxy)-4-(oxazol-5-yl)phenyl)chroman-3-carboxamide was eluted at 3.24 min (71.6 mg).

Analytical HPLC Method C. Rt: 2.79 min; MS: 389.1 (M+H).

Compound (40): second N-(3-chloro-5-fluoro-4-(oxazol-5-yl)phenyl)chroman-3-carboxamide

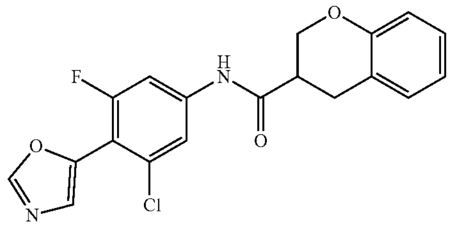 [SMILES: O=C(Nc1cc(F)c(-c2cnco2)c(Cl)c1)C1COc2ccccc2C1]

To a stirred solution of N-(4-bromo-3-chloro-2-fluorophenyl)chroman-3-carboxamide (100 mg, 0.260 mmol) in 1,4-dioxane/water (6 mL, 2:1) 5-(4,4,5,5-tetramethyl-1,3,2-dioxaborolan-2-yl)oxazole (66 mg, 0.338 mmol), and $Na_2CO_3$ (55 mg, 0.521 mmol) were added under argon. The reaction mixture was degassed with argon for 20 min. Then $Pd(dppf)Cl_2$— dichloromethane complex (10.6 mg, 0.013 mmol) was added and degassed with argon for 5 min. The reaction mixture was sealed and stirred at 80° C. for 8.0 h. The reaction mixture was cooled to room temperature, diluted with water (5.0 mL), and extracted with EtOAc (2×30 mL). Organic layers were combined, washed with water and brine, dried over anhydrous $Na_2SO_4$, and evaporated under reduced pressure. The crude was purified by column chromatography to give racemic N-(3-chloro-5-fluoro-4-(oxazol-5-yl)phenyl)chroman-3-carboxamide (20 mg, 20%) as solid. The racemic N-(3-chloro-5-fluoro-4-(oxazol-5-yl)phenyl)chroman-3-carboxamide was subjected to chiral separation using Chiral Separation Method F. Second N-(3-chloro-5-fluoro-4-(oxazol-5-yl)phenyl)chroman-3-carboxamide was eluted second at 5.25 min (21.6 mg).

Analytical HPLC Method C. Rt: 2.78 min; MS: 373.1 (M+H).

Compound (41): first N-(3-chloro-5-fluoro-4-(oxazol-5-yl)phenyl)chroman-3-carboxamide

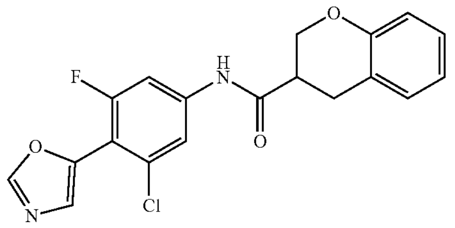 [SMILES: O=C(Nc1cc(F)c(-c2cnco2)c(Cl)c1)C1COc2ccccc2C1]

To a stirred solution of N-(4-bromo-3-chloro-2-fluorophenyl)chroman-3-carboxamide (100 mg, 0.260 mmol) in 1,4-dioxane/water (6 mL, 2:1) 5-(4,4,5,5-tetramethyl-1,3,2-dioxaborolan-2-yl)oxazole (66 mg, 0.338 mmol), and $Na_2CO_3$ (55 mg, 0.521 mmol) were added under argon. The reaction mixture was degassed with argon for 20 min. Then $Pd(dppf)Cl_2$— dichloromethane complex (10.6 mg, 0.013 mmol) was added and degassed with argon for 5 min. The reaction mixture was sealed and stirred at 80° C. for 8.0 h. The reaction mixture was cooled to room temperature, diluted with water (5.0 mL), and extracted with EtOAc (2×30 mL). Organic layers were combined, washed with water and brine, dried over anhydrous $Na_2SO_4$, and evaporated under reduced pressure. The crude was purified by column chromatography to give racemic N-(3-chloro-5-fluoro-4-(oxazol-5-yl)phenyl)chroman-3-carboxamide (20 mg, 20%) as solid. The racemic N-(3-chloro-5-fluoro-4-(oxazol-5-yl)phenyl)chroman-3-carboxamide was subjected to chiral separation using Chiral Separation Method F. First N-(3-chloro-5-fluoro-4-(oxazol-5-yl)phenyl)chroman-3-carboxamide was eluted first at 4.78 min (21.9 mg).

Analytical HPLC Method C. Rt: 2.78 min; MS: 373.1 (M+H).

Compound (42): N-(3-chloro-2-fluoro-4-(oxazol-5-yl)phenyl)chromane-3-carboxamide

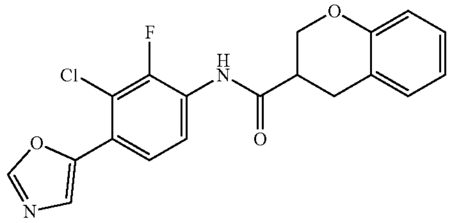 [SMILES: O=C(Nc1ccc(-c2cnco2)c(Cl)c1F)C1COc2ccccc2C1]

To a stirred solution of N-(4-bromo-3-chloro-2-fluorophenyl)chroman-3-carboxamide (100 mg, 0.260 mmol) in 1,4-dioxane/water (6 mL, 2:1) 5-(4,4,5,5-tetramethyl-1,3,2-dioxaborolan-2-yl)oxazole (66 mg, 0.338 mmol), and $Na_2CO_3$ (55 mg, 0.521 mmol) were added under argon. The reaction mixture was degassed with argon for 20 min. Then $Pd(dppf)Cl_2$— dichloromethane complex (10.63 mg, 0.013 mmol) was added and degassed with argon for 5 min. The reaction mixture was sealed and stirred at 80° C. for 8 h. The reaction mixture was cooled to room temperature, diluted with water (5.0 mL), and extracted with ethyl acetate (2×30 mL). Organic layers were combined washed with water (10 mL) and brine (10 mL), dried over anhydrous sodium sulphate, and evaporated under reduced pressure. The crude was purified by column chromatography to yield N-(3-chloro-2-fluoro-4-(oxazol-5-yl) phenyl) chroman-3-carboxamide (Compound 42) (19 mg, 19%) as solid.

Analytical HPLC Method C. Rt: 2.75 min; MS: 373.1 (M+H).

The invention claimed is:

1. A method of treating and/or preventing a disease involving the retinal pigment epithelium, comprising administering the compound of the formula (I)

(I)

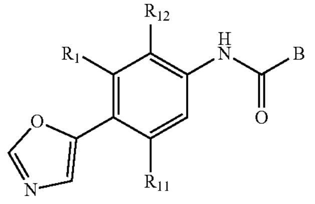

or a pharmaceutically acceptable salt, a racemic mixture, a corresponding enantiomer or, if applicable, a corresponding diastereomer thereof, wherein:

$R_1$, $R_{11}$ and $R_{12}$ are independently selected from the group consisting of hydrogen, fluoro, chloro, methoxy, trifluoromethyl, methyl and difluoromethoxy, whereby at least one of $R_1$, $R_{11}$ and $R_{12}$ is not hydrogen B is selected from the group consisting of a residue of formula (II), (III), (IV), (V), (VI) and (VII)

(II)

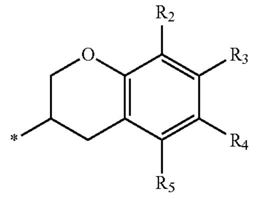

(III)

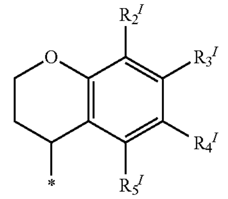

(IV)

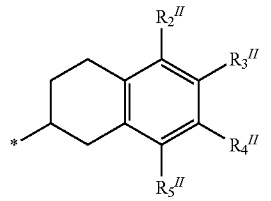

(V)

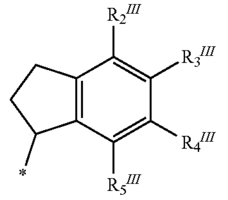

-continued (VI)

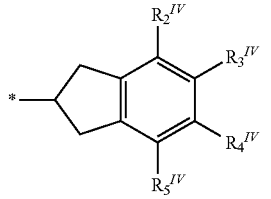

(VII)

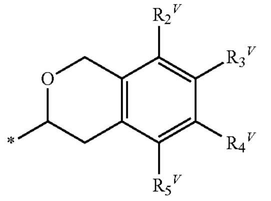

wherein,

"*" denotes the point of attachment to the remainder of the molecule, and $R_2$, $R_3$, $R_4$, $R_5$, $R_2^I$, $R_3^I$, $R_4^I$, $R_5^I$, $R_2^{II}$, $R_3^{II}$, $R_4^{II}$, $R_5^{II}$, $R_2^{III}$, $R_3^{III}$, $R_4^{III}$, $R_5^{III}$, $R_2^{IV}$, $R_3^{IV}$, $R_4^{IV}$, $R_5^{IV}$, $R_2^V$, $R_3^V$, $R_4^V$, $R_5^V$ are independently selected from the group consisting of hydrogen, a linear or branched alkyl having 1 to 3 carbon atoms, fluoro, chloro, bromo, methoxy, ethoxy, propoxy, trifluoromethyl and difluoromethoxy.

2. The method according to claim 1, wherein the compound of formula (I) the asymmetric center at ring position * of the residue of formula (II), (III), (IV), (V), (VI), (VII), (VIII) or (IX) has the configuration depicted in the compound of formula (Ii)

(Ii)

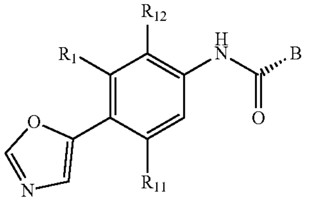

and B, $R_1$, $R_{11}$, $R_{12}$, $R_2$, $R_3$, $R_4$, $R_5$, $R_2^I$, $R_3^I$, $R_4^I$, $R_5^I$, $R_2^{II}$, $R_3^{II}$, $R_4^{II}$, $R_5^{II}$, $R_2^{III}$, $R_3^{III}$, $R_4^{III}$, $R_5^{III}$, $R_2^{IV}$, $R_3^{IV}$, $R_4^{IV}$, $R_5^{IV}$, $R_2^V$, $R_3^V$, $R_4^V$, $R_5^V$ have the same definition as above.

3. The method according to claim 1, wherein the compound of formula (I) asymmetric center at ring position * of the residue of formula (II), (III), (IV), (V), (VI), (VII), (VIII) or (IX) has the configuration depicted in the compound of formula (Iii)

(Iii)

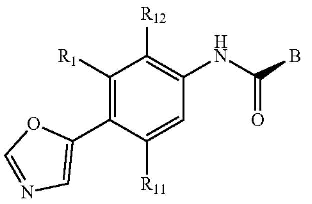

and B, $R_1$, $R_{11}$, $R_{12}$, $R_2$, $R_3$, $R_4$, $R_5$, $R_2^I$, $R_3^I$, $R_4^I$, $R_5^I$, $R_2^{II}$, $R_3^{II}$, $R_4^{II}$, $R_5^{II}$, $R_2^{III}$, $R_3^{III}$, $R_4^{III}$, $R_5^{III}$, $R_2^{IV}$, $R_3^{IV}$, $R_4^{IV}$, $R_5^{IV}$, $R_2^V$, $R_3^V$, $R_4^V$, $R_5^V$ have the same definition as above.

4. The method according to claim 1, wherein residue B is unsubstituted or monosubstituted.

5. The method according to claim 1, wherein the compound of formula (I) $R_3$, $R_4$, $R_3^I$, $R_4^I$, $R_3^{II}$, $R_4^{II}$, $R_3^{III}$, $R_4^{III}$, $R_3^{IV}$, $R_4^{IV}$, $R_3^V$, $R_4^V$ are independently selected from the group consisting of hydrogen, chloro, fluoro, methoxy and ethoxy.

6. The method according to claim 5, wherein the compound of formula (I) $R_3$, $R_3^I$, $R_3^{II}$, $R_3^{III}$, $R_3^{IV}$, or $R_3^V$ is selected from the group consisting of fluoro and chloro, and $R_2$, $R_4$, $R_5$, $R_2^I$, $R_4^I$, $R_5^I$, $R_2^{II}R_4^{II}$, $R_5^{II}$, $R_2^{III}$, $R_4^{III}$, $R_5^{III}$, $R_2^{IV}$, $R_4^{IV}$, $R_5^{IV}$, $R_2^V$, $R_4^V$, $R_5^V$ are all hydrogen.

7. The method according to claim 5, wherein the compound of formula (I), $R_4$, $R_4^I$, $R_4^{II}$r, $R_4^{III}$, $R_4^{IV}$, or $R_4^V$ is selected from the group consisting of methoxy and ethoxy, and $R_2$, $R_3$, $R_5$, $R_2^I$, $R_3^I$, $R_5^I$, $R_2^{II}$, $R_3^{II}$, $R_5^{II}$, $R_2^{III}$, $R_3^{III}$, $R_5^{III}$, $R_2^{IV}$, $R_3^{IV}$, $R_5^{IV}$, $R_2^V$, $R_3^V$, $R_5^V$ are all hydrogen.

8. The method according to claim 1, wherein the compound of formula (I) is selected from the group consisting of compounds 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46 and 47:

1

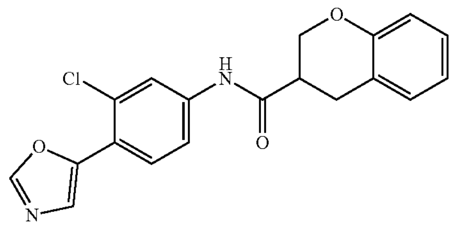

enantiomer with the shorter retention time from the chiral HPLC resolution

2

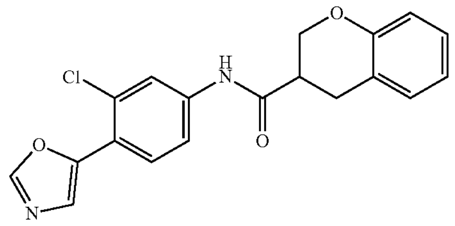 [SMILES: O=C(Nc1ccc(-c2cnco2)c(Cl)c1)C1COc2ccccc2C1]

enantiomer with the longer retention time from the chiral HPLC resolution

3

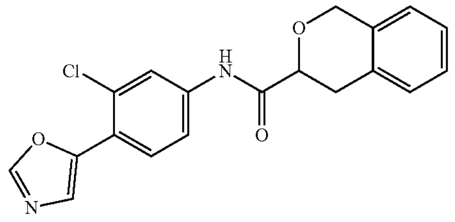 [SMILES: O=C(Nc1ccc(-c2cnco2)c(Cl)c1)C1Cc2ccccc2CO1]

(racemate)

-continued

4

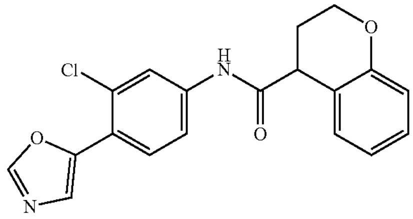

(racemate)

5

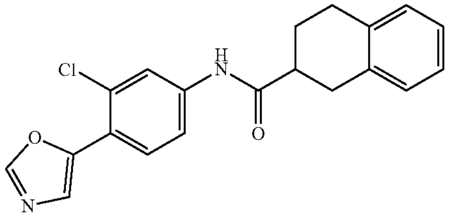 [SMILES: O=C(Nc1ccc(-c2cnco2)c(Cl)c1)C1CCc2ccccc2C1]

(racemate)

6

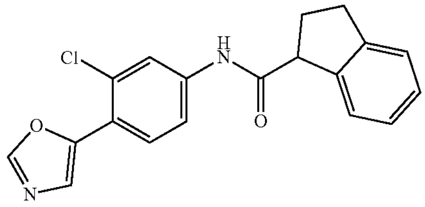 [SMILES: O=C(Nc1ccc(-c2cnco2)c(Cl)c1)C1CCc2ccccc21]

(racemate)

7

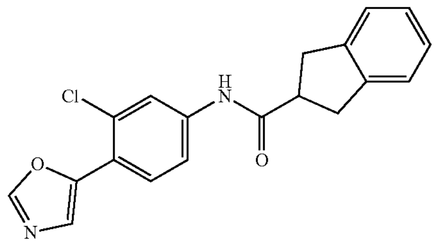 [SMILES: O=C(Nc1ccc(-c2cnco2)c(Cl)c1)C1Cc2ccccc2C1]

8

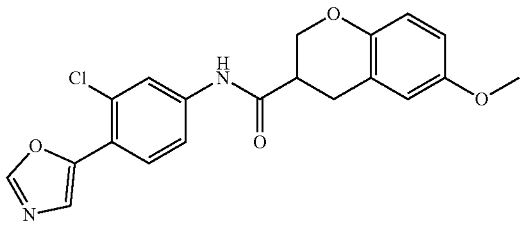 [SMILES: COc1ccc2c(c1)CC(C(=O)Nc1ccc(-c3cnco3)c(Cl)c1)CO2]

(racemate)

9

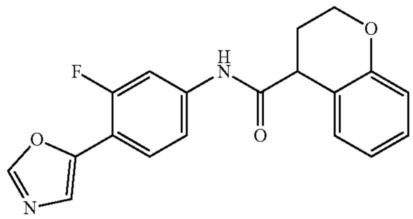

(racemate)

-continued

10

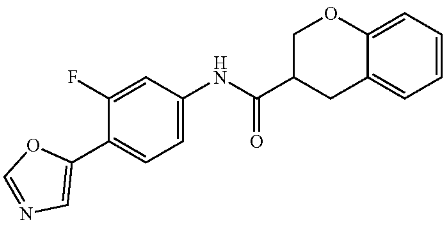 [SMILES: O=C(Nc1ccc(-c2cnco2)c(F)c1)C1COc2ccccc2C1]

(racemate)

11

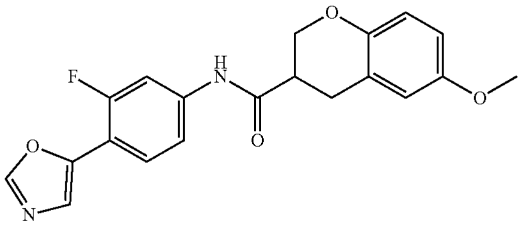 [SMILES: COc1ccc2c(c1)CC(C(=O)Nc1ccc(-c3cnco3)c(F)c1)CO2]

(racemate)

12

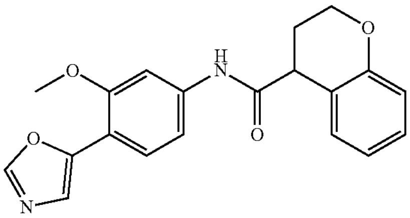 [SMILES: COc1cc(NC(=O)C2CCOc3ccccc32)ccc1-c1cnco1]

(racemate)

13

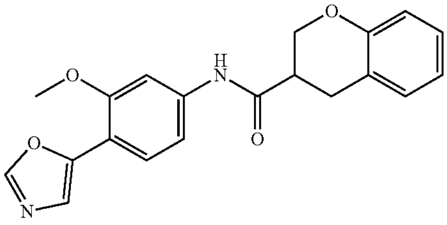 [SMILES: COc1cc(NC(=O)C2COc3ccccc3C2)ccc1-c1cnco1]

(racemate)

14

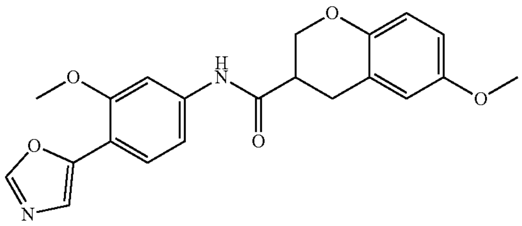 [SMILES: COc1ccc2c(c1)CC(C(=O)Nc1ccc(-c3cnco3)c(OC)c1)CO2]

(racemate)

-continued

15

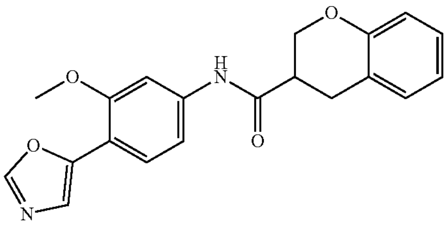

enantiomer with the shorter retention time from the chiral HPLC resolution

16

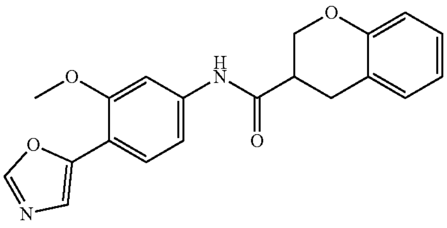 [SMILES: COc1cc(NC(=O)C2COc3ccccc3C2)ccc1-c1cnco1]

enantiomer with the longer retention time from the chiral HPLC resolution

17

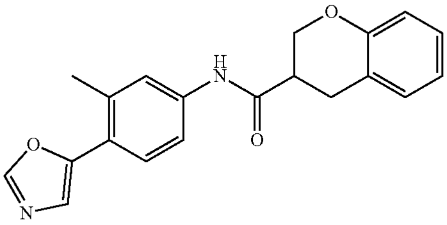 [SMILES: Cc1cc(NC(=O)C2COc3ccccc3C2)ccc1-c1cnco1]

(racemate)

18

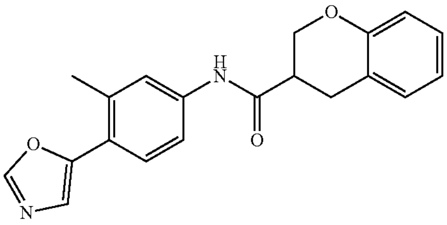 [SMILES: Cc1cc(NC(=O)C2COc3ccccc3C2)ccc1-c1cnco1]

enantiomer with the shorter retention time from the chiral HPLC resolution

19

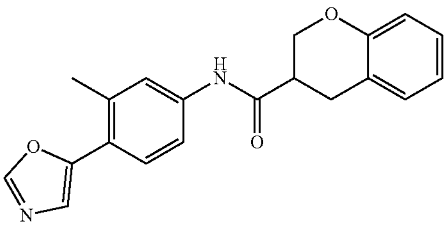 [SMILES: Cc1cc(NC(=O)C2COc3ccccc3C2)ccc1-c1cnco1]

enantiomer with the longer retention time from the chiral HPLC resolution

-continued

20

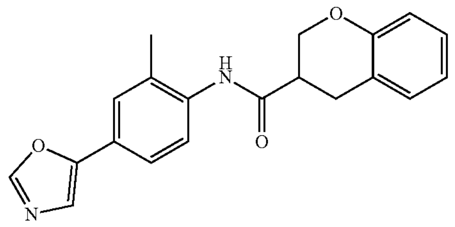 [SMILES: Cc1cc(-c2cnco2)ccc1NC(=O)C1COc2ccccc2C1]

(racemate)

21

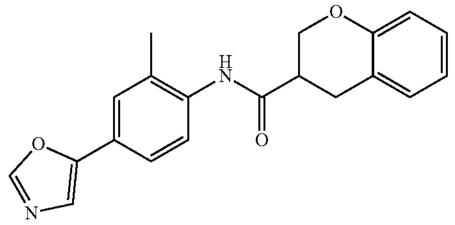 [SMILES: Cc1cc(-c2cnco2)ccc1NC(=O)C1COc2ccccc2C1]

enantiomer with the shorter retention time from the chiral HPLC resolution

22

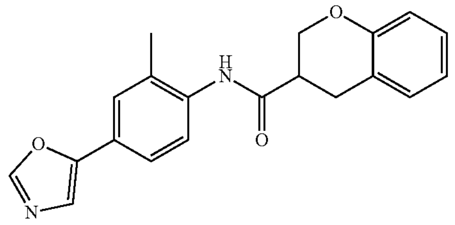 [SMILES: Cc1cc(-c2cnco2)ccc1NC(=O)C1COc2ccccc2C1]

enantiomer with the longer retention time from the chiral HPLC resolution

23

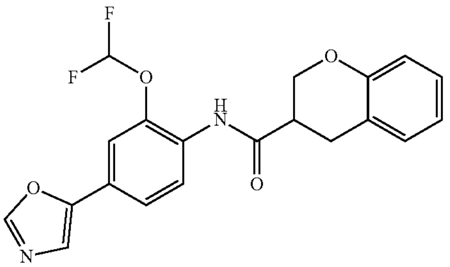 [SMILES: O=C(Nc1ccc(-c2cnco2)cc1OC(F)F)C1COc2ccccc2C1]

(racemate)

24

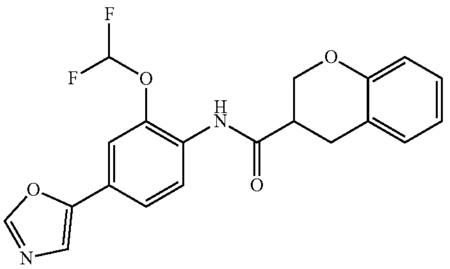 [SMILES: O=C(Nc1ccc(-c2cnco2)cc1OC(F)F)C1COc2ccccc2C1]

enantiomer with the shorter retention time from the chiral HPLC resolution

-continued

25

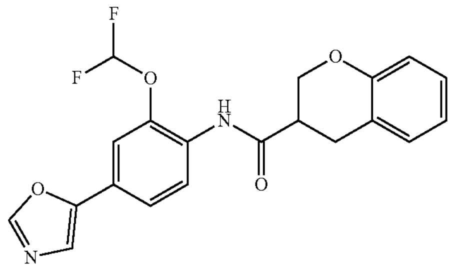 [SMILES: O=C(Nc1ccc(-c2cnco2)cc1OC(F)F)C1COc2ccccc2C1]

enantiomer with the longer retention time from the chiral HPLC resolution

26

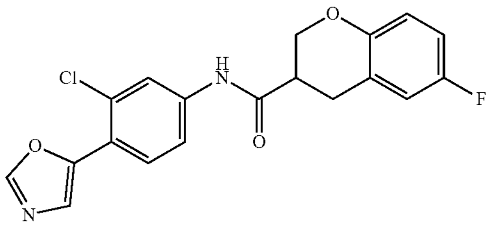 [SMILES: O=C(Nc1ccc(-c2cnco2)c(Cl)c1)C1COc2ccc(F)cc2C1]

enantiomer with the shorter retention time from the chiral HPLC resolution

27

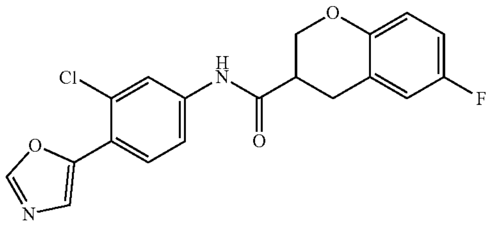 [SMILES: O=C(Nc1ccc(-c2cnco2)c(Cl)c1)C1COc2ccc(F)cc2C1]

enantiomer with the longer retention time from the chiral HPLC resolution

28

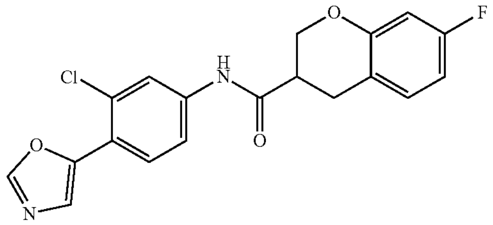 [SMILES: O=C(Nc1ccc(-c2cnco2)c(Cl)c1)C1COc2cc(F)ccc2C1]

(racemate)

29

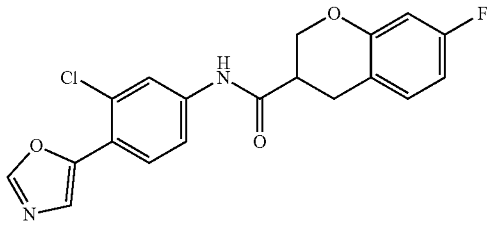 [SMILES: O=C(Nc1ccc(-c2cnco2)c(Cl)c1)C1COc2cc(F)ccc2C1]

enantiomer with the shorter retention time from the chiral HPLC resolution

-continued

30

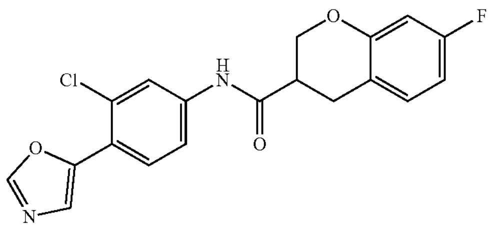 [SMILES: O=C(Nc1ccc(-c2cnco2)c(Cl)c1)C1COc2cc(F)ccc2C1]

enantiomer with the longer retention time from the chiral HPLC resolution

31

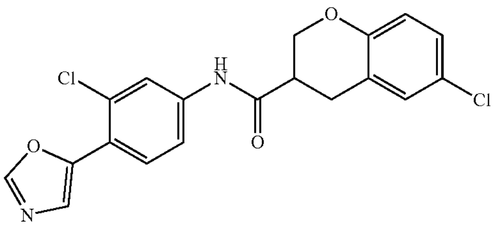 [SMILES: O=C(Nc1ccc(-c2cnco2)c(Cl)c1)C1COc2ccc(Cl)cc2C1]

(racemate)

32

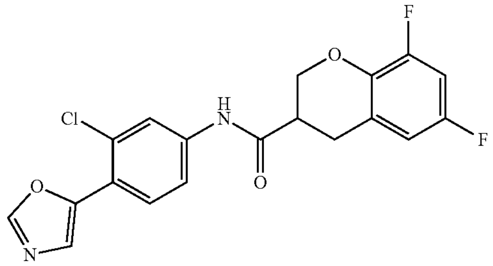 [SMILES: O=C(Nc1ccc(-c2cnco2)c(Cl)c1)C1COc2c(F)cc(F)cc2C1]

(racemate)

33

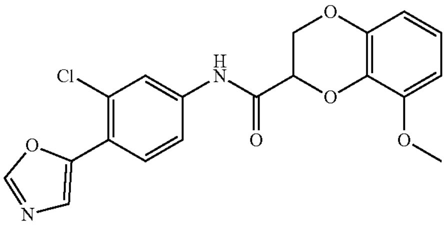 [SMILES: COc1cccc2c1OC(C(=O)Nc1ccc(-c3cnco3)c(Cl)c1)CO2]

(racemate)

34

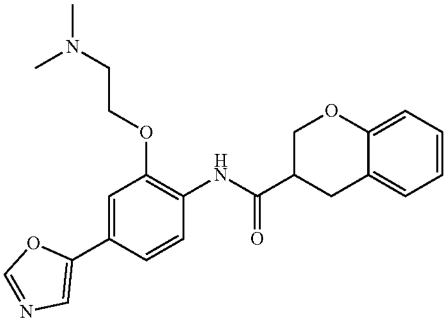 [SMILES: CN(C)CCOc1cc(-c2cnco2)ccc1NC(=O)C1COc2ccccc2C1]

(racemate)

-continued

35

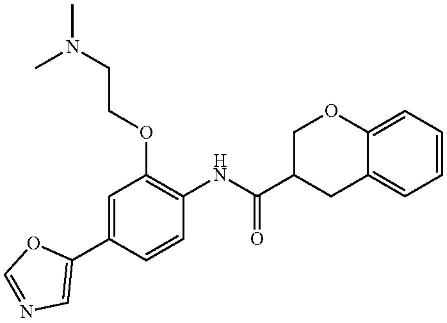 [SMILES: CN(C)CCOc1cc(-c2cnco2)ccc1NC(=O)C1COc2ccccc2C1]

enantiomer with the shorter retention time from the chiral HPLC resolution

36

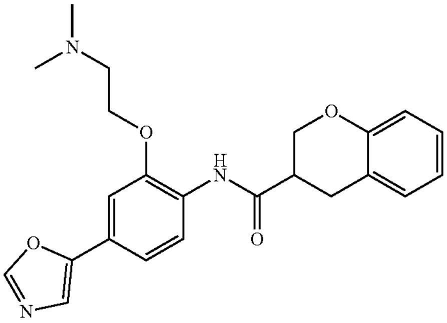 [SMILES: CN(C)CCOc1cc(-c2cnco2)ccc1NC(=O)C1COc2ccccc2C1]

enantiomer with the longer retention time from the chiral HPLC resolution

37

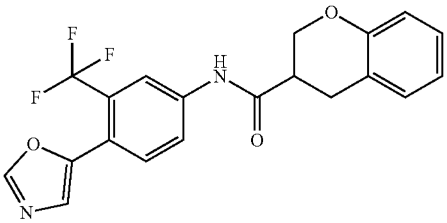 [SMILES: O=C(Nc1ccc(-c2cnco2)c(C(F)(F)F)c1)C1COc2ccccc2C1]

(racemate)

38

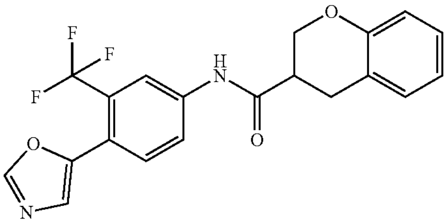 [SMILES: O=C(Nc1ccc(-c2cnco2)c(C(F)(F)F)c1)C1COc2ccccc2C1]

enantiomer with the shorter retention time from the chiral HPLC resolution

39

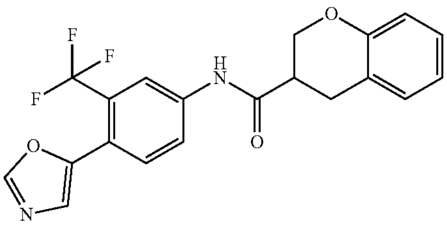 [SMILES: O=C(Nc1ccc(-c2cnco2)c(C(F)(F)F)c1)C1COc2ccccc2C1]

enantiomer with the longer retention time from the chiral HPLC resolution

-continued

40

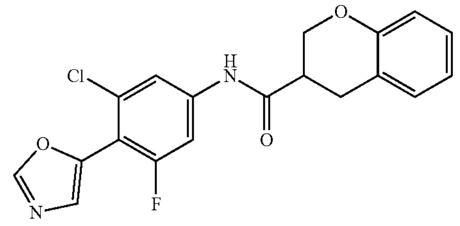 [SMILES: O=C(Nc1cc(F)c(-c2cnco2)c(Cl)c1)C1COc2ccccc2C1]

enantiomer with the shorter retention time from the chiral HPLC resolution

41

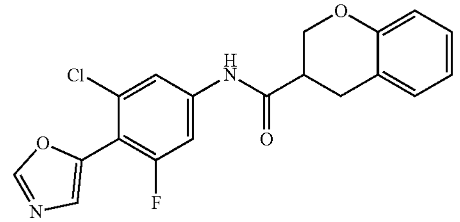

enantiomer with the longer retention time from the chiral HPLC resolution

42

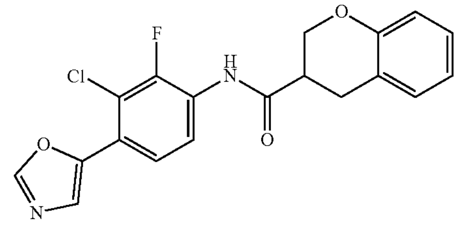 [SMILES: O=C(Nc1ccc(-c2cnco2)c(Cl)c1F)C1COc2ccccc2C1]

(racemate)

43

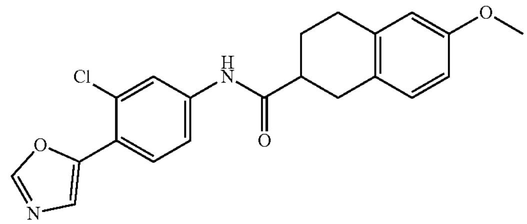 [SMILES: COc1ccc2c(c1)CCC(C(=O)Nc1ccc(-c3cnco3)c(Cl)c1)C2]

(racemate)

44

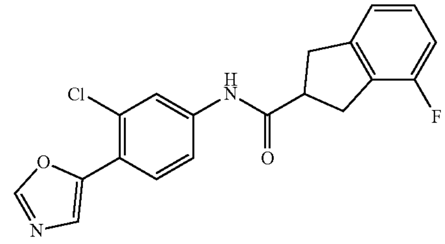 [SMILES: O=C(Nc1ccc(-c2cnco2)c(Cl)c1)C1Cc2cccc(F)c2C1]

(racemate)

-continued

45

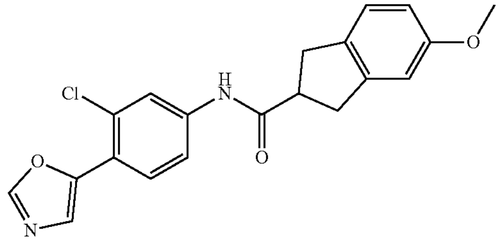 [SMILES: COc1ccc2c(c1)CC(C(=O)Nc1ccc(-c3cnco3)c(Cl)c1)C2]

(racemate)

46

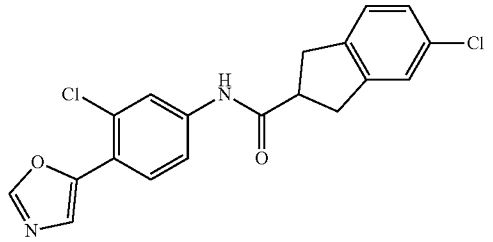 [SMILES: O=C(Nc1ccc(-c2cnco2)c(Cl)c1)C1Cc2ccc(Cl)cc2C1]

(racemate)

47

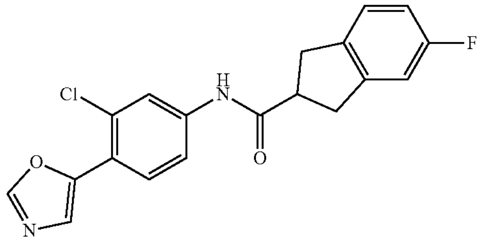 [SMILES: O=C(Nc1ccc(-c2cnco2)c(Cl)c1)C1Cc2ccc(F)cc2C1]

(racemate).

9. The method according to claim 1, wherein the retinal cells are regenerated via the proliferation and/or differentiation of retinal pigment epithelium cells.

10. The method according to claim 1, wherein the retinal disease selected from the group consisting of a disease leading to atrophy, degeneration or death of the retinal pigment epithelium.

11. The method according to claim 10, wherein the retinal disease is selected from the group consisting of early age-related macular degeneration, dry age-related macular degeneration, geographic atrophy (GA) and wet age-related macular degeneration.

12. The method according to claim 11, wherein the retinal disease is dry age-related macular degeneration.

13. The method according to claim 10, wherein the retinal disease is selected from the group consisting of Best disease, autosomal recessive bestrophinopathy (ARB), gyrate atrophy, North Carolina macular dystrophy, central areolar choroidal dystrophy (CACD), Sorsby macular dystrophy, familial dominant drusen, cuticular or basal laminar drusen, retinopathy of prematurity, myopic degeneration, polypoidal choroidal vasculopathy (PCV), central serious retinopathy, angioid streaks, retinal detachment, retinal dialysis, Vogt-Koyanagi-Harada (VKH), acute posterior multifocal placoid pigment epitheliopathy (APMPPE), persistent placoid maculopathy (PPM) relentless placoid chorioretinopathy (RPC), serpiginous choroiditis, serpiginous-like choroiditis (multifocal serpiginoid choroiditis), multiple evanescence white dot syndrome (MEWDS) or Birdshot uveitis (vitiliginous chorioretinitis), toxoplasmosis, toxocariasis, rubella, Behgets disease, choroidal hemangioma, trauma, choroidal rupture, idiopathic retinitis—vasculitis—aneurysms and neuroretinitis (IRVAN), sympathetic ophthalmia, post-operative inflammation, er-non-arteritic ischemic optic neuropathy, or retinal degeneration.

14. A pharmaceutical composition comprising a compound (I)

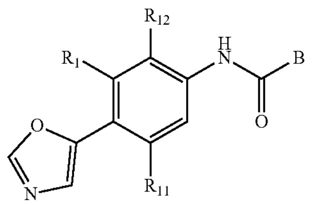

or a pharmaceutically acceptable salt, a racemic mixture, a corresponding enantiomer or, if applicable, a corresponding diastereomer thereof, wherein:

$R_1$, $R_{11}$ and $R_{12}$ are independently selected from the group consisting of hydrogen, fluoro, chloro, methoxy, trifluoromethyl, methyl and difluoromethoxy, whereby at least one of $R_1$, $R_{11}$ and $R_{12}$ is not hydrogen B is selected from the group consisting of a residue of formula (II), (III), (IV), (V), (VI) and (VII)

(II)

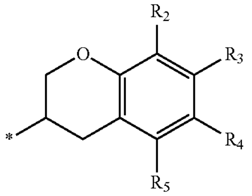

(III)

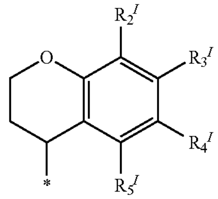

(IV)

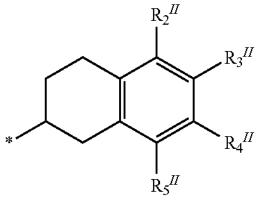

-continued (V)

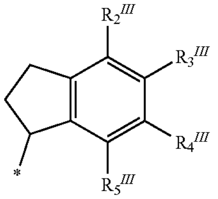

(VI)

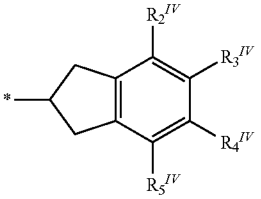

(VII)

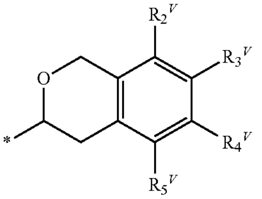

wherein

"*" denotes the point of attachment to the remainder of the molecule, and $R_2$, $R_3$, $R_4$, $R_5$, $R_2^I$, $R_3^I$, $R_4^I$, $R_5^I$, $R_2^{II}$, $R_3^{II}$, $R_4^{II}$, $R_5^{II}$, $R_2^{III}$, $R_3^{III}$, $R_4^{III}$, $R_5^{III}$, $R_2^{IV}$, $R_3^{IV}$, $R_4^{IV}$, $R_5^{IV}$, $R_2^V$, $R_3^V$, $R_4^V$, $R_5^V$ are independently selected from the group consisting of hydrogen, a linear or branched alkyl having 1 to 3 carbon atoms, fluoro, chloro, bromo, methoxy, ethoxy, propoxy, trifluoromethyl and difluoromethoxy as a therapeutically active substance and a pharmaceutically acceptable carrier and/or adjuvant for use in the treatment and/or prevention of a disease involving the retinal pigment epithelium.

15. The pharmaceutical composition according to claim 14, wherein the pharmaceutical preparation is suitable for intraocular injection or for topical ophthalmic applications.

16. The pharmaceutical composition according to claim 14, comprising a pharmaceutically acceptable salt of the compound of formula (I).

17. The pharmaceutical composition according to claim 14, further comprising one or more additional therapeutic agents.

18. The pharmaceutical composition according to claim 14, wherein the pharmaceutical composition provides controlled release properties.

19. The method according to claim 1, wherein the retinal degeneration is associated with a systemic disease selected from the group consisting of diabetes mellitus, sickle cell disease or radiation retinopathy.

* * * * *